United States Patent
Stougaard et al.

(10) Patent No.: US 7,727,572 B2
(45) Date of Patent: *Jun. 1, 2010

(54) RECOMBINANT HEXOSE OXIDASE, A METHOD OF PRODUCING SAME AND USE OF SUCH ENZYME

(75) Inventors: Peter Stougaard, Skibby (DK); Ole Cai Hansen, Varlose (DK)

(73) Assignee: Danisco A/S, Copenhagen (DK)

( * ) Notice: Subject to any disclaimer, the term of this patent is extended or adjusted under 35 U.S.C. 154(b) by 369 days.

This patent is subject to a terminal disclaimer.

(21) Appl. No.: 11/979,134

(22) Filed: Oct. 31, 2007

(65) Prior Publication Data

US 2009/0041899 A1    Feb. 12, 2009

Related U.S. Application Data

(60) Continuation of application No. 10/919,492, filed on Aug. 17, 2004, now Pat. No. 7,544,795, which is a continuation of application No. 09/824,053, filed on Apr. 3, 2001, now Pat. No. 6,924,366, which is a division of application No. 08/669,304, filed on Sep. 11, 1996, now Pat. No. 6,251,626.

(51) Int. Cl.
| | |
|---|---|
| A21D 10/00 | (2006.01) |
| A21D 8/04 | (2006.01) |
| A23K 1/00 | (2006.01) |
| A23K 1/165 | (2006.01) |
| A23L 1/00 | (2006.01) |
| A23L 1/10 | (2006.01) |
| A23L 1/105 | (2006.01) |
| C12N 9/04 | (2006.01) |
| C12N 1/00 | (2006.01) |
| C12N 1/15 | (2006.01) |
| C12N 1/16 | (2006.01) |
| C12N 15/53 | (2006.01) |
| C12N 15/80 | (2006.01) |
| C12N 15/81 | (2006.01) |

(52) U.S. Cl. ............... 426/549; 426/623; 426/630; 426/635; 435/190; 435/252.3; 435/254.11; 435/254.2; 435/254.21; 536/23.2

(58) Field of Classification Search .............. None
See application file for complete search history.

(56) References Cited

U.S. PATENT DOCUMENTS

| 2,783,150 | A | 2/1957 | Luther |
|---|---|---|---|
| 3,520,702 | A | 7/1970 | Menzi |
| 5,059,430 | A | 10/1991 | Bowles |
| 5,094,951 | A | 3/1992 | Rosenberg |
| 5,108,765 | A | 4/1992 | Maat et al. |
| 5,318,785 | A | 6/1994 | DeStefanis |
| 5,451,413 | A | 9/1995 | Fok et al. |
| 5,602,018 | A | 2/1997 | Kopetzki et al. |
| 5,650,188 | A | 7/1997 | Gaubert et al. |
| 5,858,764 | A | 1/1999 | Osinga et al. |
| 5,916,607 | A | 6/1999 | Mutsaers et al. |
| 6,039,983 | A | 3/2000 | Wagner et al. |
| 6,251,626 | B1 | 6/2001 | Stougaard et al. |
| 6,358,543 | B1 | 3/2002 | Soe et al. |
| 6,406,723 | B1 | 6/2002 | Soe et al. |
| 6,586,209 | B1 | 7/2003 | Van Gorcom et al. |
| 6,924,366 | B2 | 8/2005 | Stougaard et al. |
| 6,967,035 | B2 | 11/2005 | Bojsen |
| 2002/0064577 | A1 | 5/2002 | Soe et al. |
| 2004/0253671 | A1 | 12/2004 | Johansen et al. |

FOREIGN PATENT DOCUMENTS

| AR | 002301 | 3/1998 |
|---|---|---|
| CA | 2012723 | 9/1990 |
| CA | 2134597 | 4/1995 |
| CA | 2151978 | 12/1995 |
| CA | 2157718 | 3/1996 |
| CA | 2224143 | 12/1996 |
| CL | 858-1991 | 3/1992 |
| CL | 1376-1992 | 9/1993 |
| CL | 1363-95 | 9/1994 |
| CL | 39483 | 9/1994 |
| CL | 875-95 | 6/1995 |
| CL | 1595-1994 | 4/1996 |
| CL | 875-1994 | 5/1996 |
| CL | 1363-1995 | 8/1996 |

(Continued)

OTHER PUBLICATIONS

Liaud et al., *J. Mol. Evol.*, vol. 38, p. 319-327 (1994).
Oxford Dictionary of Biochemistry and Molecular Biology, Revised Edition, Oxford University Press, ISBN 0198506732, p. 250 (2000).
TA Brown, *Gene Cloning: An introduction*, Published by Chapman and Hall, ISBN 0412342103, p. 236 (1990).
Atividades de Hexose Oxidase e Glicose Oxidase EMBL EBI GO:0047979 (2003) and GO0046562 (2002).
Jakobsen et al., *Nucleic Acids Research*, vol. 18, No. 12, p. 3669 (1990).
A Dictionary of Genetics, 4th edition, RC King & WD Standsfield (editiors), Oxford University Press, p. 269 (1990).
Glucose Oxidase, An Extract from the Enzyme Handbook, p. 1-7 (1995).
Kelley and Reddy, *J. Bacteriology*, vol. 166, p. 269-274 (1986).

(Continued)

*Primary Examiner*—Nashaat T Nashed
*Assistant Examiner*—William W Moore
(74) *Attorney, Agent, or Firm*—Steptoe & Johnson LLP

(57) ABSTRACT

A method of producing hexose oxidase by recombinant DNA technology, recombinant hexose oxidase and the use of such enzyme, in particular in the manufacturing of food products such as doughs and dairy products, animal feed, pharmaceuticals, cosmetics, dental care products and in the manufacturing of lactones. Suitable sources of DNA coding for the enzyme are marine algal species including *Chondrus crispus*, *Iridophycus flaccidum* and *Euthora cristata*. In useful embodiments, the recombinant hexose oxidase is produced by *Pichia pastoris*, *Saccharomyces cerevisiae* or *E. coli*.

20 Claims, 14 Drawing Sheets

FOREIGN PATENT DOCUMENTS

Figure 1:
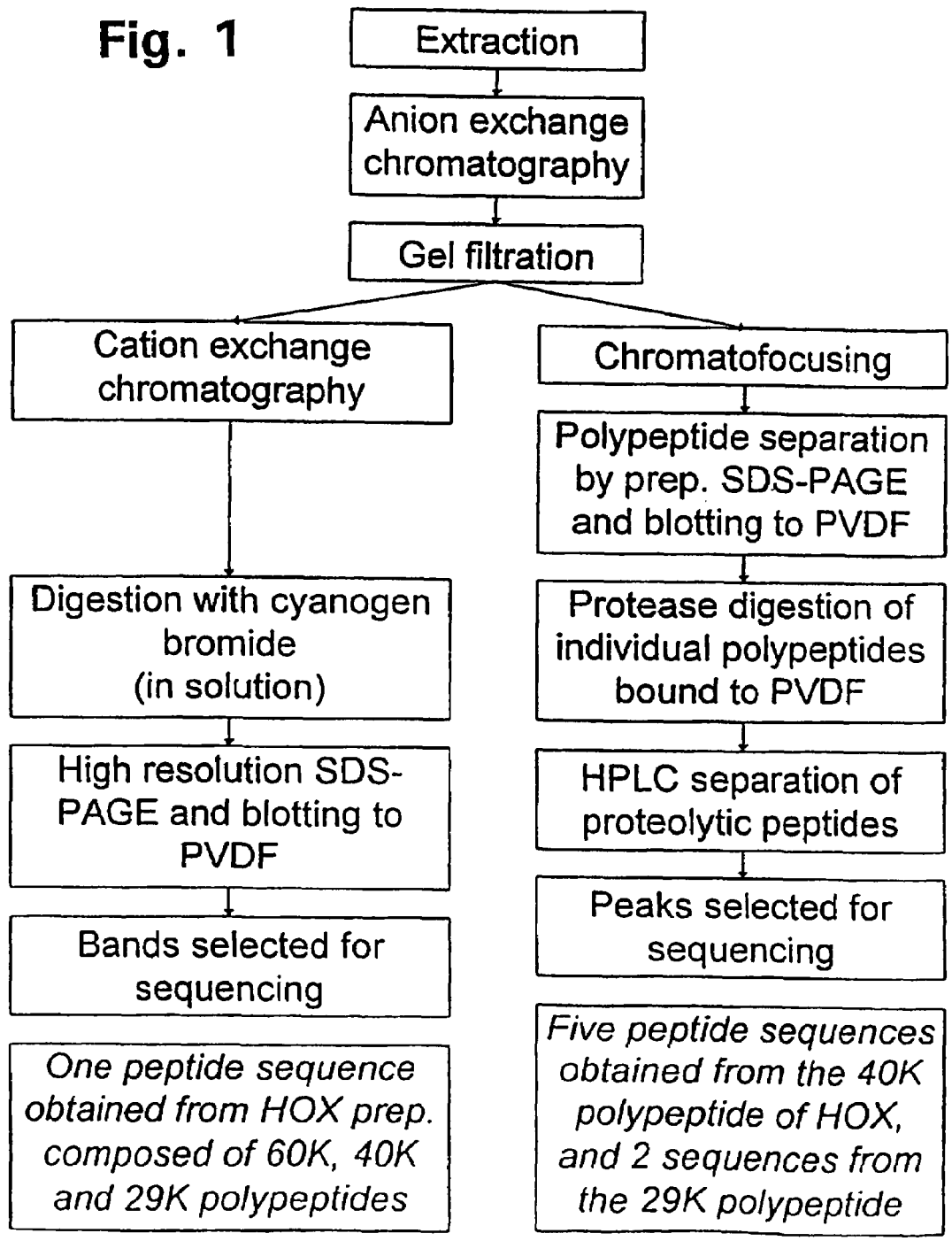

| | | |
|---|---|---|
| DE | 1050703 | 3/1956 |
| DE | 4301904 | 2/1994 |
| DK | 1050703 | 3/1956 |
| DK | 4301904 | 2/1994 |
| EP | 0010296 | 4/1980 |
| EP | 0321811 | 6/1989 |
| EP | B 0321 811 | 6/1989 |
| EP | 0338452 | 10/1989 |
| EP | B 0338 452 | 10/1989 |
| EP | 0468731 | 7/1991 |
| EP | 0396162 | 1/1993 |
| EP | 0585988 B1 | 3/1994 |
| EP | 0682116 | 11/1995 |
| EP | 0832245 | 4/1998 |
| GB | 2358784 | 8/2001 |
| JP | 73016612 B | 12/1970 |
| JP | B48-016612 | 5/1973 |
| JP | 61-085158 | 4/1986 |
| JP | 92-084848 | 7/1990 |
| JP | 02224143 | 9/1990 |
| JP | 04200339 | 7/1992 |
| JP | 6-000010444 | 10/1994 |
| JP | 6296467 | 10/1994 |
| JP | 07274807 | 10/1995 |
| JP | 03164127 | 7/1999 |
| JP | 04207145 | 7/1999 |
| JP | 04207146 A | 7/1999 |
| WO | WO94/04035 | 3/1994 |
| WO | WO9501727 A | 1/1995 |
| WO | 95/29996 | 11/1995 |
| WO | 96/40935 | 12/1996 |
| WO | WO9639851 | 12/1996 |
| WO | WO98/45453 | 10/1998 |
| WO | WO99/31990 | 7/1999 |
| WO | WO00/32758 | 6/2000 |
| WO | WO01/39602 A1 | 6/2001 |
| WO | WO02/00852 | 1/2002 |
| WO | WO02/03805 | 1/2002 |
| WO | WO02/065854 | 8/2002 |
| WO | WO02/066622 | 8/2002 |

OTHER PUBLICATIONS

Giffhorn, *Appl. Microbiol. Biotechnol.*, vol. 54, p. 727-740 (2000).
Kaplan, *Methods in Enzymology*, vol. 3, p. 107-110 (1957).
Smith and Whelan, *Biochemical Preparations*, vol. 10, p. 126-130 (1963).
Liaud, M-F., Valentin, C., Brandt, U., Bouget, F-Y., Kloareg, B., and Cerff, R. (1993) Plant Mol. Biol. 23, 981-994.
Makrides, 1996, Microbiological Reviews, vol. 60, No. 3, p. 512-538.
Conference May 6-8, 1999, in Santorini, Greece, Lipases of Lipids Structure, Function and Biotechnological Applications. Slides presented by Charlotte Poulsen.
Kalisz et al, 1991 "Effects of carbohydrate depletion on the structure, stability and activity of glucose oxidase from *Aspergillus niger*", Biochimica et Biophysica Acta, vol. 1080, No. 2, p. 138-142.
expasy.ch/cgi-bin/enzyme-search-ec, 1961.
chem.qmul.ac.uk/iubmb/enzyme/EC1.1.3.4.html, 1961.
Groen et al, Eur. J. Biochem, vol. 244, p. 858-861 1997.
AACC Method 36-01A (replaced 2000 by method 56-99 Glossary—Grain and flour), 1984.
AACC Method 54-10, 1982.
Definition of "hexose", Webster Dictionary, p. 1065, 1993 (ISBN: 0-87779-201-1).
PCT International search report from the International Searching Authority in PCT/DK96/00239 issued Sep. 11, 1996.
U.S. Appl. No. 09/932,923, filed Aug. 21, 2001.
Poulsen C et al, Cereal Chem, vol. 75, No. 1, p. 51-57 (1998).
Krog N J, Cereal Foods World, vol. 24, No. 1, p. 10-11 (1979).
Matos A R et al, FEBS Letters, vol. 491, p. 188-192 (2001).
Withers-Martinez C et al, Structure, vol. 4, No. 11, p. 1363-1374 (1996).
Cordle R A, Journal of Lipid Research, vol. 39, p. 17591767 (1998).
Sahsah Y et al, Biochemica et Biophysica Acta, vol. 1215, p. 66-73 (1994).
O'Sullivan J et al, J Plant Physiol, vol. 131, p. 393-4004 (1987).
Carriere F et al, Biochemistry, vol. 36, p. 239-248 (1997).
Bornscheuer U T, Enzyme and Microbial Technology, vol. 17, p. 578-586 (1995).
Hou C T, Journal of Industrial Microbiology, vol. 13 p. 242-248 (1994).
Villeneuve P et al, Inform, vol. 8, No. 6, p. 640-650 (1997).
Cammann K et al, Angew Chem Int Ed Engl, vol. 30, p. 516-539 (1991).
Allen T M et al, Biosensors and Bioelectronics, vol. 10, p. 621-631 (1995).
Wiseman A, "Immobilization of Glucose Oxidase into Membranes as Sensors for Food Analysis", Elsevier Science Publishers (1987).
Wilson R et al, Biosensors and Bioelectronics, vol. 7, p. 165-185 (1992).
Raba J et al, Critical Reviews in Analytical Chemistry, vol. 25, No. 1, p. 1-42 (1995).
Volc J et al, Folia Microbiol, vol. 3, p. 141-147 (1985).
Lin S-F et al, Biochimica et Biophysica Acta, vol. 1118, p. 41-47 (1991).
Qi Si J, Food Tech Europe, vol. 3, No. 1, p. 6064 (1996) Novo Nordisk Ferment Ltd.
Weipert D, Getreide Mehl und Brot vol. 26, No. 10, p. 275-280 (1972), English language translation of abstract.
Nicolas J, Ann. Technol. Agric, vol. 28, No. 4, p. 445-468 (1979), English language translation of abstract.
Mine Y, Food Research International, vol. 29, No. 1, p. 81084 (1996).
Marion Didier et al, Interactions: the Keys to Cereal Quality (ed Hamer & Hoseney), chapter 6, p. 131-167 (1998).
Poulsen C H et al, The First European Symposium on Enzymes and Grain Processing, p. 204-214 (1997).
Marion D et al, Wheat Structure Biochemistry and Functionality, ed Scholfield JP, p. 245-260 (1995).
"Unique Chance for Better Bread", Direct, A Newsletter from Danisco Ingredients (1996).
Sullivan 1973, Diss. Abstr. Int. B 34(5), 1875, CAN 80: 105204 AN 1974: 105204 CAPLUS, "Purification and characterization of hexose oxidases from the red alga *Chondrus crispus*".
Wolff A M et al, Protein Expression and Purification, vol. 2, p. 189-199, "Optimization of the Production of *Chondrus crispus* Hexose oxidase in *Pichia pastoris*" (2001).
PCT International search report from the International Searching Authority in PCT/DK96/00238 issued Apr. 11, 1996.
Pazur, J.H., et al., "Comparison of the action of Glucoamylase and Glucosyltransferase on D-Glucose, Maltose, and Malto-Oligosaccharaides," Carbohydrate Research, 58:193-202 (1977).
Pub. No. 06-296467 (JP 6296467), Oct. 25, 1994.
Kerschensteiner, *Diss. Abstr. Int. B*, vol. 39, No. 7, p. 3299 (1979).
Poulsen, C.H. et al. "Effect and functionality of lipases in dough and bread," *The First European Symposium on Enzymes and Grain Processing*, p. 204-214 (1997).
Dowling et al., (1956) "Hexose Oxidation by an enzyme system of *Malleomyces pseudomallei*", Journal of Bacteriology 72:555-560.
Bean et al., (1961) "Carbohydrate Metabolism of Citrus Fruits", Journal of Biological Chemistry 236:1235-1240.
Ellman, George L. (1958) "A Colorimetric Method for Determining Low Concentrations of Mercaptans", Archives of Biochemistry and Biophysics 74:443-450.
Bak et al., "A Method For Testing The Strengthening Effect Of Oxidative Enzymes in Dough", preentered at a symposium entitled "Wheat Structure, Biochemistry and Functionality", held on Apr. 10-12, 1995, UK, (Abstract).
Perella, F.W., (1988) Analytical Biochemistry, 174:437-447.
D.A. Kerschensteiner. (1978) "The Mechanism Of Action and the State of Copper in Hexose Oxidase", Thesis, pp. iii-xiii.
Clare et al., (1991) Bio/Technology 9:455-460 [3].
Cregg et al., (1987) In: Biological Research on Industrial Yeast, vol. II, Stewart, G. G. et al. (Eds.), pp. 1-18 [4].

Pedersen et al., (1996) J. Biol. Chem. 271: 2514-2522 [10].
Sahm et al., (1973) Eur. J. Biochem. 36: 250-256 [12].
Tschopp et al., (1987) Bio/Technology 5: 1305-1308 [17].
Barkholt, V. and Jensen, A.L. (1989) Amino Acid Analysis: Determination of Cysteine plus Half-Cystine in Proteins after Hydrochloric Acid Hydrolysis with a Disulfide Compound as Additive. Analytical Biochemistry 177:318-322.
Fernandez, J. et al. (1992) Internal Protein Sequence Analysis: Enzymatic Digestion for Less than 10.mu.g of Protein Bound to Polyvinylidene Difluoride or Nitrocellulose Membranes. Analytical Biochemistry, 201:255-264.
Fernandez, J. et al. (1994) An Improved Procedure for Enzymatic Digestion of Polyvinylidene Difluoride-Bound Proteins for Internal Sequence Analysis. Analytical Biochemistry, 218:112-117.
Groppe, J.C. and Morse, D.E. (1993) Isolation of full-length RNA templates for reverse transcription from tissues rich in RNase and proteoglycans, Anal. Biochem., 210:337-343.
Kerschensteiner, D.A. and Klippenstein, G.L. (1978) Purification, Mechanism, and State of Copper in Hexose Oxidase. Federation Proceedings 37:1816 abstract.
Laemmli. (1970) Cleavage of Structural Proteins during the Assembly of the Head of Bacteriophage T4. Nature (London) 227:680-685.
Rand, A.G. (1972) Direct enzymatic conversion of lactose to acid: glucose oxidase and hexose oxidase. Journal of Food Science 37:698-701.
Schagger, H. and von Jagow, G. (1987) Tricine-Sodium Dodecyl Sulfate-Polyacrylamide Gel Electrophoresis for the Separation of Proteins in the Range from 1 to 100 kDa. Analytical Biochemistry 166:368-379.
Sock, J. and Rohringer, R. (1988) Activity Staining of Blotted Enzymes by Reaction Coupling with Transfer Membrane-Immobilized Auxiliary Enzymes. Analytical Biochemistry 171:310-319.
Sullivan, J.D. and Ikawa, M. (1973) Purification and Characterization of Hexose Oxidase from the red Alga *Chondrus crispus*. Biochemica et Biophysica Acta 309:11-22.
Yeh, K-W, R.H. Juang and Su, J-C. (1991) A Rapid and efficient method for RNA isolation from plants with high carbohydrate content. Focus 13(3):102-103.
Bean and Hassid (1956) J. Biol. Chem., 218:4 25-436.
Maes et al., (1993) Analytica Chimica Acta, 284: 281-290.
Ikawa, (1982) Methods Enzymol. 89: 145-149.
Christiansen (1993) "Application of Oxidoreductases for Food Preservation" in Progress Report of R&D Projects and Concerted Actions published by the European Communities, Luxembourg, 1993, p. 32-36.

"Enzyme Technology in Flour Milling and Baking", Baking Industry Europe (Alan Gordon, editor), S. Haarasilta and T. Pullinen (1993), pp. 49-52.
"Enzyme Nomenclature (1984) (Recommendations of the Nomenclature Committee of the International Union of Biochemistry on the Nomenclature and Classification of Enzyme-Catalysed Reactions)," pp. v, ix, and 50-51.
"Glucose Oxidase: Production, Properties, Present and Potential Applications", Soc. Chem. Ind. (Londen), (1961), L.A. Underkofler, p. 72-86.
"Methods in Enzymology", Biomass Part B Glucose Oxidase of *Phanerochaete chrysosporium*, R.L. Kelley and C.A. Reddy (1988), 161, pp. 306-317.
"Baking Science & Technology", E.J. Pyler (1982), vol. 1, pp. 314-316.
"Novel Enzyme Combinations A New Tool to Improve Baking Results", Agro-Industry Hi-Tech, S. Haarasilta and T. Pullinen, (May/Jun. 1992), p. 12-13.
"Enzyme Nomenclature (Recommendations of the Nomenclature Committee of the International Union of Biochemistry and Molecular Biology on the Nomenclature and Classification of Enzymes)" (1992), p. 56.
"Enzyme Function", Experimental Report from Novo Nordisk, Mar. 13, 1997, 2 pages.
Knoll et al., J. Chromatog., 55 (1971), 425-428.
"DEEO.RTM." A glucose oxidase and catalase enzyme system product sheet from Miles laboratories- Enzymes from Miles (technical Information) (1976), 5 pages.
"Enzymes in Food Processing", 2nd Ed. by G. Reed, Universal Foods Corporation, Academic Press (1975), p. 222-229.
"Properties and Applications of the Fungal Enzyme Glucose Oxidase", reprinted from "Proceedings of the International Symposium on Enzyme Chemistry", Tokyo and Kyoto, (1957) L.A. Underkofler, (1958), pp. 486-490.
"The Oxidation of Glucose and Related Compounds by Glucose Oxidase from *Aspergillus niger*", Biochemistry, Pazur et al., vol. 3(4), 1964, 578-583.
"Technology of Cereals (with special reference to wheat)", 2.sup.nd Ed., Pergamom Press Ltd. N. L. Kent, (1975), pp. iv-v, 48-49, and 72-73.
"Gluzyme™" product sheet from Novo Nordisk Enzyme Process Division, Jan. 1994, 2 pages.
Hansen et al., (1997) "Hexose oxidase from the red alga *Chondrus crispus*. Purification, molecular cloning, and expression in *Pichia patoris*," Journal of Biological Chemistry, vol. 272, pp. 11581-11587.

```
                         SEQUENCE LISTING

<160> NUMBER OF SEQ ID NOS: 37

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Tyr Glu Pro Tyr Gly Gly Val Pro
 1               5

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (15)..(17)
<223> OTHER INFORMATION: any naturally occurring amino acid, Asx or Glx
<220> FEATURE:
<221> NAME/KEY: MOD_RES
<222> LOCATION: (20)
<223> OTHER INFORMATION: any naturally occurring amino acid, Asx or Glx

<400> SEQUENCE: 2

Ala Ile Ile Asn Val Thr Gly Leu Val Glu Ser Gly Tyr Asp Xaa Xaa
 1               5                  10                  15

Xaa Gly Tyr Xaa Val Ser Ser
                20
```

```
<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (15)
<223> OTHER INFORMATION: any naturally occurring amino acid, Asx or Glx

<400> SEQUENCE: 3

Asp Leu Pro Met Ser Pro Arg Gly Val Ile Ala Ser Asn Leu Xaa Phe
 1               5                  10                  15

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)
<223> OTHER INFORMATION: any naturally occurring amino acid, Asx or Glx

<400> SEQUENCE: 4

Asp Ser Glu Gly Asn Asp Gly Glu Leu Phe Xaa Ala His Thr
 1               5                  10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Tyr Tyr Phe Lys
 1

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (14)
<223> OTHER INFORMATION: any naturally occurring amino acid, Asx or Glx

<400> SEQUENCE: 6

Asp Pro Gly Tyr Ile Val Ile Asp Val Asn Ala Gly Thr Xaa Asp
 1               5                  10                  15

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7
```

```
Leu Gln Tyr Gln Thr Tyr Trp Gln Glu Glu Asp
  1               5                  10
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)
<223> OTHER INFORMATION: any naturally occurring amino acid, Asx or Glx

<400> SEQUENCE: 8

```
Xaa Ile Arg Asp Phe Tyr Glu Glu Met
  1               5
```

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (15)
<223> OTHER INFORMATION: Asp or Asn
<220> FEATURE:
<221> NAME/KEY: MOD_RES
<222> LOCATION: (16)
<223> OTHER INFORMATION: Asp or Ala
<220> FEATURE:
<221> NAME/KEY: MOD_RES
<222> LOCATION: (17)
<223> OTHER INFORMATION: Arg or Trp
<220> FEATURE:
<221> NAME/KEY: MOD_RES
<222> LOCATION: (20)
<223> OTHER INFORMATION: variable amino acid

<400> SEQUENCE: 9

```
Ala Ile Ile Asn Val Thr Gly Leu Val Glu Ser Gly Tyr Asp Xaa Xaa
  1               5                  10                  15

Xaa Gly Tyr Xaa Val Ser Ser
             20
```

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

```
Asp Leu Pro Met Ser Pro Arg Gly Val Ile Ala Ser Asn Leu Trp Phe
  1               5                  10                  15
```

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)

```
<223> OTHER INFORMATION: variable amino acid

<400> SEQUENCE: 11

Asp Ser Glu Gly Asn Asp Gly Glu Leu Phe Xaa Ala His Thr
 1               5                  10

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Tyr Tyr Phe Lys
 1

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Asp Pro Gly Tyr Ile Val Ile Asp Val Asn Ala Gly Thr Pro Asp
 1               5                  10                  15

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Leu Gln Tyr Gln Thr Tyr Trp Gln Glu Glu Asp
 1               5                  10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)
<223> OTHER INFORMATION: variable amino acid

<400> SEQUENCE: 15

Xaa Ile Arg Asp Phe Tyr Glu Glu Met
 1               5

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (3)
<223> OTHER INFORMATION: inosine
```

```
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (12)
<223> OTHER INFORMATION: inosine
<220> FEATURE:
<221> NAME/KEY: modified_base
<222> LOCATION: (15)
<223> OTHER INFORMATION: a, t, c or g

<400> SEQUENCE: 16
ytngtngarw snggntayga                                             20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (12)
<223> OTHER INFORMATION: inosine
<220> FEATURE:
<221> NAME/KEY: modified_base
<222> LOCATION: (15)
<223> OTHER INFORMATION: a, t, g or g
<220> FEATURE:
<221> NAME/KEY: modified_base
<222> LOCATION: (21)
<223> OTHER INFORMATION: a, t, c or g

<400> SEQUENCE: 17
aaccanarrt tngangcdat nac                                         23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (6)
<223> OTHER INFORMATION: inosine
<220> FEATURE:
<221> NAME/KEY: modified_base
<222> LOCATION: (15)
<223> OTHER INFORMATION: inosine
<220> FEATURE:
<221> NAME/KEY: modified_base
<222> LOCATION: (21)
<223> OTHER INFORMATION: a, t, c or g

<400> SEQUENCE: 18
garggnaayg ayggngarct ntt                                         23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      Oligonucleotide
```

```
<220> FEATURE:
<221> NAME/KEY: modified_base
<222> LOCATION: (3)
<223> OTHER INFORMATION: inosine
<220> FEATURE:
<221> NAME/KEY: modified_base
<222> LOCATION: (9)
<223> OTHER INFORMATION: inosine
<220> FEATURE:
<221> NAME/KEY: modified_base
<222> LOCATION: (18)
<223> OTHER INFORMATION: a, t, c or g

<400> SEQUENCE: 19
aanagytcnc crtcrttncc ytc                                          23

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
attggggctc cttcaagacc tt                                           22

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 21
tgatgattcc aaagtttc                                                18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 22
ttggaagaat acggttgg                                                18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 23
tactatttcg tctgcttggg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 24
```

```
gaactcttcc gtggtctcct                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 25
ccacctgcgt gttggggtct                                              20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 26
cagatctaca aaacatgcga g                                            21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 27
tgtcgcagac tgtacttg                                                18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 28
gagtgtacac gacataaa                                                18

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 29
atggctactc ttccccagaa ag                                           22

<210> SEQ ID NO 30
<211> LENGTH: 1801
<212> TYPE: DNA
<213> ORGANISM: Artificial Sequence
<220> FEATURE:
<223> OTHER INFORMATION: Description of Artificial Sequence: Recombinant
      DNA molecule
<220> FEATURE:
<221> NAME/KEY: CDS
<222> LOCATION: (84)..(1721)
```

<400> SEQUENCE: 30

```
tgaattcgtg ggtcgaagag cccctttgcct cgtctctctg gtaccgtgta tgtcaaaggt      60
tcgcttgcac actgaacttc acg atg gct act ctt cct cag aaa gac ccc ggt      113
                         Met Ala Thr Leu Pro Gln Lys Asp Pro Gly
                           1               5                  10 tat att gta att gat gtc aac gcg ggc acc gcg gac aag ccg gac cca         161
Tyr Ile Val Ile Asp Val Asn Ala Gly Thr Ala Asp Lys Pro Asp Pro
                 15                  20                  25 cgt ctc ccc tcc atg aag cag ggc ttc aac cgc cgc tgg att gga act         209
Arg Leu Pro Ser Met Lys Gln Gly Phe Asn Arg Arg Trp Ile Gly Thr
             30                  35                  40 aat atc gat ttc gtt tat gtc gtg tac act cct caa ggt gct tgt act         257
Asn Ile Asp Phe Val Tyr Val Val Tyr Thr Pro Gln Gly Ala Cys Thr
         45                  50                  55 gca ctt gac cgt gct atg gaa aag tgt tct ccc ggt aca gtc agg atc         305
Ala Leu Asp Arg Ala Met Glu Lys Cys Ser Pro Gly Thr Val Arg Ile
     60                  65                  70 gtc tct ggc ggc cat tgc tac gag gac ttc gta ttt gac gaa tgc gtc         353
Val Ser Gly Gly His Cys Tyr Glu Asp Phe Val Phe Asp Glu Cys Val
 75                  80                  85                  90 aag gcc atc atc aac gtc act ggt ctc gtt gag agt ggt tat gac gac         401
Lys Ala Ile Ile Asn Val Thr Gly Leu Val Glu Ser Gly Tyr Asp Asp
                 95                 100                 105 gat agg ggt tac ttc gtc agc agt gga gat aca aat tgg ggc tcc ttc         449
Asp Arg Gly Tyr Phe Val Ser Ser Gly Asp Thr Asn Trp Gly Ser Phe
            110                 115                 120 aag acc ttg ttc aga gac cac gga aga gtt ctt ccc ggg ggt tcc tgc         497
Lys Thr Leu Phe Arg Asp His Gly Arg Val Leu Pro Gly Gly Ser Cys
            125                 130                 135 tac tcc gtc ggc ctc ggt ggc cac att gtc ggc gga ggt gac ggc att         545
Tyr Ser Val Gly Leu Gly Gly His Ile Val Gly Gly Gly Asp Gly Ile
140                 145                 150 ttg gcc cgc ttg cat ggc ctc ccc gtc gat tgg ctc agc ggc gtg gag         593
Leu Ala Arg Leu His Gly Leu Pro Val Asp Trp Leu Ser Gly Val Glu
155                 160                 165                 170 gtc gtc gtt aag cca gtc ctc acc gaa gac tcg gta ctc aag tat gtg         641
Val Val Val Lys Pro Val Leu Thr Glu Asp Ser Val Leu Lys Tyr Val
                175                 180                 185 cac aaa gat tcc gaa ggc aac gac ggg gag ctc ttt tgg gca cac aca         689
His Lys Asp Ser Glu Gly Asn Asp Gly Glu Leu Phe Trp Ala His Thr
            190                 195                 200 ggt ggc ggt ggc gga aac ttt gga atc atc acc aaa tac tac ttc aag         737
Gly Gly Gly Gly Gly Asn Phe Gly Ile Ile Thr Lys Tyr Tyr Phe Lys
            205                 210                 215 gat ttg ccc atg tct cca cgg ggc gtc atc gca tca aat tta cac ttc         785
Asp Leu Pro Met Ser Pro Arg Gly Val Ile Ala Ser Asn Leu His Phe
220                 225                 230 agc tgg gac ggt ttc acg aga gat gcc ttg cag gat ttg ttg aca aag         833
Ser Trp Asp Gly Phe Thr Arg Asp Ala Leu Gln Asp Leu Leu Thr Lys
235                 240                 245                 250 tac ttc aaa ctt gcc aga tgt gat tgg aag aat acg gtt ggc aag ttt         881
Tyr Phe Lys Leu Ala Arg Cys Asp Trp Lys Asn Thr Val Gly Lys Phe
                255                 260                 265 caa atc ttc cat cag gca gcg gaa gag ttt gtc atg tac ttg tat aca         929
Gln Ile Phe His Gln Ala Ala Glu Glu Phe Val Met Tyr Leu Tyr Thr
            270                 275                 280 tcc tac tcg aac gac gcc gag cgc gaa gtt gcc caa gac cgt cac tat         977
Ser Tyr Ser Asn Asp Ala Glu Arg Glu Val Ala Gln Asp Arg His Tyr
```

```
            285                 290                 295
cat ttg gag gct gac ata gaa cag atc tac aaa aca tgc gag ccc acc     1025
His Leu Glu Ala Asp Ile Glu Gln Ile Tyr Lys Thr Cys Glu Pro Thr
    300                 305                 310 aaa gcg ctt ggc ggg cat gct ggg tgg gcg ccg ttc ccc gtg cgg ccg     1073
Lys Ala Leu Gly Gly His Ala Gly Trp Ala Pro Phe Pro Val Arg Pro
315                 320                 325                 330 cgc aag agg cac aca tcc aag acg tcg tat atg cat gac gag acg atg     1121
Arg Lys Arg His Thr Ser Lys Thr Ser Tyr Met His Asp Glu Thr Met
                335                 340                 345 gac tac ccc ttc tac gcg ctc act gag acg atc aac ggc tcc ggg ccg     1169
Asp Tyr Pro Phe Tyr Ala Leu Thr Glu Thr Ile Asn Gly Ser Gly Pro
            350                 355                 360 aat cag cgc ggc aag tac aag tct gcg tac atg atc aag gat ttc ccg     1217
Asn Gln Arg Gly Lys Tyr Lys Ser Ala Tyr Met Ile Lys Asp Phe Pro
        365                 370                 375 gat ttc cag atc gac gtg atc tgg aaa tac ctt acg gag gtc ccg gac     1265
Asp Phe Gln Ile Asp Val Ile Trp Lys Tyr Leu Thr Glu Val Pro Asp
    380                 385                 390 ggc ttg act agt gcc gaa atg aag gat gcc tta ctc cag gtg gac atg     1313
Gly Leu Thr Ser Ala Glu Met Lys Asp Ala Leu Leu Gln Val Asp Met
395                 400                 405                 410 ttt ggt ggt gag att cac aag gtg gtc tgg gat gcg acg gca gtc gcg     1361
Phe Gly Gly Glu Ile His Lys Val Val Trp Asp Ala Thr Ala Val Ala
                415                 420                 425 cag cgc gag tac atc atc aaa ctg cag tac cag aca tac tgg cag gaa     1409
Gln Arg Glu Tyr Ile Ile Lys Leu Gln Tyr Gln Thr Tyr Trp Gln Glu
            430                 435                 440 gaa gac aag gat gca gtg aac ctc aag tgg att aga gac ttt tac gag     1457
Glu Asp Lys Asp Ala Val Asn Leu Lys Trp Ile Arg Asp Phe Tyr Glu
        445                 450                 455 gag atg tat gag ccg tat ggc ggg gtt cca gac ccc aac acg cag gtg     1505
Glu Met Tyr Glu Pro Tyr Gly Gly Val Pro Asp Pro Asn Thr Gln Val
    460                 465                 470 gag agt ggt aaa ggt gtg ttt gag gga tgc tac ttc aac tac ccg gat     1553
Glu Ser Gly Lys Gly Val Phe Glu Gly Cys Tyr Phe Asn Tyr Pro Asp
475                 480                 485                 490 gtg gac ttg aac aac tgg aag aac ggc aag tat ggt gcc ctc gaa ctt     1601
Val Asp Leu Asn Asn Trp Lys Asn Gly Lys Tyr Gly Ala Leu Glu Leu
                495                 500                 505 tac ttt ttg ggt aac ctg aac cgc ctc atc aag gcc aaa tgg ttg tgg     1649
Tyr Phe Leu Gly Asn Leu Asn Arg Leu Ile Lys Ala Lys Trp Leu Trp
            510                 515                 520 gat ccc aac gag atc ttc aca aac aaa cag agc atc cct act aaa cct     1697
Asp Pro Asn Glu Ile Phe Thr Asn Lys Gln Ser Ile Pro Thr Lys Pro
        525                 530                 535 ctt aag gag ccc aag cag acg aaa tagtaggtca caattagtca tcgactgaag    1751
Leu Lys Glu Pro Lys Gln Thr Lys
    540                 545 tgcagcactt gtcggatacg gcgtgatggt tgcttttat aaacttggta               1801
```

<210> SEQ ID NO 31
<211> LENGTH: 546
<212> TYPE: PRT
<213> ORGANISM: Artificial Sequence
<220> FEATURE:
<223> OTHER INFORMATION: Description of Artificial Sequence: Recombinant amino acid molecule

<400> SEQUENCE: 31

-continued

```
Met Ala Thr Leu Pro Gln Lys Asp Pro Gly Tyr Ile Val Ile Asp Val
 1               5                  10                  15

Asn Ala Gly Thr Ala Asp Lys Pro Asp Pro Arg Leu Pro Ser Met Lys
                 20                  25                  30

Gln Gly Phe Asn Arg Arg Trp Ile Gly Thr Asn Ile Asp Phe Val Tyr
             35                  40                  45

Val Val Tyr Thr Pro Gln Gly Ala Cys Thr Ala Leu Asp Arg Ala Met
         50                  55                  60

Glu Lys Cys Ser Pro Gly Thr Val Arg Ile Val Ser Gly Gly His Cys
 65                  70                  75                  80

Tyr Glu Asp Phe Val Phe Asp Glu Cys Val Lys Ala Ile Ile Asn Val
                 85                  90                  95

Thr Gly Leu Val Glu Ser Gly Tyr Asp Asp Arg Gly Tyr Phe Val
                100                 105                 110

Ser Ser Gly Asp Thr Asn Trp Gly Ser Phe Lys Thr Leu Phe Arg Asp
            115                 120                 125

His Gly Arg Val Leu Pro Gly Gly Ser Cys Tyr Ser Val Gly Leu Gly
            130                 135                 140

Gly His Ile Val Gly Gly Asp Gly Ile Leu Ala Arg Leu His Gly
145                 150                 155                 160

Leu Pro Val Asp Trp Leu Ser Gly Val Glu Val Val Lys Pro Val
                165                 170                 175

Leu Thr Glu Asp Ser Val Leu Lys Tyr Val His Lys Asp Ser Glu Gly
            180                 185                 190

Asn Asp Gly Glu Leu Phe Trp Ala His Thr Gly Gly Gly Gly Asn
            195                 200                 205

Phe Gly Ile Ile Thr Lys Tyr Tyr Phe Lys Asp Leu Pro Met Ser Pro
210                 215                 220

Arg Gly Val Ile Ala Ser Asn Leu His Phe Ser Trp Asp Gly Phe Thr
225                 230                 235                 240

Arg Asp Ala Leu Gln Asp Leu Leu Thr Lys Tyr Phe Lys Leu Ala Arg
                245                 250                 255

Cys Asp Trp Lys Asn Thr Val Gly Lys Phe Gln Ile Phe His Gln Ala
                260                 265                 270

Ala Glu Glu Phe Val Met Tyr Leu Tyr Thr Ser Tyr Ser Asn Asp Ala
            275                 280                 285

Glu Arg Glu Val Ala Gln Asp Arg His Tyr His Leu Glu Ala Asp Ile
            290                 295                 300

Glu Gln Ile Tyr Lys Thr Cys Glu Pro Thr Lys Ala Leu Gly Gly His
305                 310                 315                 320

Ala Gly Trp Ala Pro Phe Pro Val Arg Pro Arg Lys Arg His Thr Ser
                325                 330                 335

Lys Thr Ser Tyr Met His Asp Glu Thr Met Asp Tyr Pro Phe Tyr Ala
            340                 345                 350

Leu Thr Glu Thr Ile Asn Gly Ser Gly Pro Asn Gln Arg Gly Lys Tyr
            355                 360                 365

Lys Ser Ala Tyr Met Ile Lys Asp Phe Pro Asp Phe Gln Ile Asp Val
            370                 375                 380

Ile Trp Lys Tyr Leu Thr Glu Val Pro Asp Gly Leu Thr Ser Ala Glu
385                 390                 395                 400

Met Lys Asp Ala Leu Leu Gln Val Asp Met Phe Gly Gly Glu Ile His
                405                 410                 415

Lys Val Val Trp Asp Ala Thr Ala Val Ala Gln Arg Glu Tyr Ile Ile
```

```
                  420              425              430
Lys Leu Gln Tyr Gln Thr Tyr Trp Gln Glu Glu Asp Lys Asp Ala Val
            435                  440                  445

Asn Leu Lys Trp Ile Arg Asp Phe Tyr Glu Glu Met Tyr Glu Pro Tyr
        450                  455                  460

Gly Gly Val Pro Asp Pro Asn Thr Gln Val Glu Ser Gly Lys Gly Val
465                 470                  475                  480

Phe Glu Gly Cys Tyr Phe Asn Tyr Pro Asp Val Asp Leu Asn Asn Trp
                    485                  490                  495

Lys Asn Gly Lys Tyr Gly Ala Leu Glu Leu Tyr Phe Leu Gly Asn Leu
                500                  505                  510

Asn Arg Leu Ile Lys Ala Lys Trp Leu Trp Asp Pro Asn Glu Ile Phe
            515                  520                  525

Thr Asn Lys Gln Ser Ile Pro Thr Lys Pro Leu Lys Glu Pro Lys Gln
        530                  535                  540

Thr Lys
545

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 32
accaagttta taaaaagcaa ccatcac                                        27

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 33
atgaattcgt gggtcgaaga gccc                                           24

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 34
caggaattca tatggctact cttccccaga aag                                 33

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Asp Pro Gly Tyr Ile Val Ile Asp Val Asn
  1               5                  10
```

```
<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Leu Gln Tyr Gln Thr Tyr Trp Gln Glu Glu
  1               5                  10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Tyr Leu Thr Glu Val Pro Asp Gly Leu Thr
  1               5                  10
```

RECOMBINANT HEXOSE OXIDASE, A METHOD OF PRODUCING SAME AND USE OF SUCH ENZYME

This application is a continuation of U.S. application Ser. No. 10/919,492, filed Aug. 17, 2004 now U.S. Pat. No. 7,544,795, which is a continuation of U.S. application Ser. No. 09/824,053, filed Apr. 3, 2001, now U.S. Pat. No. 6,924,366, which is a divisional of U.S. application Ser. No. 08/669,304, filed Sep. 11, 1996, now U.S. Pat. No. 6,251,626, which claims priority to PCT international application PCT/DK96/00238, which is a continuation-in-part of U.S. application Ser. No. 08/476,910, filed Jun. 7, 1995, each of which is incorporated by reference in its entirety.

FIELD OF INVENTION

The invention provides a method of producing hexose oxidase by recombinant DNA technology and such enzyme produced by the method and its use in the food industry and other fields.

TECHNICAL BACKGROUND AND PRIOR ART

Hexose oxidase (D-hexose:$O_2$-oxidoreductase, EC 1.1.3.5) is an enzyme which in the presence of oxygen is capable of oxidizing D-glucose and several other reducing sugars including maltose, lactose and cellobiose to their corresponding lactones with subsequent hydrolysis to the respective aldobionic acids. Accordingly, hexose oxidase differ from another oxido-reductase, glucose oxidase which can only convert D-glucose in that this enzyme can utilize a broader range of sugar substrates. The oxidation catalyzed by hexose oxidase can e.g. be illustrated as follows:

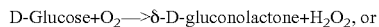

D-Glucose+$O_2$→δ-D-gluconolactone+$H_2O_2$, or

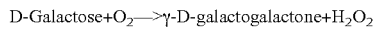

D-Galactose+$O_2$→γ-D-galactogalactone+$H_2O_2$

Up till now, hexose oxidase (in the following also referred to as HOX) has been provided by isolating the enzyme from several red algal species such as *Iridophycus flaccidum* (Bean and Hassid, 1956) and *Chondrus crispus* (Sullivan et al. 1973). Additionally, the algal species *Euthora cristata* has been shown to produce hexose oxidase.

It has been reported that hexose oxidase isolated from these natural sources may be of potential use in the manufacturing of certain food products. Thus, hexose oxidase isolated from *Iridophycus flaccidum* has been shown to be capable of converting lactose in milk with the production of the corresponding aldobionic acid and has been shown to be of potential interest as an acidifying agent in milk, e.g. to replace acidifying microbial cultures for that purpose (Rand, 1972). In that respect, hexose oxidase has been mentioned as a more interesting enzyme than glucose oxidase, since this latter enzyme can only be utilized in milk or food products not containing glucose with the concomitant addition of glucose or, in the case of a milk product, the lactose-degrading enzyme lactase, whereby the lactose is degraded to glucose and galactose. Even if glucose in this manner will become available as a substrate for the glucose oxidase, it is obvious that only 50% of the end products of lactase can be utilized as substrate by the glucose oxidase, and accordingly glucose oxidase is not an efficient acidifying agent in natural milk or dairy products.

The capability of oxygen oxidoreductases including that of hexose oxidase to generate hydrogen peroxide, which has an antimicrobial effect, has been utilized to improve the storage stability of certain food products including cheese, butter and fruit juice as it is disclosed in JP-B-73/016612. It has also been suggested that oxidoreductases may be potentially useful as oxygen scavengers or antioxidants in food products.

Within the bakery and milling industries it is known to use oxidizing agents such as e.g. iodates, peroxides, ascorbic acid, K-bromate or azodicarbonamide for improving the baking performance of flour to achieve a dough with improved stretchability and thus having a desirable strength and stability. The mechanism behind this effect of oxidizing agents is that the flour proteins, such as e.g. gluten in wheat flour contains thiol groups which, when they become oxidized, form disulphide bonds whereby the protein forms a more stable matrix resulting in a better dough quality and improvements of the volume and crumb structure of the baked products.

However, such use of several of the currently available oxidizing agents are objected to by consumers or is not permitted by regulatory bodies and accordingly, it has been attempted to find alternatives to these conventional flour and dough additives and the prior art has suggested the use of glucose oxidase for the above purpose. Thus, U.S. Pat. No. 2,783,150 discloses the addition of glucose oxidase to flour to improve the rheological characteristics of dough. CA 2,012,723 discloses bread improving agents comprising cellulolytic enzymes and glucose oxidase and JP-A-084848 suggests the use of a bread improving composition comprising glucose oxidase and lipase.

However, the use of glucose oxidase as a dough and bread improving additive has the limitation that this enzyme requires the presence of glucose as substrate in order to be effective in a dough system and generally, the glucose content in cereal flours is low. Thus, in wheat flour glucose is present in an amount which is in the range of 0-0.4% w/w, i.e. flours may not contain any glucose at all. Therefore, the absence or low content of glucose in doughs will be a limiting factor for the use of glucose oxidase as a dough improving agent. In contrast, the content of maltose is significantly higher already in the freshly prepared dough and further maltose is formed in the dough due to the activity of β-amylase either being inherently present in the flour or being added.

The current source of hexose oxidase is crude or partially purified enzyme preparations isolated by extraction from the above natively occurring marine algal species. However, since the amount of hexose oxidase in algae is low, it is evident that a production of the enzyme in this manner is too tedious and costly to warrant a cost effective commercial production of the enzyme from these natural sources. Furthermore, the provision of a sufficiently pure enzyme product at a cost effective level is not readily achievable in this manner.

A considerable industrial need therefore exists to provide an alternative and more cost effective source of this industrially valuable enzyme without being dependent on a natural source and also to provide the enzyme in a pure form, i.e. without any contaminating enzyme activities or any other undesirable contaminating substances including undesirable algal pigments and environmental pollutants which may be present in the marine areas where the hexose oxidase-producing algal species grow.

Furthermore, the industrial availability of a food grade quality of hexose oxidase in sufficient amounts and at cost effective prices will undoubtedly open up for new applications of that enzyme not only in the food industry, but also in other industrial areas as it will be discussed in the following. One example of such a novel application of the recombinant hexose oxidase in the food industry is the use hereof as a dough improving agent, another example being the use of hexose oxidase active polypeptide or a recombinant organism producing the polypeptide in the manufacturing of lactones.

SUMMARY OF THE INVENTION

The present invention has, by using recombinant DNA technology, for the first time made it possible to provide hexose oxidase active polypeptides in industrially appropriate quantities and at a quality and purity level which renders the hexose oxidase active polypeptide according to the invention highly suitable for any relevant industrial purpose including the manufacturing of food products and pharmaceuticals.

Accordingly, the invention pertains in a first aspect to a method of producing a polypeptide having hexose oxidase activity, comprising isolating or synthesizing a DNA fragment encoding the polypeptide, introducing said DNA fragment into an appropriate host organism in which the DNA fragment is combined with an appropriate expression signal for the DNA fragment, cultivating the host organism under conditions leading to expression of the hexose oxidase active polypeptide and recovering the polypeptide from the cultivation medium or from the host organism.

In a further aspect, the invention relates to a polypeptide in isolated form having hexose oxidase activity, comprising at least one amino acid sequence selected from the group consisting of (i)   Tyr-Glu-Pro-Tyr-Gly-Gly-Val-Pro,   (SEQ ID NO:1)

(ii)  Ala-Ile-Ile-Asn-Val-Thr-Gly-Leu-Val-Glu-Ser-Gly-Tyr-Asp-X-X-X-Gly-Tyr-X-Val-Ser-Ser,   (SEQ ID NO:2)

(iii) Asp-Leu-Pro-Met-Ser-Pro-Arg-Gly-Val-Ile-Ala-Ser-Asn-Leu-X-Phe,   (SEQ ID NO:3)

(iv)  Asp-Ser-Glu-Gly-Asn-Asp-Gly-Glu-Leu-Phe-X-Ala-His-Thr,   (SEQ ID NO:4)

(v)   Tyr-Tyr-Phe-Lys,   (SEQ ID NO:5)

(vi)  Asp-Pro-Gly-Tyr-Ile-Val-Ile-Asp-Val-Asn-Ala-Gly-Thr-X-Asp,   (SEQ ID NO:6)

(vii) Leu-Gln-Tyr-Gln-Thr-Tyr-Trp-Gln-Glu-Glu-Asp,   (SEQ ID NO:7)

(viii) X-Ile-Arg-Asp-Phe-Tyr-Glu-Glu-Met,   (SEQ ID NO:8)

where X represents an amino acid selected from the group consisting of Ala, Arg, Asn, Asp, Asx, Cys, Gln, Glu, Glx, Gly, His, Ile, Leu, Lys, Met, Phe, Pro, Ser, Thr, Trp, Tyr and Val, and muteins and variants hereof.

In still further aspects the invention relates to a recombinant DNA molecule comprising a DNA fragment coding for a polypeptide having hexose oxidase activity and to a microbial cell comprising such a recombinant DNA molecule.

In other aspects, the invention pertains to the use of the above hexose oxidase active polypeptide or a microbial cell expressing such a polypeptide in the manufacturing of a food product or an animal feed and the manufacturing of a pharmaceutical product, a cosmetic or a tooth care product.

In other useful aspects there is provided a method of reducing the sugar content of a food product, comprising adding to the food product an amount of the polypeptide or the microbial cell as disclosed herein, which is sufficient to remove at least part of the sugar initially present in said food product, a method of preparing a baked product from a dough, comprising adding the hexose oxidase active polypeptide or a microbial cell expressing such a polypeptide to the dough, and a dough improving composition comprising the polypeptide or the microbial cell according to the invention and at least one conventional dough component.

In another aspect, the invention relates to the use of the polypeptide or a microbial cell according to the invention as an analytical reagent for measuring the content of sugars.

In an interesting aspect, the invention also provides the use of a polypeptide or a microbial cell according to the invention in the manufacturing of a lactone, whereby the polypeptide and/or the microbial cell is applied to a reactor containing a carbohydrate which can be oxidized by the polypeptide and operating the reactor under conditions where the carbohydrate is oxidized.

DETAILED DISCLOSURE OF THE INVENTION

Hexose oxidases are produced naturally by several marine algal species. Such species are i.a. found in the family Gigartinaceae which belong to the order Gigartinales. Examples of hexose oxidase producing algal species belonging to Gigartinaceae are *Chondrus crispus* and *Iridophycus flaccidum*. Also algal species of the order Cryptomeniales including the species *Euthora cristata* are potential sources of the hexose oxidase active polypeptide according to the invention. Accordingly, such algal species are potentially useful sources of hexose oxidase and of DNA coding for such hexose oxidase active polypeptides. As used herein the term "hexose oxidase active polypeptide" denotes an enzyme which at least oxidizes D-glucose, D-galactose, D-mannose, maltose, lactose and cellobiose.

When using such natural sources for the isolation of native hexose oxidase, as it has been done in the prior art and in the present invention with the purpose of identifying algal material which could be used as a source of mRNA for use in the construction of cDNA and as the starting point for constructing primers of synthetic DNA oligonucleotides, the enzyme is typically isolated from the algal starting material by extraction using an aqueous extraction medium.

As starting material for such an extraction the algae may be used in their fresh state as harvested from the marine area of growth or they may be used after drying the fronds e.g. by air-drying at ambient temperatures or by any appropriate industrial drying method such as drying in circulated heated air or by freeze-drying. In order to facilitate the subsequent extraction step, the fresh or dried starting material may be comminuted e.g. by grinding or blending.

As the aqueous extraction medium, buffer solutions having a pH in the range of 6-8, such as 0.1 M sodium phosphate buffer, 20 mM triethanolamine buffer or 20 mM Tris-HCl buffer are suitable. The hexose oxidase is typically extracted from the algal material by suspending the starting material in the buffer and keeping the suspension at a temperature in the range of 0-20° C. such as at about 5° C. for 1 to 10 days, preferably under agitation.

The suspended algal material is then separated from the aqueous medium by an appropriate separation method such as filtration, sieving or centrifugation and the hexose oxidase subsequently recovered from the filtrate or supernatant. Optionally, the separated algal material is subjected to one or more further extraction steps.

Since several marine algae contain coloured pigments such as phycocyanins, it may be required to subject the filtrate or supernatant to a further purification step whereby these pigments are removed. As an example, the pigments may be removed by treating the filtrate or supernatant with an organic solvent in which the pigments are soluble and subsequently separating the solvent containing the dissolved pigments from the aqueous medium.

The recovery of hexose oxidase from the aqueous extraction medium can be carried out by any suitable conventional methods allowing isolation of proteins from aqueous media. Such methods, examples of which will be described in details in the following, include such methods as ion exchange chromatography, optionally followed by a concentration step such as ultrafiltration. It is also possible to recover the enzyme by adding substances such as e.g. $(NH_4)_2SO_4$ which causes the protein to precipitate, followed by separating the precipitate and optionally subjecting it to conditions allowing the protein to dissolve.

For the purpose of the invention it is desirable to provide the enzyme in a substantially pure form e.g. as a preparation essentially without other proteins or non-protein contaminants and accordingly, the relatively crude enzyme preparation resulting from the above extraction and isolation steps is preferably subjected to further purification steps such as further chromatography steps, gel filtration or chromatofocusing as it will also be described by way of example in the following.

As it is mentioned above, the hexose oxidase active polypeptide according to invention is provided by means of recombinant DNA technology methods allowing it to be produced by cultivating in a culturing medium an appropriate host organism cell comprising a gene coding for the hexose oxidase, and recovering the enzyme from the cells and/or the culturing medium.

The method of producing hexose oxidase which is provided herein comprises as a first step the isolation or the construction of a DNA fragment coding for hexose oxidase. Several strategies for providing such a DNA fragment are available. Thus, the DNA fragment can be isolated as such from an organism which inherently produces hexose oxidase. In order to identify the location of the coding DNA fragment, it is required to dispose of RNA or DNA probe sequences which under appropriate conditions will hybridize to the DNA fragment searched for and subsequently isolating a DNA fragment comprising the coding sequence and cloning it in a suitable cloning vector.

Another suitable strategy, which is disclosed in details in the below examples, is to isolate mRNA from an organism producing the hexose oxidase and use such mRNA as the starting point for the construction of a cDNA library which can then be used for polymerase chain reaction (PCR) synthesis of DNA based on oligonucleotide primers which are synthesized based on amino acid sequences of the hexose oxidase. It was found that such a strategy is suitable for providing a hexose oxidase-encoding DNA fragment. By way of example such a strategy as described in details below is described summarily.

Synthetic oligonucleotides were prepared based on the HOX-2 and HOX-3 peptide sequences prepared as described hereinbelow by endoLys-C digestion of a 40 kD polypeptide of hexose oxidase extracted from *Chondrus crispus*. PCR using first strand cDNA as template and with a sense HOX-2 primer and an anti-sense HOX-3 primer produced a DNA fragment of 407 bp. This fragment was inserted into an *E. coli* vector, pT7 Blue and subsequently sequenced. It was found that in addition to the sequences for the HOX-2 and HOX-3 peptides this 407 bp fragment also contained an open reading frame containing the HOX-4 and HOX-5 peptides of the above 40 kD *Chondrus crispus*-derived hexose oxidase fragment the isolation of which is also described in the following.

Sense and anti-sense oligonucleotides were synthesized based on the 407 bp fragment, and two fragments of 800 and 1400 bp, respectively could subsequently be isolated by PCR using cDNA as template. These two fragments were cloned in the pT7 Blue vector and subsequently sequenced. The DNA sequence of the 5'-fragment showed an open reading frame containing the HOX-6 peptide which was also isolated from the above 40 kD *Chondrus crispus*-derived hexose oxidase fragment. Similarly, the 3'-fragment showed a reading frame containing the HOX-1, the isolation of which is disclosed below, and the HOX-7 and HOX-8, both isolated from a 29 kD *Chondrus crispus*-derived hexose oxidase polypeptide obtained by endoLys-C digestion as also described in the following.

Based upon the combined DNA sequences as mentioned above, an oligonucleotide corresponding to the 5'-end of the presumed box gene and an oligonucleotide corresponding to the 3'-end of that gene were synthesized. These two oligonucleotides were used in PCR using first strand cDNA as template resulting in a DNA fragment of about 1.8 kb. This fragment was cloned in the above *E. coli* vector and sequenced. The DNA sequence was identical to the combined sequence of the above 5'-end, 407 bp and 3'-end sequences and it was concluded that this about 1.9 kb DNA sequence codes for both the 40 kD and the 29 kD *Chondrus crispus*-derived hexose oxidase fragments.

As will be evident for the skilled artisan, the above strategy for isolating a DNA fragment encoding a hexose oxidase active polypeptide, including the isolation and characterization of the hexose oxidase, can be used for the construction of such fragments encoding hexose oxidases derived from any other natural source than *Chondrus crispus* including the marine algal species mentioned above, such as from other plants or from a microorganism.

Alternatively, the DNA sequence of the hexose oxidase active polypeptide-encoding DNA fragment may be constructed synthetically by established standard methods e.g. the phosphoamidite method described by Beaucage and Caruthers (1981), or the method described by Matthes et al. (1984). According to the phosphoamidite method, oligonucleotides are synthesized, eg in an automatic DNA synthesizer, purified, annealed, ligated and cloned in an appropriate vector.

Furthermore, the DNA fragment may be of mixed genomic and synthetic, mixed synthetic and cDNA or mixed genomic and cDNA origin, prepared by ligating sub-fragments of synthetic, genomic or cDNA origin as appropriate, the sub-fragments corresponding to various parts of the entire DNA fragment, in accordance with standard techniques.

In a subsequent step of the method according to the invention, the isolated or synthesized hexose oxidase active polypeptide-encoding DNA fragment is introduced into an appropriate host organism in which the DNA fragment is combined operably with an appropriate expression signal for the DNA fragment. Such an introduction can be carried out by methods which are well-known to the skilled practitioner including the construction of a vector having the fragment inserted and transforming the host organism with the vector. Suitable vectors include plasmids which are capable of replication in the selected host organism. It is also contemplated that the DNA fragment can be integrated into the chromosome of the host organism e.g. by inserting the fragment into a transposable element such as a transposon, and subjecting a mixture of the selected host organism and the transposon to conditions where the transposon will become integrated into the host organism chromosome and combine with an appropriate expression signal.

According to the invention, a hexose oxidase active polypeptide-encoding DNA fragment including the gene for the polypeptide, which is produced by methods as described above, or any alternative methods known in the art, can be expressed in enzymatically active form using an expression vector. An expression vector usually includes the components of a typical cloning vector, i.e. an element that permits autonomous replication of the vector in the selected host organism and one or more phenotypic markers for selection purposes. An expression vector includes control sequences encoding a promoter, operator, ribosome binding site, translation initiation signal and optionally, a repressor gene or one or more activator genes. To permit the secretion of the expressed polypeptide, a signal sequence may be inserted upstream of the coding sequence of the gene. In the present context, the term "expression signal" includes any of the above control sequences, repressor or activator sequences and signal sequence. For expression under the direction of control sequences, the hexose oxidase encoding gene is operably linked to the control sequences in proper manner with respect to expression. Promoter sequences that can be incorporated into plasmid vectors, and which can support the transcription of the hexose oxidase gene include, but are not limited to the tac promoter, phage lambda-derived promoters including the $P_L$ and $P_R$ promoters.

An expression vector carrying the DNA fragment of the invention may be any vector which is capable of expressing the hexose oxidase gene in the selected host organism, and the choice of vector will depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, a minichromosome or an artificial chromosome. Alternatively, the vector may be one which, when introduced into a host cell, is integrated into the host cell genome and replicated together with the chromosome.

In the vector, the DNA fragment coding for the hexose oxidase active polypeptide should be operably combined with a suitable promoter sequence. The promoter may be any DNA sequence which confers transcriptional activity to the host organism of choice and may be derived from genes encoding proteins which are either homologous or heterologous to the host organism. Examples of suitable promoters for directing the transcription of the DNA fragment of the invention in a bacterial host are the promoter of the lac operon of *E. coli*, the *Streptonyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes.

For transcription in a fungal species, examples of useful promoters are those derived from the genes encoding the *Pichia pastoris* alcohol oxidase, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase. As examples of suitable promoters for expression in a yeast species the Gal 1 and Gal 10 promoters of *Saccharomyces cerevisiae* can be mentioned. When expressed in a bacterial species such as *E. coli*, a suitable promoter may be selected from a bacteriophage promoter including a T7 promoter or a lambda bacteriophage promoter.

The vector comprising the DNA fragment encoding the hexose oxidase active polypeptide may also comprise a selectable marker, e.g. a gene the product of which complements a defect in the host organism such as a mutation conferring an auxotrophic phenotype, or the marker may be one which confers antibiotic resistance or resistance to heavy metal ions.

The host organism of the invention either comprising a DNA construct or an expression vector as described above is advantageously used as a host cell in the recombinant production of a polypeptide according to the invention. The cell may be transformed with a DNA construct comprising the gene coding for the polypeptide of the invention or, conveniently by integrating the DNA construct into the host chromosome. Such an integration is generally considered to be advantageous as the DNA fragment is more likely to be stably maintained in the cell. Integration of the DNA constructs into the host chromosome may be carried out according to conventional methods such as e.g. by homologous or heterologous recombination or by means of a transposable element. Alternatively, the host organism may be transformed with an expression vector as described above.

In accordance with the invention, the host organism may be a cell of a higher organism such as an animal cell, including a mammal, an avian or an insect cell, or a plant cell. However, in preferred embodiments, the host organism is a microbial cell, e.g. a bacterial or a fungal cell including a yeast cell.

Examples of suitable bacterial host organisms are gram positive bacterial species such as *Bacillaceae* including *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium* and *Bacillus thuringiensis*, *Streptomyces* species such as *Streptomyces murinus*, lactic acid bacterial species including *Lactococcus* spp. such as *Lactococcus lactis*, *Lactobacillus* spp. including *Lactobacillus reuteri*, *Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A yeast host organism may advantageously be selected from a species of *Saccharomyces* including *Saccharomyces cerevisiae* or a species belonging to Schizosaccharomyces. Suitable host organisms among filamentous fungi include species of *Aspergillus*, eg *Aspergillus oryzae*, *Aspergillus nidulans* or *Aspergillus niger*. Alternatively, strains of a *Fusarium* species, eg *Fusarium oxysporum* or of a *Rhizomucor* species such as *Rhizomucor miehei* can be used as the host organism. In one preferred embodiment a strain of the species *Pichia pastoris* is used as host organism.

Some of the above useful host organisms such as fungal species or gram positive bacterial species may be transformed by a process which include protoplast formation and transformation of the protoplasts followed by regeneration of the cell wall in a manner known per se.

For the production of the hexose oxidase active polypeptide, the recombinant host organism cells as described above are cultivated under conditions which lead to expression of the polypeptide in a recoverable form. The medium used to cultivate the cells may be any conventional medium suitable for growing the host cells in question and obtaining expression of the polypeptide. Suitable media are available from commercial suppliers or may be prepared according to published recipes.

The resulting polypeptide is typically recovered from the cultivation medium by conventional procedures including separating the cells from the medium by centrifugation or filtration, if necessary, after disruption of the cells, followed by precipitating the proteinaceous components of the supernatant or filtrate e.g. by adding a salt such as ammonium sulphate, followed by a purification step.

It is an industrially convenient aspect of the invention that microbial cultures such as e.g. bacterial cultures which are used in the manufacturing of food or feed products can be used as the host organism expressing the gene coding for the hexose oxidase active polypeptide. Thus, lactic acid bacterial starter cultures which are used in the manufacturing of dairy products or other food products such as meat product or wine and which e.g. comprise one or more strains of a lactic acid bacterium selected from any of the above lactic acid bacterial species can be used as host organisms whereby the hexose oxidase will be produced directly in the food product to which the starter cultures are added.

Similarly, the hexose oxidase encoding gene according to the invention may be introduced into lactic acid bacterial starter cultures which are used as inoculants added to fodder crops such as grass or corn or to proteinaceous waste products of animal origin such as fish and slaughterhouse waste materials for the production of silage for feeding of animals. For this purpose, the expression of hexose oxidase by the silage inoculants will imply that the oxygen initially present in the crops or the waste materials to be ensiled is depleted whereby anaerobic conditions, which will inhibit growth of aerobic spoilage organisms such as gram negative bacteria and yeasts, will be established.

It is also contemplated that yeast cultures such as baker's yeast or yeast cultures which are used in the manufacturing of alcoholic beverages including wine and beer can be used as host organisms for the gene coding for the hexose oxidase active polypeptide of the invention. For example in the case of such recombinant baker's yeast strains, the hexose oxidase being produced will have a dough improving effect as it is described in the following.

From the above it is apparent that the direct addition of recombinant microbial cultures expressing the hexose oxidase according to the invention to a food product or any other product where hexose oxidase activity is desired, can be used as an alternative to the addition of the isolated enzyme.

In further industrially important embodiments, the recombinant microbial cultures expressing a hexose oxidase active polypeptide are used in a bioreactor for the production of the enzyme or for the production of lactones from either of the above-mentioned carbohydrates which can be oxidized by the hexose oxidase active enzyme. For this latter application, the cells of the microbial cultures are advantageously immobilized on a solid support such as a polymer material, which is preferable in the form of small particles to provide a large surface for binding the cells. Alternatively, the isolated enzyme may be used for the above purpose, also preferable bound to a solid support material. In this connection, the binding of the cells or the enzyme may be provided by any conventional method for that purpose.

In other useful embodiments of the invention, the polypeptide having hexose oxidase activity may be a fusion product, i.e. a polypeptide which in addition to the hexose oxidase active amino acid sequences comprises further amino acid sequences having other useful activities. Thus, fusion polypeptides having one or more enzyme activities in addition to the hexose oxidase activity are contemplated. Such additional enzyme activities may be chosen among enzymes capable of degrading carbohydrates, such as lactase, amylases including glucoamylases, glucanases, cellulases, hemicellulases, xylanases, lactases or any other oxidoreductase such as glucose oxidase, galactose oxidase or pyranose oxidase, and also among proteases and peptidases, lipases or nucleases. The additional enzyme sequence(s) to be chosen for integration into a hexose oxidase polypeptide according to the invention depend(s) on the product for which the enzymatically active fusion product is intended. Thus, as examples, it is contemplated that a hexose oxidase active fusion polypeptide for use in the manufacturing of a dairy product advantageously comprises a lactase, a protease or a peptidase, and that a fusion polypeptide intended for dough improvement may as the fusion partner comprise any of the above carbohydrate degrading enzymes. It is also apparent that microbial cells according to the invention as described above and which express a hexose oxidase active fusion polypeptide having additional enzyme activities may be used for inoculation of other food products and animal feeds in the manner as also described above.

It is also contemplated that a suitable fusion partner may be a sequence conferring to the hexose oxidase altered characteristics such as solubility or a sequence which can serve as a "tagging" group conferring to the hexose oxidase the ability to bind more strongly or more selectively to a particular solid material for hexose oxidase polypeptide purification or immobilization purposes.

Furthermore, it is within the scope of the invention to provide the polypeptide as a chimeric product comprising partial sequences of hexose oxidase active polypeptides derived from different sources and being encoded by a DNA fragment which is constructed by combining hexose oxidase active polypeptide-encoding DNA sequences from these different sources into one DNA fragment encoding the entire chimeric polypeptide.

In one useful embodiment the method according to the invention is one wherein the DNA fragment encoding the hexose oxidase active polypeptide comprises at least one DNA sequence coding for an amino acid sequence selected from the group consisting of (i)    Tyr-Glu-Pro-Tyr-Gly-Gly-Val-Pro, (SEQ ID NO:1)

(ii)   Ala-Ile-Ile-Asn-Val-Thr-Gly-Leu-Val-Glu-Ser-Gly-Tyr-Asp-X-X-X-Gly-Tyr-X-Val-Ser-Ser, (SEQ ID NO:2)

(iii)  Asp-Leu-Pro-Met-Ser-Pro-Arg-Gly-Val-Ile-Ala-Ser-Asn-Leu-X-Phe, (SEQ ID NO:3)

(iv)   Asp-Ser-Glu-Gly-Asn-Asp-Gly-Glu-Leu-Phe-X-Ala-His-Thr, (SEQ ID NO:4)

(v)    Tyr-Tyr-Phe-Lys, (SEQ ID NO:5)

(vi)   Asp-Pro-Gly-Tyr-Ile-Val-Ile-Asp-Val-Asn-Ala-Gly-Thr-X-Asp, (SEQ ID NO:6)

-continued (vii) Leu-Gln-Tyr-Gln-Thr-Tyr-Trp-Gln-Glu-Glu-Asp, (SEQ ID NO:7)

(viii) X-Ile-Arg-Asp-Phe-Tyr-Glu-Glu-Met, (SEQ ID NO:8)

where X represents an amino acid selected from the group consisting of Ala, Arg, Asn, Asp, Asx, Cys, Gln, Glu, Glx, Gly, His, Ile, Leu, Lys, Met, Phe, Pro, Ser, Thr, Trp, Tyr and Val, and muteins and variants hereof.

In the present context, the term "variant" is used to designate any modification of a hexose oxidase active polypeptide sequence which does not result in complete loss of the hexose oxidase activity. The modifications may include deletion, substitution of amino acid residues present in the polypeptide as it is derived from a natural source or in an already modified polypeptide sequence or the modification may imply the insertion into such a polypeptide of additional amino acid residues. Substitution of one or more amino acid residues may be carried out by modifying or substituting the codon or codons coding for the amino acid or amino acids which it is desired to substitute, e.g. by mutagenesis, in particular site-directed mutagenesis, using methods which are known per se. Similarly, deletion of one or more amino acid residues can be made by deleting the corresponding codon or codons in the DNA fragment coding for the polypeptide according to the invention.

As also mentioned above, the method according to the invention may as a further step include a purification of the polypeptide preparation initially recovered from the cultivation medium and/or the microorganisms. The purpose of this further step is to obtain an enzyme preparation in which the hexose oxidase polypeptide is in a substantially pure form. The term "substantially pure form" implies that the preparation is without any undesired contaminating substances originating from the cultivation medium, the production host organism cells or substances produced by these cells during cultivation. Thus, it is for many applications of importance that the polypeptide preparation resulting from the purification step is substantially without any non-hexose oxidase enzymatic activity. The purification methods will depend on the degree of purity which is desirable, but will typically be selected from conventional protein purification methods such as salting out, affinity or ion exchange chromatography procedures including hydrophobic interaction chromatography, and gel filtration methods, such as the method described in the following examples.

As mentioned above, the invention relates in a further aspect to a polypeptide in isolated form having hexose oxidase activity, comprising at least one of the above amino acid sequences, or muteins and variants hereof as they are described above. Preferably, the polypeptide is produced according to the methods as described above.

Depending on the method of production, in particular the host organism in question, the polypeptide according to the invention may be glycosylated to a varying degree or it may for certain purposes advantageously be expressed in a substantially non-glycosylated form.

In one preferred embodiment of the invention, the polypeptide is one which has functional characteristics identical or partially identical to those of hexose oxidase naturally occurring in the algal species *Chondrus crispus* as they are described in the prior art. It was found that such a hexose oxidase extracted from the algal source when it was subjected to SDS-PAGE as described herein may show separate protein bands of 29, 40 and/or 60 kD.

In order to obtain a generally cost effective use of the polypeptide, it is preferred that the enzyme has a high enzymatic activity over a broad pH range. Thus, it is preferred that the hexose oxidase according to the invention at least shows an enzymatic activity at a pH in the range of 1-9, such as in the range of 2-9 including the range of 5-9. In this connection it is contemplated that the pH range of activity or the pH optimum of a naturally derived hexose oxidase may be modified in a desired direction and to a desired degree by modifying the enzyme as described above or by random mutagenesis of a replicon or a host organism comprising the DNA coding for the hexose oxidase, followed by selection of mutants having the desired altered pH characteristics. Alternatively, such modifications of the enzyme may be aimed at modifying the thermotolerance and optimum temperature for activity of the hexose oxidase active polypeptide, or at changing the isoelectric point of the enzyme.

Furthermore, the polypeptide according to the invention is preferably enzymatically active within a broad temperature range such as a range of 10-90° C., e.g. within a range of 15-80° C. including the range of 20-60° C. In particular, it may for certain specific purposes be preferred that the hexose oxidase active polypeptide maintains a significant residual enzymatic activity at temperatures of 70° C. or higher, e.g. when the enzyme is intended for use in doughs where it may be useful to have hexose oxidase activity during at least part of the subsequent baking step.

The scope of application of the hexose oxidase depends on the range of carbohydrates which they can use as substrate. Although the hexose oxidase appear to have highest substrate specificity for hexoses, such as glucose, galactose and mannose, it has been found that the range of carbohydrate substances which can be utilized as substrates for the polypeptide according to the invention is not limited to hexoses. Thus, a preferred polypeptide is one which in addition to a high specificity for hexoses also has a high specificity for other carbohydrate substances including disaccharides such as lactose, maltose and/or cellobiose and even also substantial specificity to pentoses including as an example xylose, or deoxypentoses or deoxyhexoses such as rhamnose or fucose. It is of significant practical implication that the hexose oxidase in addition to a high specificity to hexoses and other monosaccharides also has substantial specificity for disaccharides, in particular lactose present in milk and maltose which i.a. occurs in cereal flours and doughs.

Accordingly, in another preferred embodiment the polypeptide according to the invention is one which in addition to D-glucose oxidizes at least one sugar selected from the group consisting of D-galactose, maltose, cellobiose, lactose, D-mannose, D-fucose and D-xylose.

In still another preferred embodiment the hexose oxidase active polypeptide has an isoelectric point in the range of 4-5. Specifically, the polypeptide may preferably have an isoelectric point of 4.3±0.1 or one of 4.5±0.1.

Generally, the polypeptide according to the invention typically has a molecular weight as determined by gel filtration using Sephacryl S-200 Superfine (Pharmacia) which is in the range of 100-150 kD, A molecular weight determined by this or equivalent methods are also referred to as an apparent molecular weight. Specifically, the polypeptide may have an apparent molecular weight of 110 kD±10 kD.

In a still further aspect, the invention provides a recombinant DNA molecule comprising a DNA fragment coding for a polypeptide having hexose oxidase activity. As it has been described above, such a DNA fragment may be isolated from a natural source or it may be constructed e.g. as it is described in details in the below examples. Furthermore, the coding fragment may also be synthesized based upon amino acid sequences of a naturally occurring hexose oxidase. The recombinant molecule can be selected from any of the expression vector types as mentioned above. In preferred embodiments, the recombinant DNA molecule comprises a DNA fragment coding for a hexose oxidase polypeptide which comprises at least one of the above amino acid sequences (i) to (viii), or a mutein or derivative of such polypeptide. In one specific embodiment, the recombinant DNA molecule comprises the following DNA sequence (SEQ ID NO:30):

Furthermore, the invention provides in another aspect a microbial cell which comprises the above recombinant DNA molecule. The above general description of the host organism comprising a DNA fragment encoding the polypeptide according to the invention encompasses such a microbial cell and accordingly, such cells can be selected from any of the above mentioned microbial groups, families, genera and species, i.e. the microbial cell may be selected from a bacterial cell, a fungal cell and a yeast cell including as examples an *E. coli* cell, a lactic acid bacterial cell, a *Saccharomyces cerevisiae* cell and a *Pichia pastoris* cell.

The microbial cell according to the invention may, if it is intended for direct addition to a product where it is desired to

```
TGAATTCGTG GGTCGAAGAG CCCTTTGCCT CGTCTCTCTG GTACCGTGTA TGTCAAAGGT      60
TCGCTTGCAC ACTGAACTTC ACGATGGCTA CTCTTCCTCA GAAAGACCCC GGTTATATTG     120
TAATTGATGT CAACGCGGGC ACCGCGGACA AGCCGGACCC ACGTCTCCCC TCCATGAAGC     180
AGGGCTTCAA CCGCCGCTGG ATTGGAACTA ATATCGATTT CGTTTATGTC GTGTACACTC     240
CTCAAGGTGC TTGTACTGCA CTTGACCGTG CTATGGAAAA GTGTTCTCCC GGTACAGTCA     300
GGATCGTCTC TGGCGGCCAT TGCTACGAGG ACTTCGTATT TGACGAATGC GTCAAGGCCA     360
TCATCAACGT CACTGGTCTC GTTGAGAGTG GTTATGACGA CGATAGGGGT TACTTCGTCA     420
GCAGTGGAGA TACAAATTGG GGCTCCTTCA AGACCTTGTT CAGAGACCAC GGAAGAGTTC     480
TTCCCGGGGG TTCCTGCTAC TCCGTCGGCC TCGGTGGCCA CATTGTCGGC GGAGGTGACG     540
GCATTTTGGC CCGCTTGCAT GGCCTCCCCG TCGATTGGCT CAGCGGCGTG GAGGTCGTCG     600
TTAAGCCAGT CCTCACCGAA GACTCGGTAC TCAAGTATGT GCACAAAGAT TCCGAAGGCA     660
ACGACGGGGA GCTCTTTTGG GCACACACAG GTGGCGGTGG CGGAAACTTT GGAATCATCA     720
CCAAATACTA CTTCAAGGAT TTGCCCATGT CTCCACGGGG CGTCATCGCA TCAAATTTAC     780
ACTTCAGCTG GACGGTTTC ACGAGAGATG CCTTGCAGGA TTTGTTGACA AAGTACTTCA     840
AACTTGCCAG ATGTGATTGG AAGAATACGG TTGGCAAGTT TCAAATCTTC CATCAGGCAG     900
CGGAAGAGTT TGTCATGTAC TTGTATACAT CCTACTCGAA CGACGCCGAG CGCGAAGTTG     960
CCCAAGACCG TCACTATCAT TTGGAGGCTG ACATAGAACA GATCTACAAA ACATGCGAGC    1020
CCACCAAAGC GCTTGGCGGG CATGCTGGGT GGGCGCCGTT CCCCGTGCGG CCGCGCAAGA    1080
GGCACACATC CAAGACGTCG TATATGCATG ACGAGACGAT GGACTACCCC TTCTACGCGC    1140
TCACTGAGAC GATCAACGGC TCCGGGCCGA ATCAGCGCGG CAAGTACAAG TCTGCGTACA    1200
TGATCAAGGA TTTCCCGGAT TTCCAGATCG ACGTGATCTG GAAATACCTT ACGGAGGTCC    1260
CGGACGGCTT GACTAGTGCC GAAATGAAGG ATGCCTTACT CCAGGTGGAC ATGTTTGGTG    1320
GTGAGATTCA CAAGGTGGTC TGGGATGCGA CGGCAGTCGC GCAGCGCGAG TACATCATCA    1380
AACTGCAGTA CCAGACATAC TGGCAGGAAG AAGACAAGGA TGCAGTGAAC CTCAAGTGGA    1440
TTAGAGACTT TTACGAGGAG ATGTATGAGC CGTATGGCGG GGTTCCAGAC CCCAACACGC    1500
AGGTGGAGAG TGGTAAAGGT GTGTTTGAGG GATGCTACTT CAACTACCCG GATGTGGACT    1560
TGAACAACTG GAAGAACGGC AAGTATGGTG CCCTCGAACT TTACTTTTTG GGTAACCTGA    1620
ACCGCCTCAT CAAGGCCAAA TGGTTGTGGG ATCCCAACGA GATCTTCACA AACAAACAGA    1680
GCATCCCTAC TAAACCTCTT AAGGAGCCCA AGCAGACGAA ATAGTAGGTC ACAATTAGTC    1740
ATCGACTGAA GTGCAGCACT TGTCGGATAC GGCGTGATGG TTGCTTTTTA TAAACTTGGT    1800
                                                                   1801
```

A have hexose oxidase activity, e.g. during a manufacturing process, be provided in the form of a microbial culture, preferable in a concentrate form. Thus, such a culture may advantageously contain the microbial cell according to the invention in a concentration which is preferably in the range of $10^5$ to $10^{12}$ per g of culture. The culture may be a fresh culture, i.e. a non-frozen suspension of the cells in a liquid medium or it may be in the form of a frozen or dried culture, e.g. a freeze-dried culture. The microbial cell may also for specific purposes be immobilized on a solid substrate.

As mentioned above, the invention relates in another further aspect to the use of the hexose oxidase active polypeptide according to the invention or of a microbial cell expressing such a polypeptide in the manufacturing of food products. In this context the term "manufacturing" should be understood in its broadest sense so as to encompass addition of the hexose oxidase or the microbial cell to ingredients for the food product in question, prior to, during or after any subsequent process step, during packaging and during storage of the finished product up till it is consumed. The food products where such use is advantageous may be any product where the end products of the hexose oxidase confer advantageous effects on the food product.

Naturally, the desired activity of the hexose oxidase will only be obtained if substrate for the enzyme is present in sufficient amounts. The substrate carbohydrates may be inherently present in the food product or the ingredients herefor or they may be added or generated during the manufacturing process. An example of substrate being generated during manufacturing is the enzymatic degradation of di-, oligo- or polysaccharides to lower sugar substances which is degradable by the hexose oxidase which may occur as the result of enzymatic activity of enzymes inherently present in the food product or added during the manufacturing. Furthermore, substrate for the hexose oxidase active polypeptide may be generated as the result of the enzymatic activity of a fusion partner as described above.

The desirable effects of hexose oxidase activity in a product containing substrates for the enzyme include generation of lactones from the sugar substrate which may subsequently be converted to corresponding acids, generation of hydrogen peroxide and consumption of oxygen.

Typical examples of food products where hexose oxidase activity may be advantageous include as examples dairy products, starch-containing food products and non-dairy beverages. Thus, in the manufacturing of a range of dairy products it is desired to lower the pH. This is conventionally obtained by inoculating the milk with lactic acid-producing starter cultures. As mentioned above, it is contemplated that hexose oxidase or organisms expressing this enzyme may be used as an alternative means of acidifying milk. The same effect may be desirable in other food products which are acidified during manufacturing such as certain meat products or vegetable product which are currently acidified by the addition of lactic acid bacterial starter cultures.

The consumption of oxygen resulting from the activity of the hexose oxidase has several advantageous implications in relation to the manufacturing of food products and pharmaceuticals. By causing depletion or removal of oxygen in foods or pharmaceuticals containing lipids which are prone to oxidative spoilage processes, the hexose oxidase may act as an antioxidant and additionally, the reduction of oxygen content may inhibit spoilage organisms the growth of which is dependent on presence of oxygen and accordingly, the hexose oxidase active polypeptide may also act as an antimicrobial agent.

This latter effect can be utilized to extend the shelf life of packaged foods where spoilage can be prevented by the incorporation of the hexose oxidase active polypeptide according to the invention either in the food product itself or by providing a mixture of the hexose oxidase and an appropriate substrate herefor in the packaging, but separate from the content of food product. In a typical example, such a mixture is attached to the inner side of a food container such as eg a tin or a jar. Accordingly, the hexose oxidase according to the invention can be used as an oxygen removing agent in a food packaging.

It is evident that the above effects of the polypeptide according to the invention in the manufacturing of food products will also be applicable in the manufacturing of animal feed products. In particular, these effects are desirable in the making of silage either made from fodder crops such as grass or corn or from proteinaceous animal waste products from slaughterhouses or fish processing plants. Such feed products are currently ensiled by the addition of acids or acid producing bacteria such as lactic acid bacterial inoculants. In order to promote growth of acidifying bacteria and to prevent the growth of aerobic spoilage organisms such as gram negative bacteria and yeasts it is essential to have a low oxygen content in the silage material. It is therefore contemplated that the hexose oxidase according to the invention is useful as oxygen removing and acidifying agent in the ensiling of feeds, optionally in the form of compositions further comprising one or more conventional silage additive such as lactic acid bacterial inoculants or enzymes which generate low molecular sugar substances.

A further useful application of the hexose oxidase polypeptide according to the invention is the use of the enzyme to reduce the sugar content of a food product, comprising adding to the product an amount of the polypeptide or a microbial cell producing the polypeptide which is sufficient to remove at least part of the sugar initially present in the food product. Such an application may e.g. be useful in the manufacturing of diets for diabetic patients where a low sugar content is desired, and in the production of wines with a reduced alcohol content. In this latter application, the hexose oxidase is preferably added to the must prior to yeast inoculation.

In a further useful aspect, the invention relates to the use of the hexose oxidase active polypeptide or of a microbial cell producing the enzyme according to the invention in the manufacturing of pharmaceutical products, cosmetics or tooth care products such as tooth pastes or dentrifices. The desired effects of the hexose oxidase in such products are essentially those described above with respect to food products and animal feeds.

One particularly interesting use of the hexose oxidase according to the invention is its use as a dough improving agent. It has been found that the addition of the hexose oxidase to a dough results in an increased resistance hereof to breaking when the dough is stretched, i.e. the enzyme confers to the dough an increased strength whereby it becomes less prone to mechanical deformation. It is, based on the known effects in this regard for glucose oxidase, contemplated that this effect of addition of the hexose oxidase according to the invention to a dough is the result of the formation of crosslinks between thiol groups in sulphur-containing amino acids in flour proteins which occurs when the hydrogen peroxide generated by the enzyme in the dough reacts with the thiol groups which are hereby oxidized.

Accordingly, the invention also provides a method of preparing a baked product from a dough, comprising adding to the dough an effective amount of the polypeptide or a microorganism according to the invention which is capable of expressing such a polypeptide, and a dough improving composition comprising the polypeptide or a microorganism capable of expressing such a polypeptide in a dough, and at least one conventional dough component. In useful embodiments such a composition may further comprise at least one dough or bakery product improving enzyme e.g. selected from a cellulase, a hemicellulase, a pentosanase, a lipase, a xylanase, an amylase, a glucose oxidase and a protease.

In still further aspects of the invention, the hexose oxidase is used as an analytical reagent in methods of determining in a biological and other samples the concentration of any sugar which can be converted by the enzyme. Typically, the sugar content is measured by determining the amount of end products resulting from the enzymatic conversion of the substrate sugar present in the sample to be measured. In this connection, it is contemplated that the hexose oxidase can be used directly as a reagent in an in vitro analytical assay or that it can be incorporated in a sensor.

Figure 2:
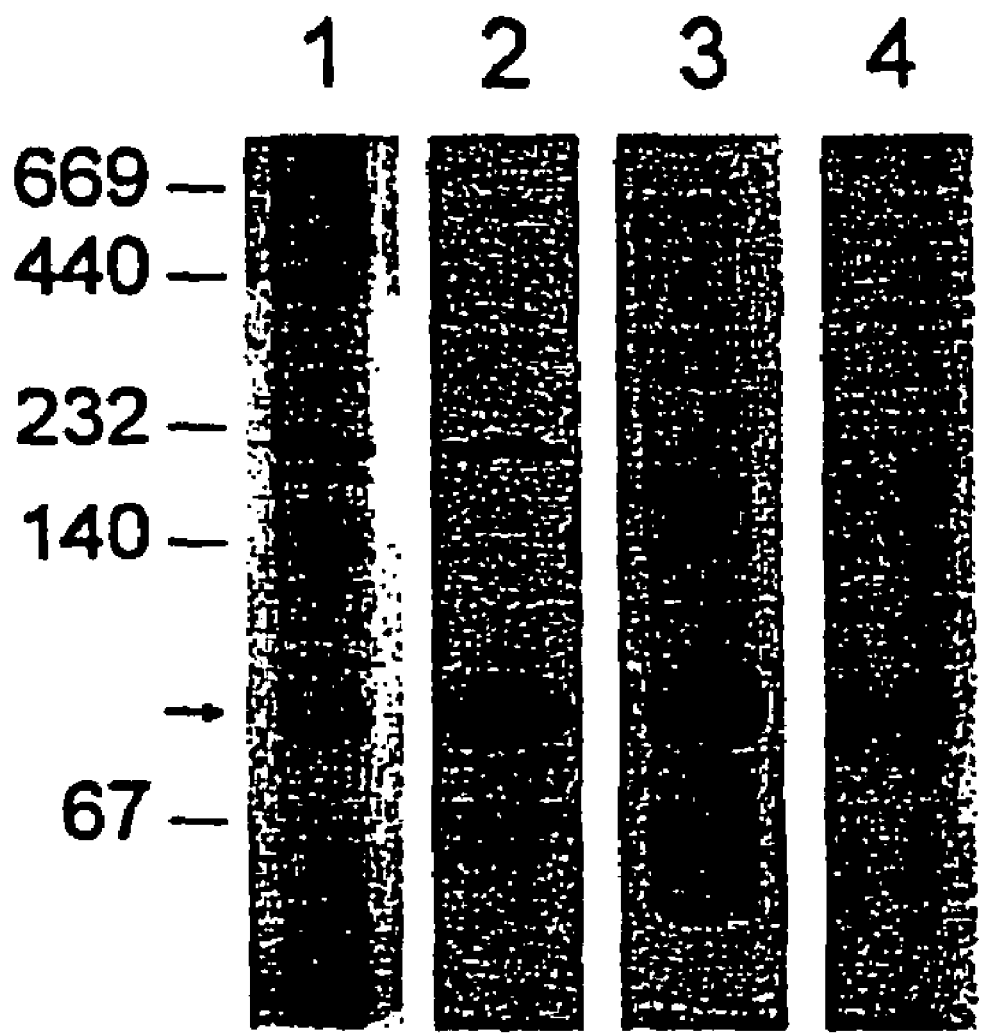
Figure 3:
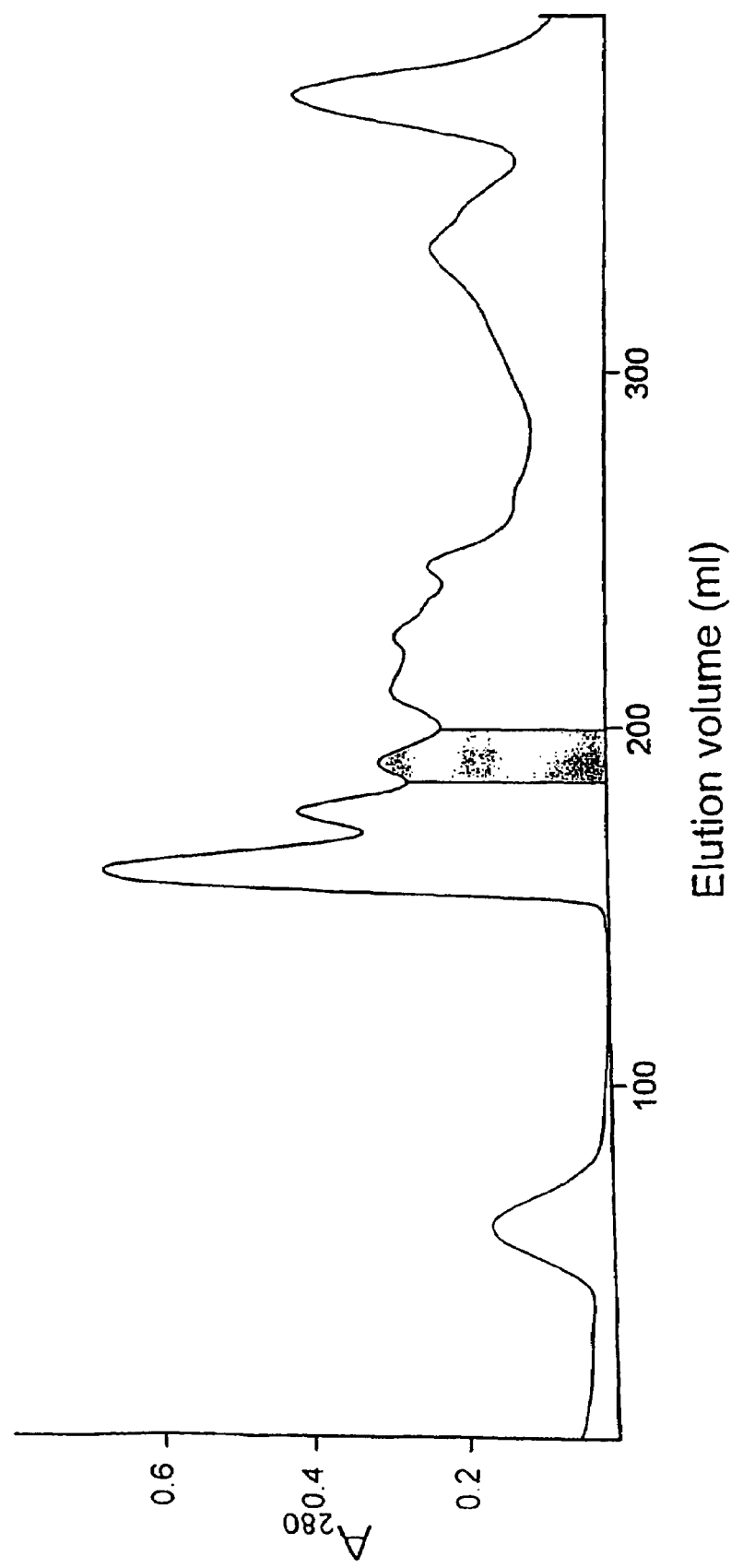
Figure 4:
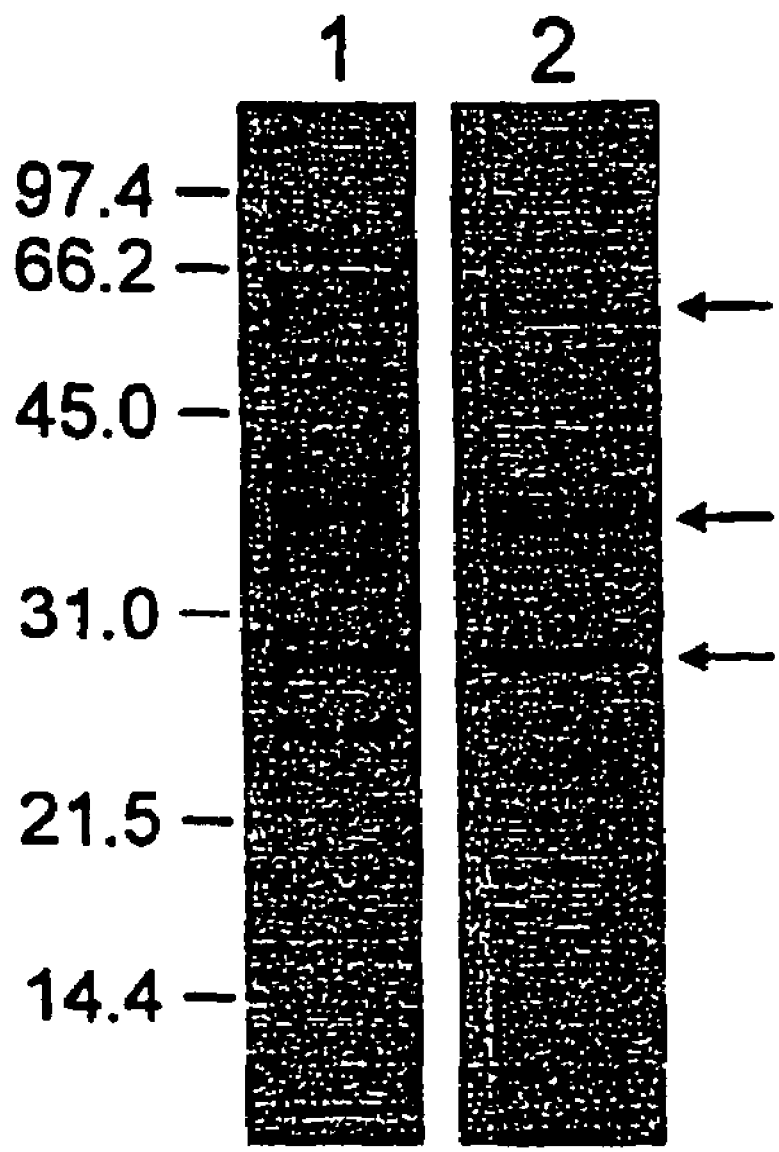
Figure 5:
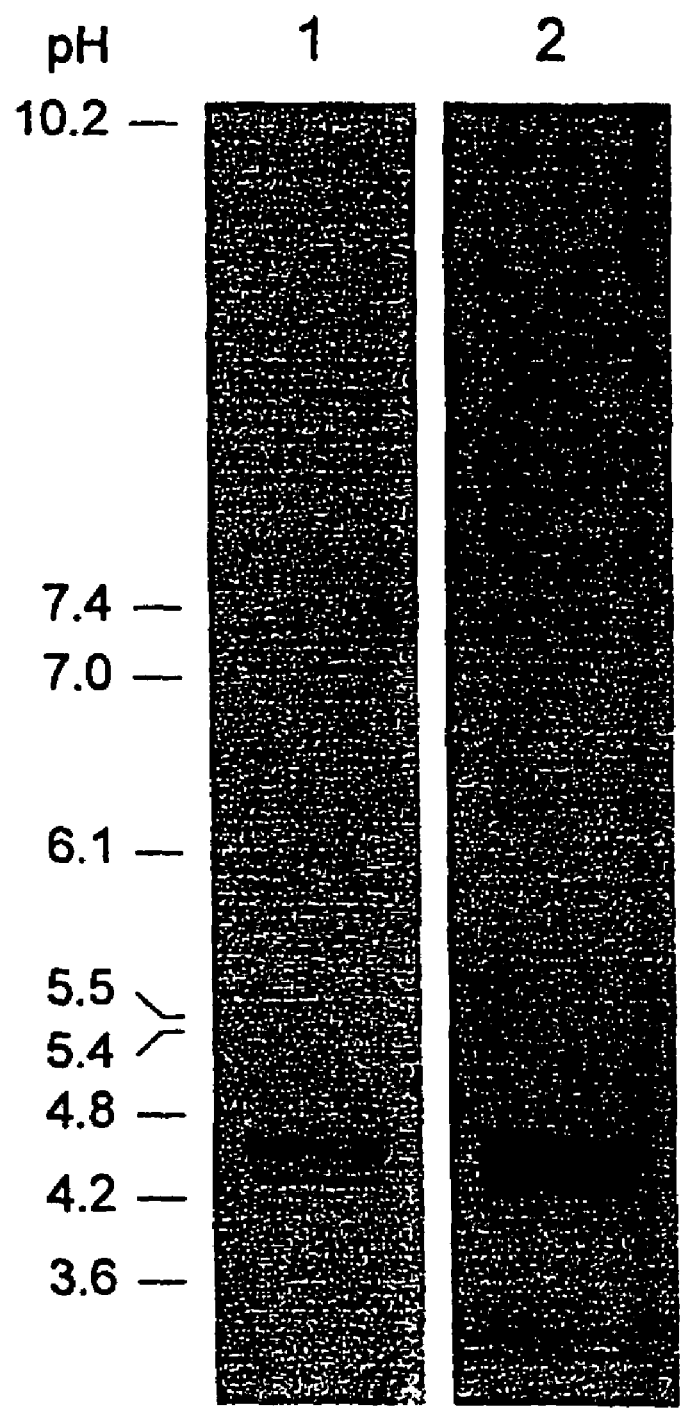
Figure 6:
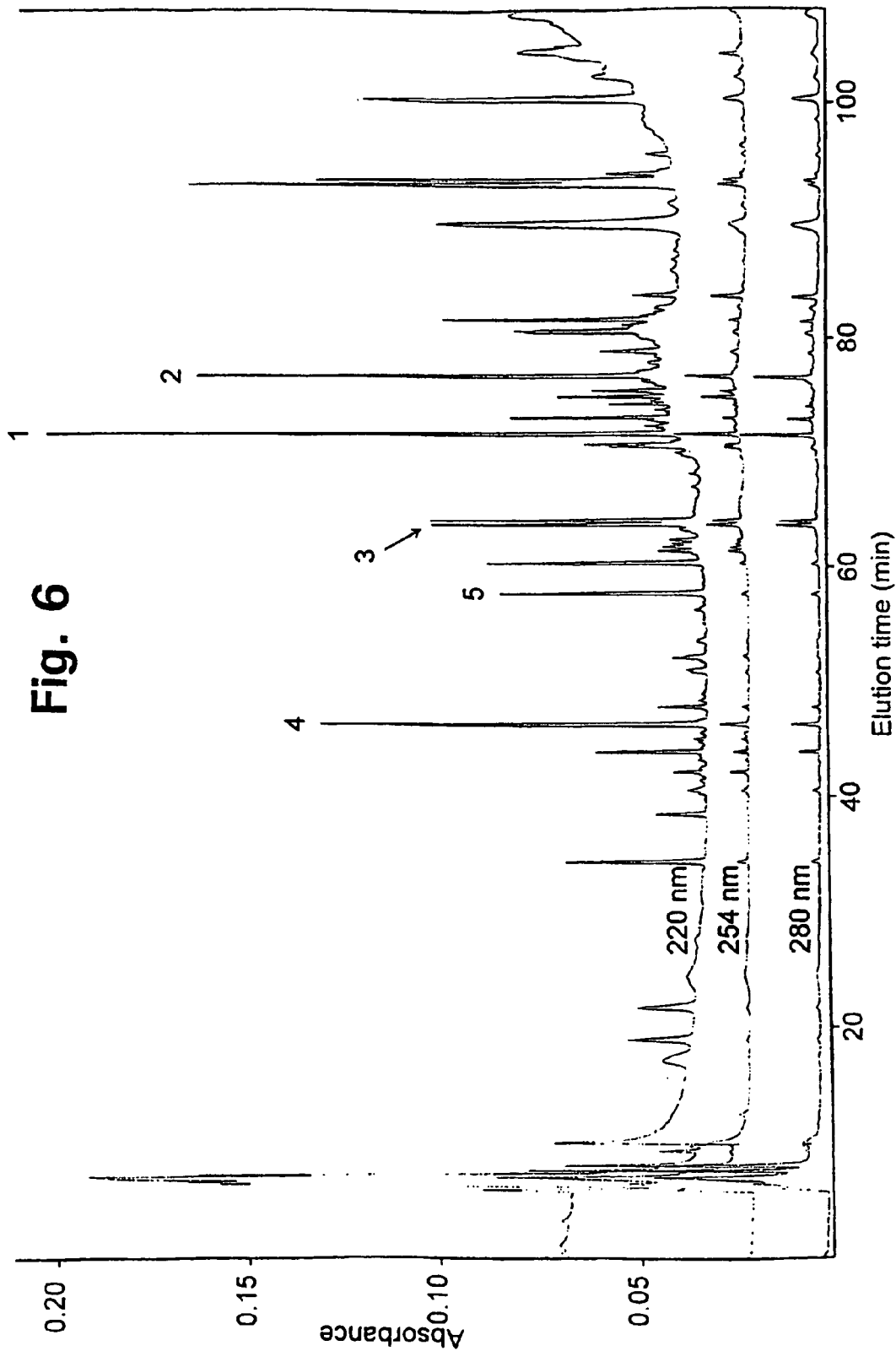
Figure 7:
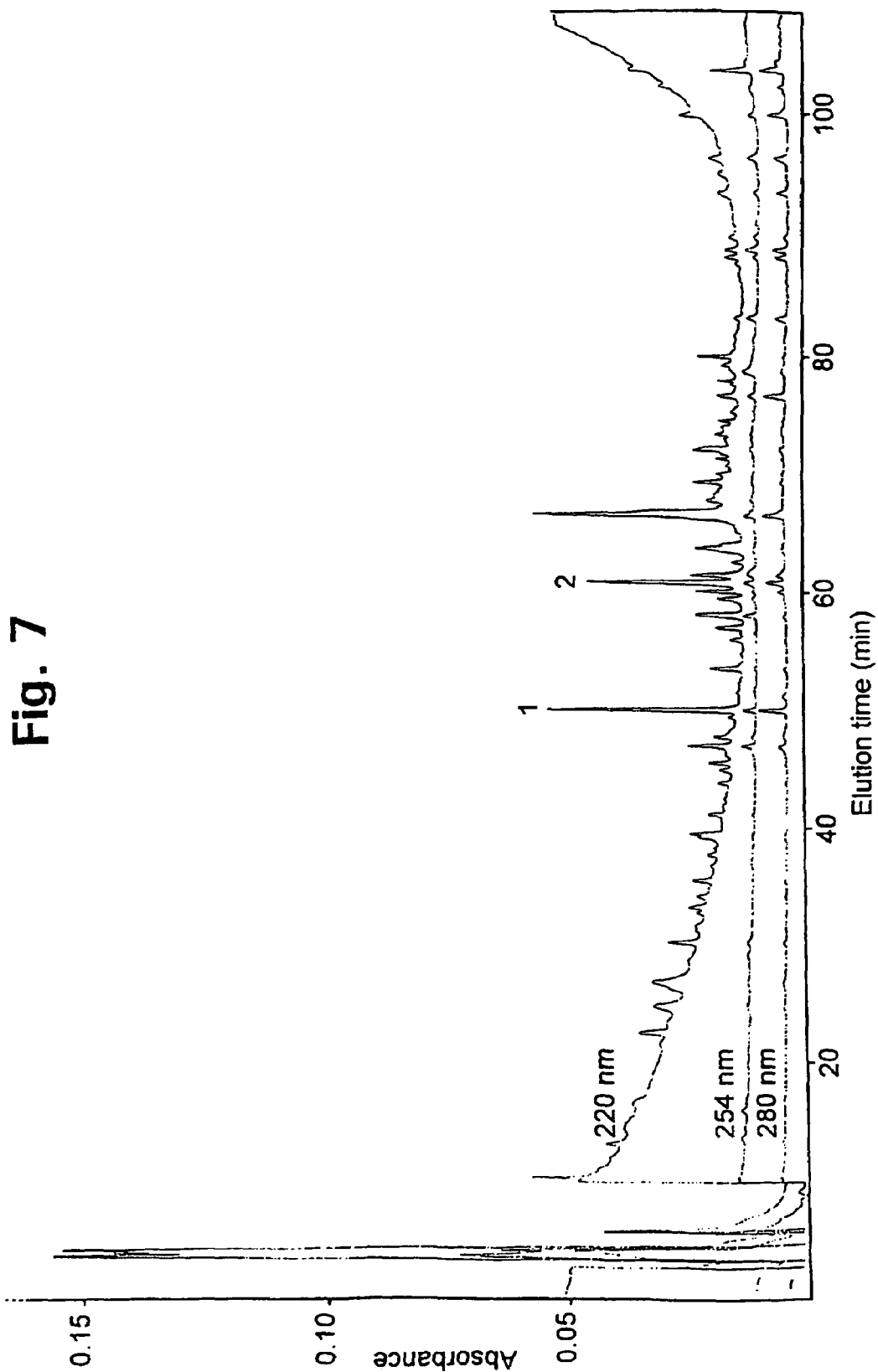
Figure 8:
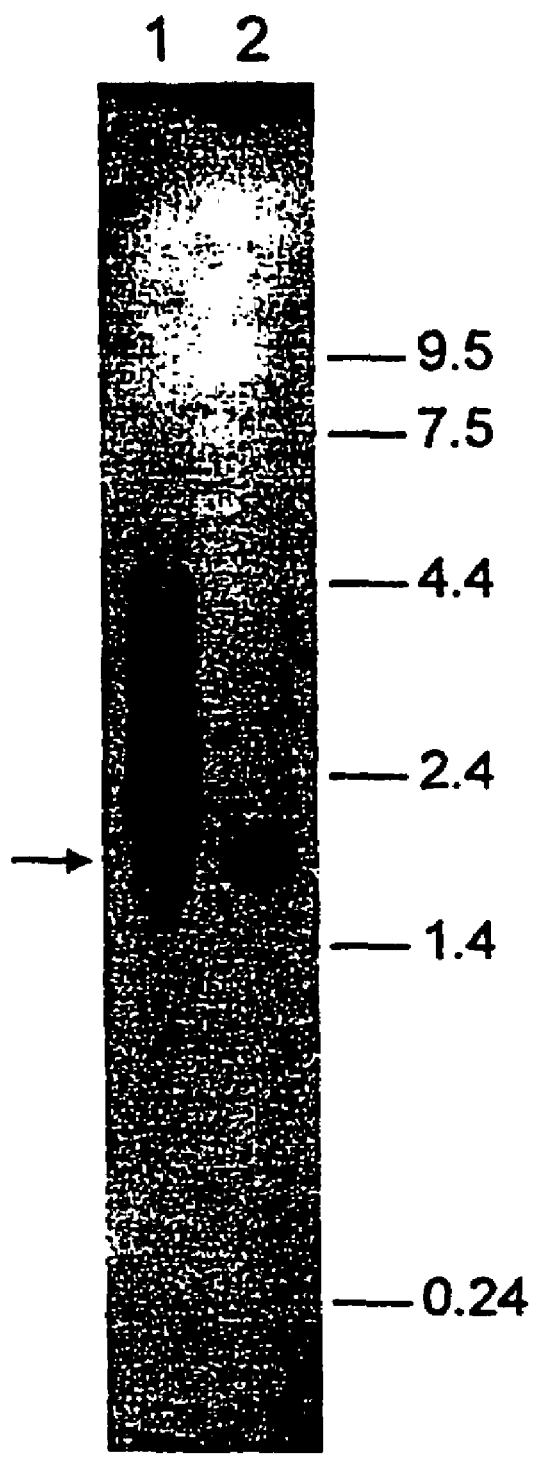
Figure 9:
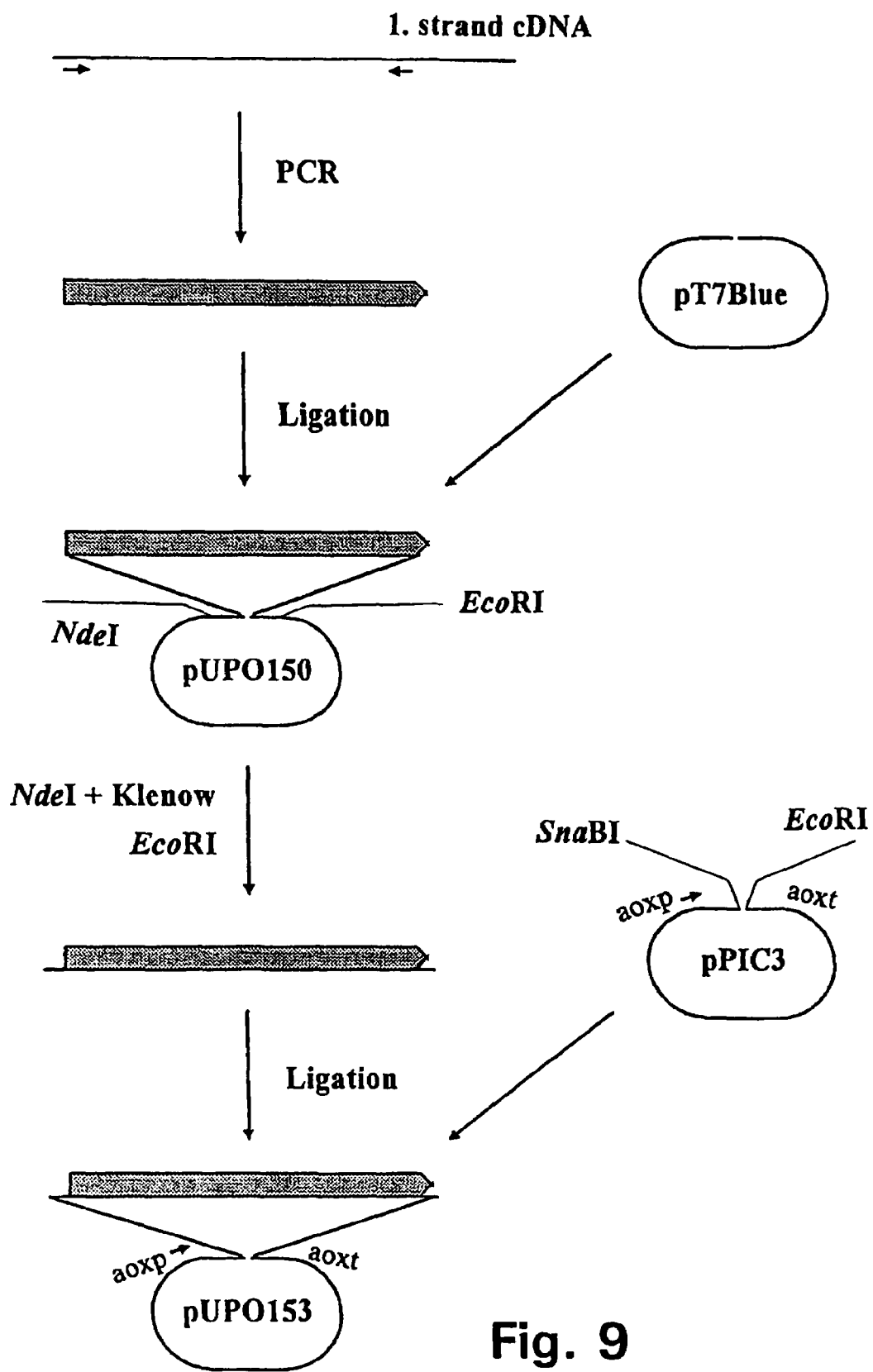
Figure 10:
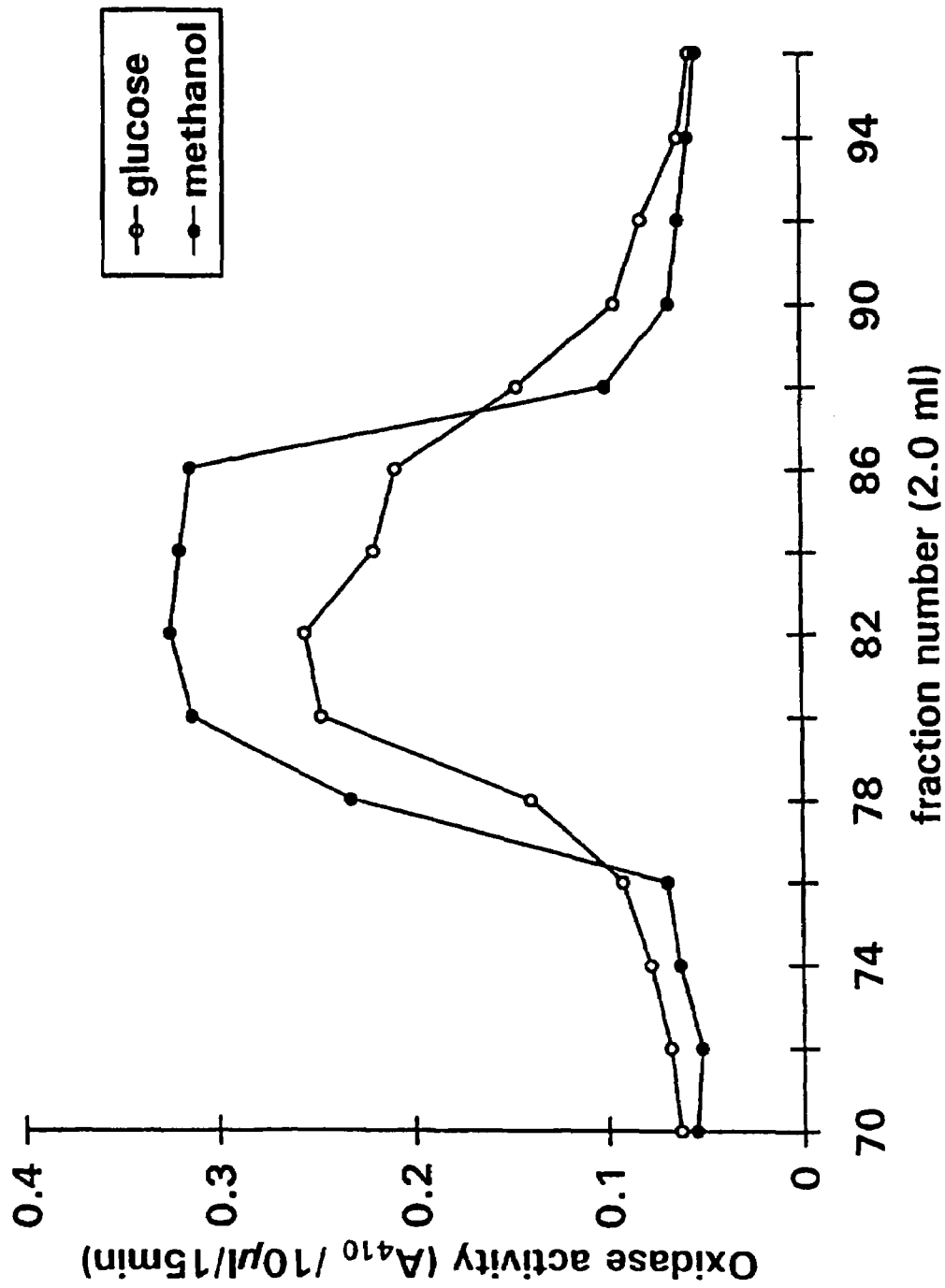
Figure 11:
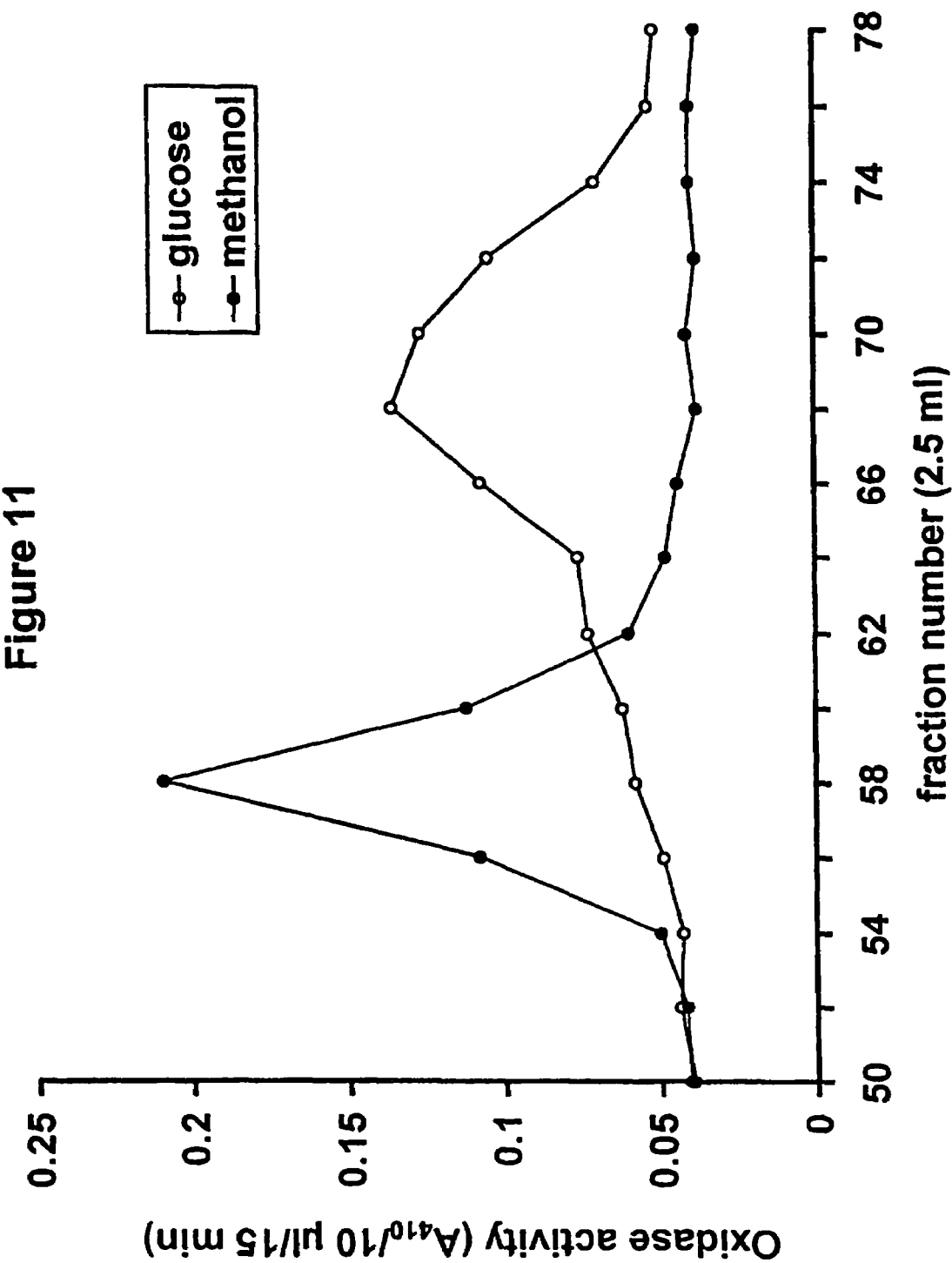
Figure 12:
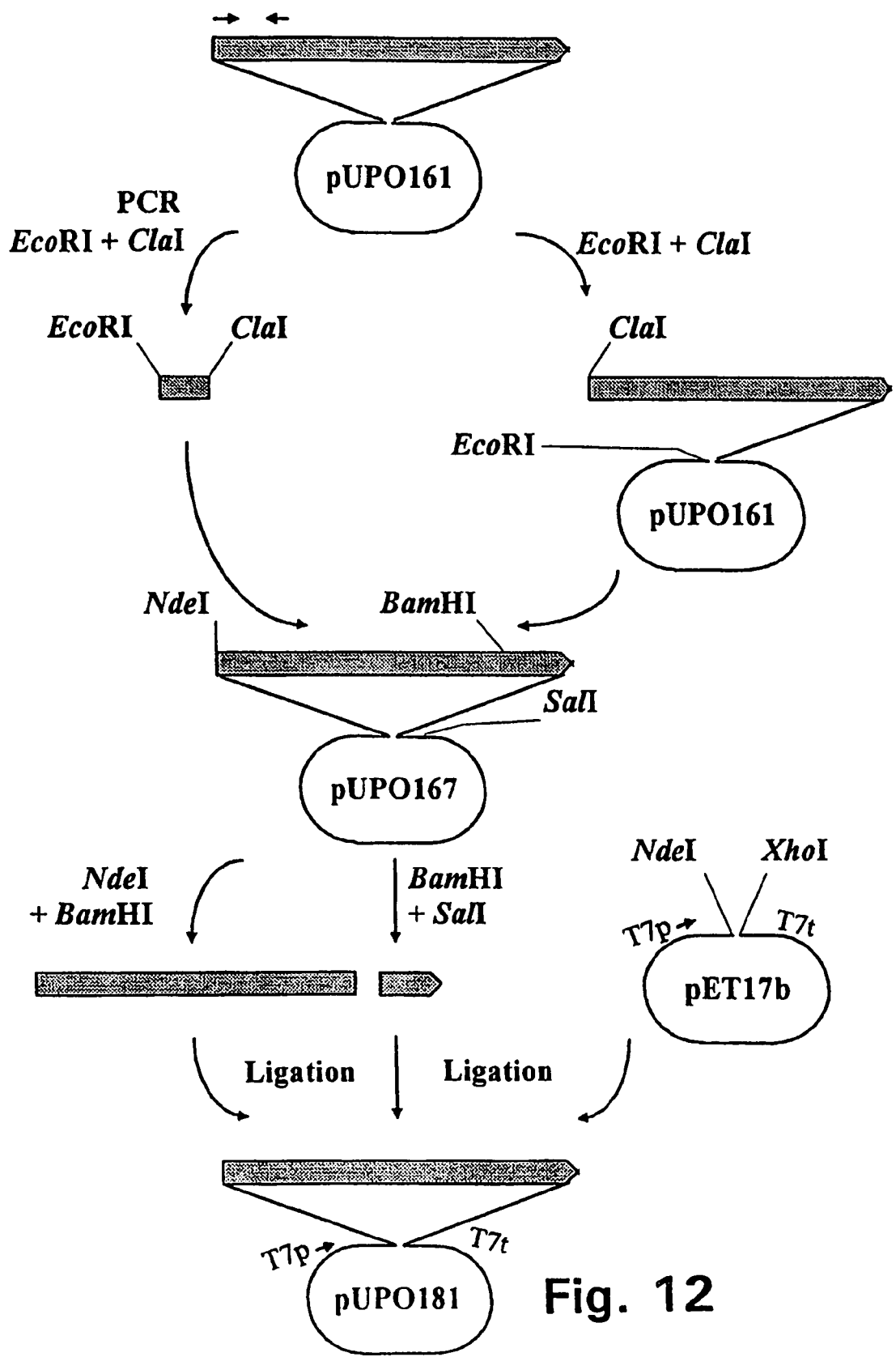
Figure 13:
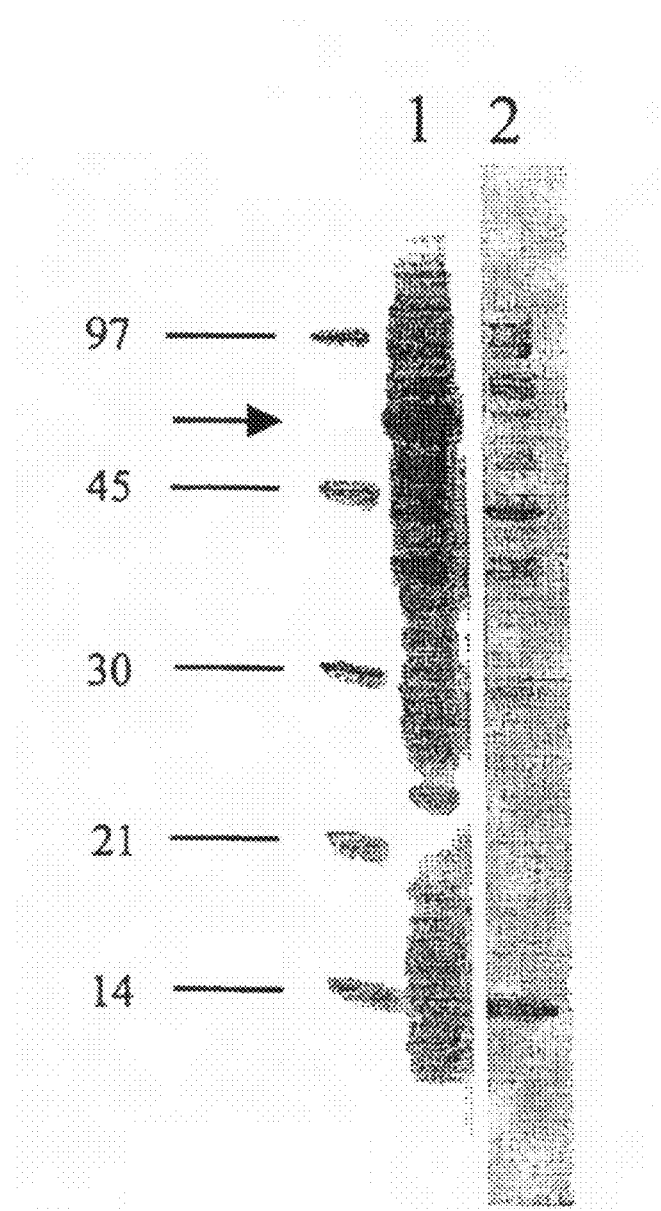
Figure 14:
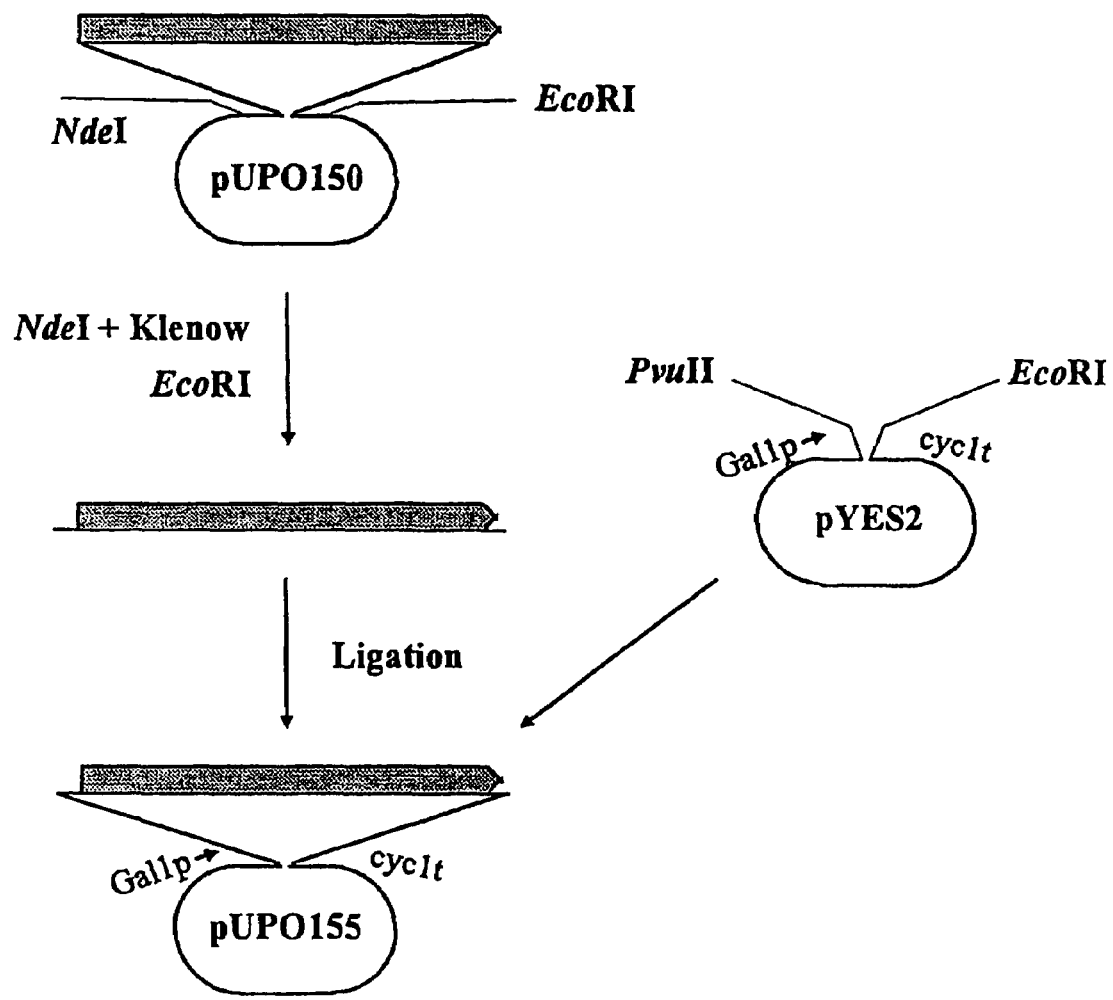

The invention will now be described by way of illustration in the following examples and the annexed drawings of which:

FIG. 1 represents a schematic overview of the purification of hexose oxidase (HOX) and the two strategies adopted for obtaining amino acid sequence information, FIG. 2 shows native, non-dissociating polyacrylamide gel electrophoresis (native PAGE) of preparations of hexose oxidase at different steps of the purification. The samples represent the enzyme preparation obtained after anion exchange chromatography and concentration (lane 1), after gel filtration (lane 2), and after either cation exchange chromatography (lane 3) or chromatofocusing (lane 4). The Phast gel (Pharmacia, B-25% gradient gel) was silver stained. Molecular weights of standard proteins ($\times 10^{-3}$) are indicated at the left. The band corresponding to hexose oxidase, which is indicated by an arrow, was identified by enzyme staining of another gel in parallel (not shown). The four lanes were run on separate gels, FIG. 3 shows the UV-profile obtained during purification of hexose oxidase by gel filtration on Sephacryl S-200 HR as described in the text. Fractions containing hexose oxidase (HOX) activity are indicated by the filled area, FIG. 4 shows SDS-PAGE of hexose oxidase purified from *Chondrus crispus* by anion exchange chromatography on DRAE-Sepharose Fast Flow, gel filtration on Sephacryl S-200, followed by either cation exchange chromatography on S-Sepharose Fast Flow (lane 1) or chromatofocusing on a Mono P column (lane 2). Molecular weights of standard proteins ($\times 10^{-3}$) are indicated at the left. The polypeptides at 60 kD, 40 kD and 29 kD are marked by arrows. Reduced samples were run on a 12% polyacrylamide gel which was stained with Coomassie Brilliant Blue R-250. The two lanes were run on separate gels, FIG. 5 shows isoelectric focusing (IEF) of hexose oxidase. The gel was either stained with Coomassie Brilliant Blue R-250 (lane 1) or stained for enzyme activity as described in the text (lane 2). The positions of isoelectric point markers run in parallel are shown at the left. The two lanes were run on separate gels, FIG. 6 shows reversed phase HPLC separation of peptides generated by digestion of the 40 kD HOX-polypeptide with endoproteinase Lys-C. The peaks labelled 1, 2, 3, 4 and 5 were subjected to amino acid sequencing, FIG. 7 shows reversed phase HPLC separation of peptides generated by digestion of the 29 kD HOX-polypeptide with endoproteinase Lys-C. The peaks labelled 1 and 2 were subjected to amino acid sequencing, FIG. 8 shows a Northern blot analysis of RNA extracted from *Chondrus crispus*. The denaturing agarose gel was loaded with 30 μg (lane 1) and 3 μg (lane 2), respectively of total RNA. Left arrow indicates hexose oxidase specific transcript. The positions of molecular weight markers in kb are shown to the right, FIG. 9 shows the construction of plasmid pUPO153 which mediates the expression of recombinant hexose oxidase in *Pichia pastoria*. Small arrows indicate PCR primers. The grey box indicates the hexose oxidase gene, FIG. 10 shows purification of recombinant hexose oxidase from *Pichia pastoris* by anion exchange chromatography on HiTrap-Q column (step one). Alcohol oxidase (AOX) activity (●) and hexose oxidase (HOX) activity (○) in the collected fractions were assayed as described in the text, FIG. 11 shows purification of recombinant hexose oxidase from *Pichia pastoris* by gel filtration on Sephacryl S-200 HR (step two). Alcohol oxidase (AOX) activity (●) and hexose oxidase (HOX) activity (○) in the collected fractions were assayed as described in the text, FIG. 12 shows the construction of plasmid pUPO181 which mediates the expression of recombinant hexose oxidase in *E. coli*. Small arrows indicate PCR primers (grey box indicates the hexose oxidase gene), FIG. 13 shows SDS-PAGE of recombinant hexose oxidase produced in *E. coli*. Crude extracts from lysed cells were analyzed in a 14% denaturing gel. Molecular weights of standard proteins ($\times 10^{-3}$) are indicated to the left. The gel was stained with Coomassie Brilliant Blue R-250. Lane 1 shows extract from *E. coli* cells with pUPO181, lane 2 shows plasmid-less control. Arrow shows hexose oxidase band and FIG. 14 shows the construction of plasmid pUPO155 which mediates the expression of recombinant hexose oxidase in *Saccharomyces cerevisiae*. Small arrows indicate PCR primers. The grey box indicates the hexose oxidase gene.

EXAMPLE 1

Purification of Hexose Oxidase from *Chondrus crispus*

A schematic overview of the purification and two strategies adopted for obtaining amino acid sequence information for the enzyme is shown in FIG. 1.

1.1. Collection, Drying and Grinding of *Chondrus crispus*

The red sea-weed *Chondrus crispus* was collected during April to September at the shore near Grenå, Jutland, Denmark at a depth of 2-5 meters. Freshly collected algal fronds were rinsed with cold water and stored on ice during transport to the laboratory (<24 hours). The sea-weed was then either dried immediately or stored in frozen state until further processing. For enzyme purification the material was stored at −18° C., whereas the material intended for isolation of mRNA was stored in liquid nitrogen.

Fronds of *Chondrus crispus* were thawed at 4° C. and air-dried at room temperature (20-25° C.) for 2-3 days. The dried material was ground to fine powder in a Waring Commercial Blendor (model 34BL97, Waring, New Hartford, Conn., USA).

1.2. Extraction of Enzyme

About 500 g of *Chondrus crispus* powder was mixed with 2.5 l of 20 mM Tris-Cl, pH 7.0. The water used throughout all extraction and purification procedures was obtained from a Milli-Q UF Plus Laboratory Water Purification System (Millipore). The buffer was pre-cooled to 4° C. The mixture was kept at 4° C. for 6-8 days. The extract was collected by filtration through several layers of gauze.

The sea-weed material was subjected to repeated extractions which were carried out as the first one described above. The material was usually discarded after 5-8 extractions when residual activity had declined to an almost negligible level.

The filtrate was clarified by centrifugation at 10,000×g in a Sorvall GSA rotor (Sorvall Instruments). The supernatant was filtered through Whatman chromatography paper (chr 1) and diluted with water to a conductivity of 7-8 mS/cm. pH was adjusted to 7.5. The extract was then ready for anion exchange chromatography as described below.

1.3. Assay of Hexose Oxidase

The procedure used was essentially as described by Sullivan and Ikawa, 1973. This assay is based on the principle that the hydrogen peroxide formed in the oxidation of the sugar in the presence of peroxidase reacts with the chromogenic substance, o-dianisidine to form a dye with absorbance at 402 nm.

The assay mixture consisted of 1-40 µl of enzyme sample and 850 µl of an assay solution containing 370 µl of 0.1 M sodium phosphate buffer, pH 7.0; 462 µl of 0.1 M D-glucose in 0.1 M sodium phosphate buffer, pH 7.0; 9 µl of horse radish peroxidase, 0.1 mg/ml in water (Sigma Chemicals, cat. no. P 6782 or Boehringer Mannheim, cat. no. 814 393); and 9 µl of o-dianisidine.2HCl, 3.0 mg/ml in water (3,3'-dimethoxybenzidine, Sigma Chemicals). After incubation at room temperature for 15 or 30 minutes the assay was stopped by addition of one drop of 37% HCl (Merck, p.a.). Samples of 100 µl were transferred from the assay tubes to the wells of a microtiter plate (NUNC, Denmark) and the absorbance at 410 nm was read on a Titertek Multiskan II PLUS plate reader (Labsystems/Flow Laboratories, Finland). To ensure that the observed activity was due to hexose oxidase—and not glucose oxidase—the assay was occasionally performed with D-galactose as the substrate instead of D-glucose.

1.4. Anion Exchange Chromatography

This step was carried out on a BioPilot chromatography system (Pharmacia Biotech, Sweden) connected to a Super-Rac fraction collector (LKB-Produkter AB, Sweden).

This and the following steps in the purification were carried out at room temperature (20-25° C.), but the fraction collector was placed in a refrigerator so that collected fractions were stored at 4° C. until enzyme assay. Absorbance at 280 nm and conductivity were recorded. The extract was applied onto a XK50/30 column (Pharmacia, 5.0×25 cm) with a bed volume of 500 ml which had been packed with DRAB-Sepharose Fast Flow (Pharmacia) and equilibrated with buffer A: 20 mM Tris-Cl, pH 7.5. The flow rate was 5 ml/min during sample application and 10 ml/min during the subsequent steps of the chromatography. After sample application, the column was washed with 1200 ml of buffer A. Adsorbed proteins were eluted with 2800 ml of a gradient from 0% to 100% buffer B: 20 mM Tris-Cl, 500 mM NaCl, pH 7.5. Fractions of 15 ml were collected during the gradient elution.

After each chromatographic run the column was regenerated with 500 ml of 0.5 M NaOH, neutralised with 500 ml of 1.0 M Tris-Cl pH 7.5 and finally equilibrated with 1200 ml of buffer A. The collected fractions were assayed for hexose oxidase activity as described above (40 µl of sample, 30 min of incubation time). Fractions of hexose oxidase activity were pooled and stored at 4° C.

1.5. Concentration of Hexose Oxidase Activity-Containing Fractions

Several pools of fractions from DBAE-Sepharose chromatography were pooled and concentrated by ultrafiltration in a Millipore Lab Ultrafiltration Cassette System (cat. no. XX420LCSO). The system was equipped with a 30,000 nominal molecular weight limit (NMWL) membrane cell (cat. no. PTTKOLCP2) and was driven by a peristaltic pump. After concentration at room temperature to about 50 ml, the enzyme preparation was further concentrated to 10-20 ml by centrifugal ultrafiltration at 4° C. in Centriprep concentrators (Amicon, USA, nominal molecular weight cut-off 30,000) according to the instructions of the manufacturer. The concentrated enzyme solution was stored at 4° C.

1.6. Native Polyacrylamide Gel Electrophoresis (PAGE)

The composition of the preparation of hexose oxidase obtained by ion exchange chromatography and ultrafiltration was analyzed by native PAGE on a Pharmacia Phast System, see FIG. 2. The 8-25% gradient gels were run and silver stained for protein according to the instructions of the manufacturer. A kit containing the following molecular weight markers was also obtained from Pharmacia: Thyreglobulin (669,000); ferritin (440,000); catalase (232,000); lactate dehydrogenase (140,000) and albumin (67,000).

Staining for hexose oxidase activity was carried out as described for glucose oxidase by Sock & Rohringer (1988). In principle, the redox reaction catalyzed by glucose oxidase or hexose oxidase is coupled with reduction of tetrazolium salt to coloured, insoluble formazan.

Immediately after electrophoresis the Phast gel was submerged in 10 ml of freshly prepared staining solution containing: 0.1 M D-glucose (or D-galactose); 85 mM citric acid/sodium phosphate pH 6.5; 0.2 mg/ml of 3-(4,5-dimethylthiazol-2-yl)-2,5-diphenyl-tetrazolium bromide ("thiazolyl blue", MTT, Sigma Chemicals, cat. no. M 2128); and 0.1 mg/ml of N-methyl-dibenzopyrazine methyl sulfate salt ("phenazin methosulfate", PMS, Sigma Chemicals cat. no. P 9625). The gel was incubated at room temperature in the dark until the coloured, blue-violet band was clearly visible (usually 5-90 minutes) and was then rinsed in 10% acetic acid, 5% glycerol and air-dried.

The silver stained gel is shown in FIG. 2, lane 1. As it appears from the figure, numerous proteins were present at this step of the purification. By enzyme staining, however, only the band marked with an arrow in FIG. 2 was stained. (results not shown).

1.7. Gel Filtration

This step in the purification was carried out on an FPLC system (Pharmacia) equipped with a XK26/70 column (2.6× 66 cm, Pharmacia) with a bed volume of 350 ml. The column was packed with Sephacryl S-200 HR (Pharmacia) according to the instructions of the manufacturer. The buffer was 20 mM Tris-Cl, 500 mM NaCl, pH 7.5 and the flow rate was 0.5 ml/min. The UV-absorbance at 280 nm was recorded. Fractions of 2.5 ml were collected with a FRAC-100 fraction collector (Pharmacia) which was placed in a refrigerator (4° C.) next to the FPLC. The concentrated preparation of hexose oxidase was clarified by centrifugation at 30,000 rpm in a SW60 swinging bucket rotor (Beckman) in an L7 ultracentrifuge (Beckman) for 60 min at 4° C. An aliquot of 3.0-4.0 ml of the supernatant was mixed with 5% glycerol (Sigma Chemicals, cat. no. G 7757), filtered through a disposable filter unit with 0.22 µm pore size (Millipore, cat. no. SLGV 025 BS) and applied onto the column using an SA-5 sample applicator (Pharmacia) connected to the inlet of the column. Fractions showing hexose oxidase activity were identified using the assay method described above (10 µl of sample, 15 min of incubation time) and stored separately at −18° C. until further processing.

The UV-profile and the elution position of hexose oxidase is shown in FIG. 3. As it appears from this figure, a substantial amount of UV-absorbing material was eliminated in this step.

Blectrophoretic analysis by native PAGE and silver staining (FIG. 2, lane 2) showed that only a few contaminating components remained after this step.

1.8. Determination of Molecular Weight of Native Hexose Oxidase by Analytical Gel Filtration The molecular weight of native hexose oxidase was determined by gel filtration on Sephacryl S-200 Superfine (Pharmacia). Column dimensions, buffer, flow rate and fraction collection were as described above. Blue dextran for determination of the void volume ($v_o$) of the column and the following standard proteins for calibration of the column were obtained from Pharmacia: Ovalbumin (43,000), albumin (67,000), catalase (158,000) and aldolase (252,000). A sample containing hexose oxidase was obtained by DEAE-Sepharose chromatography as described above. Based on determination of the elution volumes ($v_e$) of the standard proteins and of hexose oxidase, the corresponding $K_{av}$ values ($v_e-v_o/v_t-v_o$) were calculated. Finally, the $K_{av}$ values of the standard proteins were plotted against the corresponding log (molecular weight) values. The $K_{av}$ of hexose oxidase corresponded to a native molecular weight of approximately 110,000. This is in good agreement with Sullivan & Ikawa (1973), who found a molecular weight of about 130,000. Kerschensteiner & Klippenstein (1978) reported a molecular weight of 140,000, also as determined by gel filtration.

1.9. Cation Exchange Chromatography

This step was carried out on a SMART Micropurification Chromatography System (Pharmacia) equipped with a HR5/5 column (Pharmacia, 0.5×5 cm, bed volume 1.0 ml) packed with S-Sepharose Fast Flow (Pharmacia). The column was equilibrated in A-buffer: 50 mM sodium acetate, pH 4.5 (prepared by adjusting 50 mM acetic acid to pH 4.5 with NaOH). The buffer B used for gradient elution contained 50 mM sodium acetate, 500 mM NaCl, pH 4.5. Fractions from gel filtration were desalted on pre-packed, disposable Sephadex G-25 columns (PD-10, Pharmacia) which were equilibrated and eluted with 25 mM sodium acetate, pH 4.5. Twenty ml of desalted sample derived from 6 gel filtration fractions with high hexose oxidase activity were applied onto the column from a 50 ml Superloop (Pharmacia) at a flow rate of 250 µl/min. The column was then washed with 4 bed volumes of buffer A at the same flow rate. Bound proteins were eluted with a gradient from buffer A to buffer B over 5 ml. Fractions of 250 µl were collected during gradient elution and assayed for hexose oxidase activity as described above (1 µl of sample, 15 min of incubation time) and stored at −18° C. until further use.

The resultant preparation of hexose oxidase was analyzed by native PAGE and silver staining (FIG. 2, lane 3). The hexose oxidase band was now the only significant band, although small amounts of contaminating proteins were also observed.

1.10. Analytical Sodium Dodecyl Sulphate PAGE (SDS-PAGE)

Fractions from S-Sepharose chromatography that showed hexose oxidase activity were also analyzed by SDS-PAGH according to Laemmli (1970). Minigels of 12.5% acrylamide/bisacrylamide (37.5:1 mixture) with a thickness of 0.75 mm were run in a Mini-Protean II apparatus (Bio-Rad). The gels were stained with 0.1% Coomassie Brilliant Blue R-250, 10% acetic acid, 40% ethanol and destained in 10% acetic acid, 30% ethanol.

The result of the electrophoresis is shown in FIG. 4, lane 1. The purified preparation of hexose oxidase showed strong bands at relative molecular weights of 40 kD and 29 kD, respectively and faint bands at 60 kD and 25 kD, respectively. Furthermore, two sharp doublet bands at 55 kD and 57 kD were observed.

1.11. SDS-PAGE Followed by Blotting and Staining for Carbohydrate

The presence of carbohydrate in the isolated hexose oxidase was examined with the DIG Glycan Detection Kit (Boehringer Mannheim), which is designed for detection of microgram amounts of sugars in glycoconjugates on blots. In principle, adjacent hydroxyl groups in carbohydrates are oxidized to aldehydes. Digoxigenin is then covalently bound to the aldehyde groups and subsequently detected with an anti-digoxigenin-alkaline phosphatase antibody conjugate.

Purified hexose oxidase from cation exchange chromatography was run on a 12% SDS-PAGE gel as described above, blotted to nitrocellulose according to standard procedures and stained for carbohydrate with the Glycan Detection Kit according to the instructions of the manufacturer. None of the hexose oxidase bands at 60 kD, 40 kD, 29 kD and 25 kD were stained. Only the sharp doublet band at 57 kD-55 kD was intensely stained (results not shown). The 57 kD-55 kD doublet band was later identified as a residual contaminant as described below.

Thus, it could be concluded that none of the hexose oxidase components seen in SDS-PAGB were glycosylated.

1.12. Isoelectric Focusing

Hexose oxidase fractions from S-Sepharose chromatography were pooled and concentrated by centrifugal ultrafiltration in Centricon concentrators (Amicon) and analyzed by isoelectric focusing (IEF) on Isogel agarose plates, pH 3-10, according to the instructions of the manufacturer (FMC Bioproducts, Rockland, Me., USA). A mixture of pI markers (FMC Bioproducts) were run in parallel with the hexose oxidase samples. The mixture consisted of cytochrome C (pI=10.2), myoglobin major/minor band (7.4/7.0), carbonic anhydrase (6.1), β-lactoglobulin A/B (5.4/5.5), ovalbumin (4.8), glucose oxidase (4.2) and amyloglucosidase (3.6). The gels were stained with Coomassie Brilliant Blue R-250. As shown in FIG. 5, lane 1, the purified preparation of hexose oxidase was composed of two variants with pI's of 4.3 and 4.5, respectively. Purified hexose oxidase was also analyzed by isoelectric focusing on pre-cast polyacrylamide gels, pH 3.5-9.5 (Pharmacia, Ampholine PAGplates) according to the instructions of the manufacturer. These gels were stained for enzyme activity by incubation in a staining mixture as described above for native polyacrylamide gels. As shown in FIG. 5, lane 2, both pI variants were enzymatically active.

1.13. Chromatofocusing

The observation of several bands in SDS-PAGE of hexose oxidase purified on S-Sepharose as the final step aroused the suspicion that one or more of the bands might represent residual contaminants. Furthermore, the S-Sepharose chromatography consistently gave low recoveries. Therefore, chromatofocusing was introduced as a last purification step instead of cation exchange chromatography on S-Sepharose.

Chromatofocusing was carried out on the SMART chromatography system equipped with a Mono P HR 5/5 column (0.5×5 cm, Pharmacia) with a bed volume of 1 ml and a 50 ml Superloop for sample application. The start buffer for separation in the interval between pH 5.0 and 3.5 was 25 mM piperazine adjusted to pH 5.5 with HCl. The eluent was Polybuffer 74 (Pharmacia) 10-fold diluted with water and adjusted to pH 3.5 with HCl. The column was pre-treated and equilibrated with start buffer as recommended by the manufacturer.

Sample preparation was carried out in the following manner: In a typical experiment the best fractions from two gel filtration runs (2×4 fractions, 20 ml) were pooled and passed through a column of 1 ml of Phenyl Sepharose 6 Fast Flow (high sub, Pharmacia) which had been packed in a disposable Poly-prep column (Bio-Rad) and equilibrated in the buffer used for gel filtration (20 mM Tris-Cl, 500 mM NaCl, pH 7.5). This treatment almost completely removed remaining amounts of the red protein phycoerythrin and other coloured substances which were adsorbed to the gel matrix at this ionic strength, and thereby eliminated contaminants that were only partially removed during the other steps of the purification process. The Phenyl Sepharose column was discarded after use. Hexose oxidase activity was quantitatively recovered in the effluent which was then desalted on pre-packed disposable Sephadex G-25 columns (PD-10, Pharmacia) equilibrated and eluted with start buffer.

Before sample application 1 ml of eluent was pumped onto the column. The flow rate was 0.5 ml/min. After sample application the pH gradient was formed by pumping 11 ml of eluent through the column. During the pH gradient elution 44 fractions of 250 µl were collected. Fractions containing hexose oxidase were identified by the assay method described above (1 µl of sample, 15 min of incubation time) and stored at −18° C. until further use.

Hexose oxidase purified by chromatofocusing was analyzed by native PAGE and silver staining (FIG. 2, lane 4) and by SDS-PAGE and staining with Coomassie Brilliant Blue (FIG. 4, lane 2). In native PAGE the hexose oxidase band was the only significant band, and only very low amounts of contaminants were observed. By SDS-PAGE it was clearly demonstrated that this purification method was able to remove the sharp doublet band at 57 kD and 55 kD. The band at 25 kD observed after S-Sepharose chromatography was very faint after chromatofocusing.

In conclusion, hexose oxidase obtained by DEAB chromatography, gel filtration and chromatofocusing showed one band in native PAGE. In SDS-PAGE strong bands at 40 kD and 29 kD and a weak band at 60 kD were observed.

Since the intensity of the 60 kD component, relative to the 40 kD and 29 kD components, varied between different preparations of the enzyme, it was hypothesized that the 29 kD and 40 kD polypeptides might originate from proteolytic processing of an about 60 kD precursor. This would fit with the idea of a homo-dimeric structure of the enzyme with a native molecular weight of 110,000-120,000 as it was actually found by gel filtration, as described above. Furthermore, this hypothesis would be consistent with the results obtained by Kerschensteiner and Klippenstein who found a native molecular weight of 140,000 in gel filtration and a subunit molecular weight of 70,800 in SDS-PAGE (Kerschensteiner and Klippenstein, 1978).

EXAMPLE 2

Generation and Amino Acid Sequence Analysis of Peptide Fragments of Hexose Oxidase 2.1. Digestion of Purified Hexose Oxidase with Cyanogen Bromide This procedure was carried out while cation exchange chromatography on S-Sepharose was still used as the last purification step.

Hexose oxidase obtained by purification on DEAR Sepharose, Sephacryl S-200, and S-Sepharose was transferred to a volatile buffer by buffer-exchange on a pre-packed PC3.2/10 Fast Desalting Column containing Sephadex G-25 Superfine (Pharmacia, 0.32×10 cm, bed volume 0.8 ml) which was mounted in the above SMART system. The column was equilibrated and eluted with 200 mM ammonium bicarbonate (BDH, AnalaR). To obtain a satisfactory recovery it was necessary to add 500 mM sodium chloride to the hexose oxidase sample before injection.

Eluted, buffer-exchanged hexose oxidase was distributed into 1.5 ml microcentrifuge tubes and lyophilized in a Speedvac concentrator (Savant Instruments). Cyanogen bromide (CNBr, Pierce), 200 µl of a 10 mg/ml solution in 70% v/v formic acid (Promega), was added. (Reagents from Promega were components of a "Probe Design Peptide Separation System" cat. no. V6030). The tubes were incubated overnight in the dark at room temperature. The solutions were then dried in the speedvac concentrator, resuspended in 50 µl of water and re-dried.

2.2. Separation of Cyanogen Bromide Fragments by High Resolution SDS-PAGE and Electroblotting to Difluoride (PVDF) Membrane The peptides generated by cyanogen bromide digestion were separated by high resolution SDS-PAGE according to Schägger & von Jagow (1987). This system provides excellent separation of low molecular weight peptides (20-250 amino acid residues). The gel system consisted of a 16.5% separation gel, a 10% spacer gel and a 4% stacking gel, all made using a 29:1 acrylamide/bisacrylamide mixture from Promega.

Minigels with a thickness of 0.75 mm were run in a Mini-Protean II apparatus (Bio-Rad). Ammonium persulfate and N,N,N',N'-tetramethyl-ethylenediamine (TEMED) were from Bio-Rad. SDS was from United States Biochemical (ultrapure). Tris was from Fluka (cat. no. 93350). Tricin and sodium thioglycate were from Promega. Glycin (p.a.), 2-mercaptoethanol (p.a.) and bromophenol blue was from Merck and glycerol from GIBCO BRL (ultrapure). Sodium thioglycolate, 0.1 mM, was added to the cathode buffer just before use to prevent chemical blockage of the amino-termini of the peptides during the separation. The gel was pre-run for 60 min at 30 V to allow the thioglycolate to scavenge any amino-reactive substances.

Sample preparation: The dried cyanogen bromide peptide fragments were resuspended in 30 µl of gel loading buffer containing 63 mM Tris-Cl, pH 6.8, 1% SDS, 2.5% 2-mercaptoethanol, 10% glycerol and 0.0012% bromophenol blue. Samples that turned yellow upon mixing, due to the content of residual formic acid were neutralized by addition of 1-3 µl of 1.0 M Tris base until the blue colour was restored. The samples were denatured by heating at 95° C. for 5 min before application on the gel. A mixture of Low-Range Protein molecular weight standards (Promega) with molecular weights between 31,000 and 2,500 were run in parallel with the hexose oxidase peptide samples. The electrophoresis was run at 150V constant voltage.

Electrophoretic transfer to PVDF membrane was carried out in a Mini Trans-Blot Electrophoretic Transfer Cell (Bio-Rad) according to the instructions of the manufacturer. Three sheets of Problott membrane (Applied Biosystems) cut to the size of the gel were wetted briefly in methanol (Merck, p.a) and then soaked in transfer buffer (25 mM Tris, 192 mM glycine, pH 8.5, pre-cooled to 4° C.) until assembly of the blotting sandwich. After electrophoresis the gel was incubated in transfer buffer for 5 min at 4° C. and then assembled into a transfer sandwich having the following layers: A sheet of Whatman paper (3 MM chr), two sheets of Problott membrane, the SDS-PAGE peptide separation gel, the third sheet of Problott, and a final sheet of Whatman paper. The sandwich was oriented with the two sheets of Problott membrane toward the positive electrode in the electrode assembly. The cooling unit was mounted in the buffer chamber before it was filled with pre-cooled transfer buffer, and the transfer was then performed at room temperature for 60 min at 100 V constant voltage. During transfer the current increased from about 270 mA to about 400 mA.

After transfer the membrane was washed in water for 1 min and then stained for 30-45 sec in 100 ml of freshly prepared staining solution containing 0.1 Coomassie Brilliant Blue R-250 (Bio-Rad), 5% acetic acid (Merck, p.a) and 45% methanol (Merck, p.a). The membrane was then destained with 3 changes of about 80 ml of freshly prepared 5% acetic acid, 45% methanol for 30-60 sec each. The membrane was finally washed in 3 changes of water to remove residual glycine and then air-dried. Well-resolved and relatively abundant bands of molecular weights of about 2.5 kD, 9 kD and 16 kD, respectively were excised and submitted to amino acid analysis and sequence analysis.

2.3. Amino Acid Analysis and Sequencing of a 9 kD Cyanogen Bromide Fragment of Hexose Oxidase Amino acid analysis was carried out by ion exchange chromatography and post-column derivatization with o-phtaldialdehyde. Samples were hydrolyzed at 110° C. for 20 h in 6 M HCl, 0.05% phenol and 0.05% dithiodipropionic acid (Barkholt and Jensen, 1989). Peptides were sequenced on an automated protein/peptide sequencer from Applied Biosystems, model 477A, equipped with on-line PTH analyzer, model 120A and data analysis system. Protein sequencing reagents were obtained from Applied Biosystems. Amino acid analysis and peptide sequence analysis was kindly performed by Arne L. Jensen, Department of Protein Chemistry, University of Copenhagen, Denmark.

The peptide sequence identified by analysis of the 9 kD fragment is shown in Table 2.1.

The initial yield of phenylthiohydantoin-tyrosine (PTH-Tyr) at step one was 22 pmol. The amino acid composition of the 9K fragment is shown in Table 2.2.

TABLE 2.1

Peptide sequence obtained by sequence analysis of a 9 kD cyanogen bromide fragment of hexose oxidase

| Origin of sequenced peptide | Sequence identification | Amino acid sequence |
|---|---|---|
| HOX, 9K CNBr fragment | HOX-1 peptide | Y-E-P-Y-G-G-V-P- (SEQ ID NO: 1) |

Abbreviations: Y=Tyr; E=Glu; P=Pro; G=Gly; V=Val

TABLE 2.2

Amino acid composition of a 9 kD cyanogen bromide fragment of hexose oxidase

| Amino Acid | mol % | N |
|---|---|---|
| Asx | 16.4 | 14 |
| Thr | 4.8 | 4 |
| Ser | 4.6 | 4 |
| Glx | 9.9 | 8 |
| Pro | 8.1 | 7 |
| Gly | 11.2 | 9 |
| Ala | 4.3 | 4 |
| Cys | 0 | 0 |
| Val | 5.2 | 5 |
| Met | 0.2 | 0 |
| Ile | 3.6 | 3 |
| Leu | 9.3 | 8 |
| Tyr | 6.1 | 5 |
| Phe | 4.6 | 4 |

TABLE 2.2-continued

Amino acid composition of a 9 kD cyanogen bromide fragment of hexose oxidase

| Amino Acid | mol % | N |
|---|---|---|
| His | 1.0 | 1 |
| Lys | 8.1 | 7 |
| Arg | 2.7 | 2 |
| Trp | ND[1)] | — |
| total | 100.0 | 85 |

[1)]Not determined 2.4. Preparative SDS-PAGE and Electroblotting to PVDF Membrane The following procedure was carried out in order to obtain amino acid sequences which were specifically known to stem from either the 40 kD or the 29 kD polypeptide of the hexose oxidase preparation.

Preparative SDS-PAGE gels were run according to Laemmli (Laemmli, U. K., 1970). Minigels containing 12.5% acrylamide/bisacrylamide (37.5:1 mixture) with a thickness of 0.75 mm were run in a Mini-Protean II apparatus (Bio-Rad). The solution of acrylamide (BDH, cat. no. 44313) and N,N'-methylene-bis-acrylamide (BDH, cat. no. 44300) was stored over mixed bed ion exchange resin (Bio-Rad, cat. no. 142-6425). The sources of all other reagents were as described above.

Sample preparation: Fractions from chromatofocusing were concentrated by centrifugal ultrafiltration at 4° C. in Ultra-free-MC filter units with NMWL 10,000 and a sample capacity of 400 μl (Millipore, cat. no. UFC3 LGC25). The retentate was mixed with one volume of gel loading 2× buffer containing 125 mM Tris-Cl, pH 6.8, 2% SDS, 5% 2-mercaptoethanol, 20% glycerol and 0.0025% bromophenol blue. Samples that turned yellow upon mixing, due to the content of acidic Polybuffer components, were neutralized by addition of 1-3 μl of 1.0 M Tris base until the blue colour was restored. The samples were denatured by heating at 95° C. for 5 min and applied on the gel in aliquots of about 30 μl per lane.

A mixture of molecular weight marker proteins (Bio-Rad) with molecular weights ranging from 97,400 to 14,400 was run in parallel with the hexose oxidase samples. The electrophoresis was run at low current, 10 mA per gel, in order to minimize the risk of thermally induced, chemical modification of the sample proteins.

Electrophoretic transfer to PVDF membrane was carried out as described above, except that one sheet of Immobilon P Membrane (Millipore, cat. no. IPVH 15150) was used instead of three sheets of Problott. The sandwich was oriented with the blotting membrane toward the positive electrode in the electrode assembly.

After transfer the Immobilon P membrane was rinsed in water for 10 sec and then stained for 45-60 sec in 100 ml of freshly prepared staining solution containing 0.025% Coomassie Brilliant Blue R-250, 5% acetic acid and 40% methanol. The membrane was then destained for 2-3 min in 250 ml of freshly prepared 5% acetic acid, 30% ethanol (96% v/v, Danisco, Denmark). The membrane was finally air-dried and stored at 4° C.

The band pattern on the blot was identical to the pattern seen in analytical SDS-PAGE after final purification by chromatofocusing. It showed strong bands at 40 kD and 29 kD, in addition to a faint band at 60 kD.

Bands at 40 kD and 29 kD were excised from the blot and used for amino acid analysis and for enzymatic digestion of polypeptides bound to the membrane, as described below. The amount of 60K material was too low to permit any further analysis of this polypeptide.

2.5 Amino Acid Analysis of 40 kD and 29 kD Polypeptides of Hexose Oxidase

The amino acid compositions of the 40 kD and 29 kD components of hexose oxidase are shown in Table 2.3.

TABLE 2.3

Amino acid composition of 40 kD and 29 kD polypeptides of hexose oxidase

| Amino acid | mol % | |
|---|---|---|
| | 40K | 29K |
| Asx | 11.5 | 12.5 |
| Thr | 5.9 | 5.2 |
| Ser | 6.1 | 4.7 |
| Glu | 9.7 | 15.1 |
| Pro | 5.2 | 5.4 |
| Gly | 13.6 | 9.7 |
| Ala | 6.6 | 6.4 |
| Cys | 1.1 | 0.9 |
| Val | 7.3 | 5.5 |
| Met | 1.5 | 2.3 |
| Ile | 3.7 | 4.4 |
| Leu | 8.5 | 8.6 |
| Tyr | 4.2 | 5.3 |
| Phe | 5.5 | 4.1 |
| His | 2.2 | 1.4 |
| Lys | 3.9 | 6.1 |
| Arg | 3.5 | 2.4 |
| Trp | ND[1] | ND[1] |
| Total | 100.0 | 100.0 |

[1] Not determined 2.6. Enzymatic Digestion of PVDF-Bound Hexose Oxidase Polypeptides Digestion of hexose oxidase polypeptides bound to PVDF and extraction of the resultant proteolytic peptides was performed as described by Fernandez et al. (1992) and Fernandez et al. (1994).

Digestion of the 40 kD polypeptide of hexose oxidase: Eleven 40K bands with an estimated total protein content of about 5 µg (corresponding to about 125 pmol) were excised from the Coomassie blue-stained PVDF membrane, destained in methanol for 1-2 min and rinsed in water for 2-3 min. The membrane bands were then diced into 1×1 mm pieces and transferred to microcentrifuge tubes. A blank region of PVDF membrane served as a background control. The diced membrane pieces were soaked in 50 µl of digestion buffer containing 1% (v/v) hydrogenated Triton X-100 (RTX-100, Sigma Chemicals, cat. no. X-100R-PC, or Calbiochem, protein grade, cat. no. 648464), 10% acetonitrile (Merck, Gradient Grade Lichrosolv) and 100 mM Tris-Cl, pH 8.0. The proteolytic enzyme selected for the digestion was endoproteinase Lys-C (endoLys-C) which cleaves peptide chains at the C-terminal side of lysine residues. An aliquot of 5 µg of endoLys-C (Boehringer Mannheim, sequencing grade, cat. no. 1047 825) was reconstituted by addition of 20 µl of water. Two µl of enzyme solution, corresponding to 0.5 µg was added (enzyme:substrate ratio 1:10). Digestion was carried out at 37° C. for 22-24 h.

After digestion the samples were sonicated in an ultrasonic tank (Elma transonic) for 5 min and centrifuged at 1700 rpm in a microcentrifuge for 5 min, and the supernatant was then transferred to a new tube. Consecutive washes with 50 µl of digestion buffer and 100 µl of 0.1% trifluoroacetic acid (TFA, Pierce, cat. no. 28902) were performed with sonication and centrifugation as described above. All supernatants were pooled, resulting in an extract volume of 200 µl. The extracts were kept at −18° C. until peptide purification. Digestion of the 29 kD polypeptide of hexose oxidase was performed as described for the 40 kD component, except that four bands with a total protein content of 2.4 µg (about 80 pmol), according to amino acid analysis, were used.

2.7. Purification of endoLys-C Generated Peptides

The peptide fragments obtained by digestion of 40 kD and 29 kD polypeptides of hexose oxidase were separated on the SMART chromatography system. The system was equipped with a variable-wavelength µPeak monitor and a fraction collector bowl for 60 vials. The reversed phase column used for the separation was a silica-based µRPC C2/C18 SC2.1/10 narrow-bore column (Pharmacia, column dimensions 2.1× 100 mm, particle size 3 µm, average pore size 125 Å). The buffers were A: 0.1% TFA (Pierce) in Milli-Q water and B: 0.1% TFA in acetonitrile (Merck, gradient grade Lichrosolv). The buffers were filtered and degassed by vacuum filtration on a 0.5 µm fluoropore filter (Millipore, cat. no. FHLP04700). The flow rate was 100 µl/min. UV-absorbance in the effluent was monitored at 220 nm, 254 nm and 280 nm. The gradient was 0-30% B (0-65 min), 30-60% B (65-95 min) and 60-80% B (95-105 min). The column was then washed at 80% B for 10 min at 100 µl/min and re-equilibrated in A-buffer for 45 min at 200 µl/min. Fractions of 50 µl were collected between t=15 min and t=105 min (3×60 fractions) and stored at −18° C. until amino acid sequence analysis.

The peptide map obtained after endoLys-C digestion of the 40 kD polypeptide is shown in FIG. 6. As seen in this figure, the digestion and HPLC separation resulted in several well-resolved peaks with a high signal-to-noise ratio. A corresponding chromatogram of a blank digestion mixture (not shown) indicated that the peaks eluting later than t=83 min were non-peptide, reagent-derived peaks, possibly UV-absorbing contaminants of the hydrogenated Triton X-100 or residual traces of Coomassie dye. The peaks labelled 1-5 in FIG. 6 were selected for amino acid sequencing by the following criteria: 1) Peak height. 2) Apparent purity. 3) High $A_{280}$:$A_{220}$ and/or high $A_{254}$:$A_{220}$ ratio indicating the presence of aromatic amino acid residues, which are most useful for selection of PCR primer sequences due to their low genetic code degeneracy. 4) Late elution time, which may indicate a relatively long peptide.

The chromatogram of the 29 kD endoLys-C peptides is shown in FIG. 7. Obviously, this hexose oxidase component gave rise to only a few significant peptide fragments compared to the 40 kD component in FIG. 6. When comparing the chromatograms, there was no indication of any peptide fragment being present in both digests. This finding suggests that the 40K and 29K hexose oxidase components do not have amino acid sequences in common, which would have been the case if the 29 kD chain was generated by proteolytic conversion of the 40 kD polypeptide. (Compared to the 40 kD digest, the 29 kD digest contained only small amounts of the contaminating substances eluting later than t=83 min. The reason for this might be that hydrogenated Triton X-100 from Calbiochem was used for the 29 kD digestion, whereas the 40 kD digestion was carried out with Triton X-100 from Sigma Chemicals).

Fractions corresponding to the peaks labelled 1 and 2 in the 29 kD peptide map (FIG. 7) were subjected to amino acid sequencing.

2.8 Amino Acid Sequence Analysis of Proteolytically Generated Peptides of Hexose Oxidase The peptide sequences identified by analysis of fractions corresponding to peaks 1-5 in FIG. 6 (HOX-2, HOX-3, HOX- 4, HOX-5 and HOX-6 peptides) and peaks 1-2 in FIG. 7 (HOX-7 and HOX-8 peptides) are shown in the below Table 2.4. The initial yields of PTH amino acids ranged from 46 pmol of PTH-Tyr at step one in the HOX-5 peptide to 6 pmol of PTH-Ile at step two in the HOX-8 peptide. As expected from the absorbances at 254 nm and 280 nm, respectively of the selected peaks all the sequenced peptides contained at least one aromatic amino acid residue.

TABLE 2.4

Peptide sequences obtained by sequence analysis of endoproteinase Lys-C peptides derived from 40 kD and 29 kD polypeptides of hexose oxidase

| Origin of sequenced peptide | Sequence identification | Amino acid sequence |
|---|---|---|
| 40K, peak 1 | HOX-2 peptide | A-I-I-N-V-T-G-L-V-E-S-G-Y-D-$X^{1)}$-$X^{2)}$-$X^{3)}$-G-Y-X-V-S-S- |
| 40K, peak 2 | HOX-3 peptide | D-L-P-M-S-P-R-G-V-I-A-S-N-L-W-F- |
| 40K, peak 3 | HOX-4 peptide | D-S-E-G-N-D-G-E-L-F-X-A-(H)-T- |
| 40K, peak 4 | HOX-5 peptide | Y-Y-F-K |
| 40K, peak 5 | HOX-6 peptide | D-P-G-Y-I-V-I-D-V-N-A-G-T-P-D- |
| 29K, peak 7 | HOX-7 peptide | L-Q-Y-Q-T-Y-W-Q-(E)-(E)-(D)- |
| 29K, peak 2 | HOX-8 peptide | X-I-(R)-D-F-Y-E-E-M- |

Tentatively identified residues are shown in parentheses.
1) Residue no. 15 was identified as either Asp or Asn.
2) residue no. 16 was identified as either Asp or Ala.
3) Residue no. 17 was identified as either Arg or Trp.

HOX-2 peptide=SEQ ID NO:9

HOX-3 peptide=SEQ ID NO:10

HOX-4 peptide=SEQ ID NO:11

HOX-5 peptide=SEQ ID NO:12

HOX-6 peptide=SEQ ID NO:13

HOX-7 peptide SEQ ID NO:14

HOX-8 peptide=SEQ ID NO:15

EXAMPLE 3

Isolation of Hexose Oxidase Gene from *Chondrus crispus*

3.1. Purification of RNA from *Chondrus Crispus*

Freshly collected fronds of *Chondrus crispus* were rinsed with cold water and immediately stored in liquid nitrogen until further use. About 15 grams of *Chondrus crispus* thallus frozen in liquid nitrogen was homogenized to a fine powder in a mortar. The frozen, homogenized material was transferred to a 50 ml tube (Nunc, cat. no. 339497) containing 15 ml extraction buffer (8M guanidinium hydrochloride; 20 mM 2-(N-morpholino)ethanesulfonic acid (MES), pH 7.0; 20 mM ethylenediaminetetraacetic acid (EDTA); 50 mM β-mercaptoethanol).

The tube was vortexed and kept cold (0° C.) during the following steps unless other temperatures are indicated. Then the tube was centrifuged for 20 minutes at 6,000×g in a Heraeus Omnifuge 2.0RS and the RNA-containing supernatant (about 15 ml) was carefully collected and transferred to a pre-chilled 50 ml tube. 1.5 ml 2 M sodium acetate, pH 4.25, 15 ml water saturated phenol and 3 ml chloroform:isoamyl alcohol (49:1) was added to the tube containing the RNA extract.

The tube was subsequently vortexed vigorously for ½ minute and the phases were separated by centrifuging the tube for 20 minutes in an Omnifuge at 6,000×g. The aqueous phase (about 17 ml) was transferred to a 30 ml Corex tube (Sorvall, cat. no. 00156) and an equal volume (i.e. about 17 ml) of cold isopropanol was added. The tube was vortexed again and incubated for at least 1 hour at −20° C. The precipitated RNA was pelleted by centrifugation for 20 minutes at 10,000 rpm using a Sorvall RC-5B centrifuge provided with a pre-chilled SSC rotor. The supernatant was discarded and the pelleted RNA was resuspended in 4 ml 0.3 M sodium acetate, pH 5.5 and 12 ml 96% ethanol was added.

The Corex tube was then vortexed and incubated again for at least 1 hour at −20° C. followed by a second pelleting of RNA by centrifugation for 20 minutes as described above. The supernatant was carefully discarded and the RNA pellet resuspended in 2 ml 0.15 M sodium acetate, pH 5.5. Then 8 ml 4 M sodium acetate, pH 5.5. was added and the RNA was precipitated on ice for 30 minutes and pelleted again as described above. The RNA pellet was washed in 70% ethanol and resuspended in 500 µl water. The resuspended RNA was transferred to a microcentrifuge tube and stored at −20° C. until further use.

The purity and concentration of the RNA was analyzed by agarose gel electrophoresis and by absorption measurements at 260 nm and 280 nm as described in Sambrook et al. (1989).

3.2. Isolation of Poly-Adenylated RNA from *Chondrus crispus*

Poly-adenylated RNA was isolated from total RNA using magnetic beads containing oligo dT (Dynabeads® Oligo $(dT)_{25}$, in mRNA Purification Kit™, Dynal). Approximately 100 µg total RNA was mixed with 1 mg Dynabeads® Oligo $(dT)_{25}$ and poly-adenylated RNA was isolated as described in the protocol for the mRNA Purification Kit™. The yield of poly-adenylated RNA isolated with Dynabeads® was between 1 and 3%.

Other methods were used in the isolation of poly-adenylated RNA from *Chondrus crispus* including using columns packed with oligo-(dT)-cellulose (Clontech, cat. no. 8832-2) or pre-packed columns (mRNA Separator Kit™, Clontech, cat. no. K1040-1) as described in the protocol for the mRNA Separator Kit™. The yield of poly-adenylated RNA isolated on oligo-(dT) columns was between 0.1 and 1% of the initial total RNA. Poly-adenylated RNA isolated on oligo-(dT) columns was used in cDNA synthesis reactions as described below (3.4), but the yield of first strand cDNA was very low (less than 1%).

The reason for the lower yield and the poorer performance of RNA isolated on oligo-(dT) columns compared to Dynabeads® purified RNA could be the presence of carbohydrates or proteoglycans in the extract of total RNA. Carbohydrates contaminating the total RNA preparations have been shown to impede the purification of poly-adenylated RNA and to inhibit cDNA synthesis and therefore, methods for the purification of RNA free of carbohydrates have been developed (Groppe et al., 1993; Yeh et al.) However, poly-adenylated RNA purified with these methods was not as effective in cDNA synthesis reactions as RNA isolated with Dynabeads®. Accordingly, poly-adenylated RNA purified using Dynabeads® was used as template in first strand cDNA synthesis reactions (cf. 3.4 below).

3.3. Hexose Oxidase Specific Oligonucleotides

Synthetic oligonucleotides were synthesized (DNA technology, ApS, Forskerparken, DK-8000 Aarhus C, Denmark) based on the amino acid sequences derived from hexose oxidase peptides HOX-2, HOX-3 and HOX-4 (Table 2.4). Table 3.1 shows the oligonucleotides and their corresponding amino acid sequences. Also shown in Table 3.1 is the DNA sequence of the primers used in DNA sequencing or in PCR.

When Y is C or T, R is A or G; when W is A or T, S is C or G; when D is A, G or T, N is A, C, G or T, and I=deoxy Inosine.

Hox-2=SEQ ID NO:9
Hox2-3+=SEQ ID NO:16
Hox-3=SEQ ID NO:10
Hox3-2-=SEQ ID NO:17
Hox-4=SEQ ID NO:11
Hox4-1+=SEQ ID NO:18
Hox4-2-=SEQ ID NO:19
Hox5+=SEQ ID NO:20
Hox5-=SEQ ID NO:21
Hox6+=SEQ ID NO:22
Hox7-=SEQ ID NO:23
Hox8-=SEQ ID NO:24
Hox10-=SEQ ID NO:25
Hox11+=SEQ ID NO:26
Hox12-=SEQ ID NO:27
Hox13-=SEQ ID NO:28
Hox5'-1=SEQ ID NO:29

TABLE 3.1

Nucleotide sequences of synthetic oligonucleotides specific for hexose oxidase

| Hox-peptide | Hox-primer | | | | | | | | | | | | | | |
|---|---|---|---|---|---|---|---|---|---|---|---|---|---|---|---|
| Hox-2 | | A | I | I | N | V | T | G | | | | | | | |
| | | L | V | E | S | G | Y | D | X | X | X | G | Y | X | V | S | S |
| | Hox2-3+ | ⁵'YTI GTI GAR WSI GGN TAY GA³' | | | | | | | | | | | | | |
| Hox-3 | | D | L | P | M | S | P | R | G | - | | | | | |
| | | | V | I | A | S | N | L | W | F | | | | | |
| | Hox3-2- | ⁵'CAN TAD CGN AGI TTR RAI ACC AA³' | | | | | | | | | | | | | |
| Hox-4 | | D | S | E | G | N | D | G | E | L | F | X | A | H | T |
| | Hox4-1+ | ⁵'GAR GGI AAY GAY GGI GAR CTN TT³' | | | | | | | | | | | | | |
| | Hox4-2- | ⁵'CTY CCN TTR CTR CCI CTY GAI AA³' | | | | | | | | | | | | | |
| | Hox5+ | ⁵'ATT GGG GCT CCT TCA AGA CCT T³' | | | | | | | | | | | | | |
| | Hox5- | ⁵'TGA TGA TTC CAA AGT TTC³' | | | | | | | | | | | | | |
| | Hox6+ | ⁵'TTG GAA GAA TAC GGT TGG³' | | | | | | | | | | | | | |
| | Hox7- | ⁵'TAC TAT TTC GTC TGC TTG GG³' | | | | | | | | | | | | | |
| | Hox8- | ⁵'GAA CTC TTC CGT GGT CTC CT³' | | | | | | | | | | | | | |
| | Hox10- | ⁵'CCA CCT GCG TGT TGG GGT CT³' | | | | | | | | | | | | | |
| | Hox11+ | ⁵'CAG ATC TAC AAA ACA TGC GAG³' | | | | | | | | | | | | | |
| | Hox12- | ⁵'TGT CGC AGA CTG TAC TTG³' | | | | | | | | | | | | | |
| | Hox13- | ⁵'GAG TGT ACA CGA CAT AAA³' | | | | | | | | | | | | | |
| | Hox5'-1 | ⁵'ATG GCT ACT CTT CCC GAG AAA G³' | | | | | | | | | | | | | |

3.4 cDNA Synthesis and Polymerase Chain Reaction (PCR)

Poly-adenylated RNA was used as template in first strand cDNA synthesis reactions with commercially available kits. About 1 µg poly-adenylated RNA was reverse transcribed as described in the protocol for Maraton™ cDNA Amplification Kit (Clontech, cat. no. K1802-1) with Hox3-2– or Hox4-2– as primers. In the subsequent PCR amplification the anchor or adaptor primer of the kit was used in addition to the hexose oxidase specific primers Hox3-2– or Hox4-2–, respectively. The buffers used and the conditions for amplification was essentially as described in the protocol for the Maraton™ cDNA Amplification Kit. PCR amplification was carried out with AmpliTaq (Perkin-Elmer Cetus) using a Perkin-Elmer Thermalcycler 480™ programmed to 30 cycles at 1 min at 94° C., 2 min at 55° C. and 2 min at 72° C. Gel electrophoresis of 5 µl of the reaction mixture in a 1% agarose gel (Sea-Plaque® GTG, FMC) showed DNA fragments with approximate sizes of 600 base pairs (bp) with primer Hox4-2– and of 700 bp with primer Hox3-2–.

These DNA fragments were purified from the agarose gel using a commercially available kit (QIAEX™ Gel Extraction Kit, cat. no. 20020, QIAGEN) and about 100 ng fragment was ligated to 50 ng plasmid pT7 Blue as described in the protocol for pT7 Blue T-Vector Kit (Novagen, cat. no. 69829-1). *Escherichia coli* DH5α (Life Technologies, cat. no. 530-8258SA) or *E. coli* NovaBlue (Novagen) was transformed with the ligation mixture, and white, recombinant colonies were analyzed further.

Plasmid DNA from such colonies was purified using QIAGEN Plasmid Midi Kit (QIAGEN, cat. no. 12143) and subjected to DNA sequence analysis using Sequenase (Sequenase Version 2.0 DNA Sequencing Kit, USB). DNA sequencing reactions were subjected to acrylamide gel electrophoresis (Sequencing Gel-Mix®6, Life Technologies). DNA sequence analysis of the 700 bp fragment showed an open reading frame with a coding capacity of 234 amino acids.

Table 3.2. below shows that all the peptide sequences from the 40 kD polypeptide, i.e. HOX-2, HOX-3, HOX-4, HOX-5, and HOX-6, were found in the 234 amino acid sequence derived from this open reading frame. Thus, it was concluded that the 700 bp fragment encoded part of the hexose oxidase gene. The DNA sequence of the 600 bp fragment was shown to be identical to the proximal 600 bp of the 700 bp fragment (see Table 3.2.).

Primers Hox2-3+ and Hox3-2– were used similarly in cDNA synthesis and PCR amplification experiments. About 50 ng poly-adenylated RNA was reverse transcribed with Hox3-2– as primer as described in the protocol for 3'-Amplifinder™ RACE Kit (Clontech, cat. no. K1801-1). In the subsequent PCR amplification primers Hox2-3+ and Hox3-2– were used. The buffers used and the conditions for amplification were essentially as described for AmpliTaq polymerase (Perkin-Elmer Cetus) and in the protocol for 3'-Amplifinder™ RACE Kit. Gel electrophoresis of 5 µl of the PCR amplification mixture showed a fragment with a size of 407 bp.

This fragment was purified, inserted into plasmid pT7 Blue and sequenced as described above. The DNA sequence of this fragment was shown to be identical to the distal 407 bp of the 700 bp fragment.

The DNA sequence downstream of the 700 and 407 bp fragments was amplified with the 3'Amplifinder™ RACE Kit (Clontech) using the anchor primer of the kit as 3' primer and the hexose oxidase specific primers Hox5+ and Hox4+ as gene specific 5' primers. The buffers and the conditions for amplification were as described above. PCR and analysis of the reaction mixture on agarose gels showed a fragment with the size of about 1.3 kb. The fragment was isolated and subjected to DNA sequence analysis as described above. The DNA sequence of this 1.3 kb fragment showed an open reading frame of 357 amino acids. This 357 amino acid reading frame contained the amino acid sequences of the peptides HOX-1, HOX-3, HOX-4, HOX-5, HOX-7 and HOX-8. Therefore, it was concluded that the 1.3 kb DNA fragment encoded the 9 kD CNBr fragment, the 29 kD polypeptide, and part of the 40 kD polypeptide of hexose oxidase.

A primer specific for the 5' end of hexose oxidase, Hox5'-1, was used together with an oligo-(dT) primer to amplify the assumed entire hexose oxidase open reading frame. The gene was amplified using PCR, inserted into pT7 Blue and sequenced as described above. The DNA sequence of this 1.8 kb fragment was identical to the DNA sequences of the fragments described above with minor differences. Since these differences could be caused by misincorporations during PCR amplifications, the entire hexose oxidase gene was amplified and isolated from at least three independent PCR amplifications. Therefore, the DNA sequence presented in the below Table 3.2. is composed of at least three independently derived DNA sequences in order to exclude PCR errors in the sequence.

The amino acid sequence derived from the open reading frame on the above 1.8 kb DNA sequence is shown to contain all of the above HOX peptides, ie HOX-1 to HOX-8. Accordingly, the 1.8 kb DNA sequence codes for the above 9 kD, 29 kD and 40 kD *Chondrus crispus*-derived hexose oxidase fragments. The molecular weight of this derived open reading frame polypeptide is consistent with the assumption that the polypeptide is a subunit (possibly a monomeric fragment) of a dimeric hexose oxidase enzyme molecule.

3.5 Northern Blot Analysis of *Chondrus crispus* RNA

Total RNA isolated from *Chondrus crispus* was subjected to Northern blot analysis. RNA was purified as described above (3.1) and fractionated on a denaturing formaldehyde agarose gel and blotted onto a HybondC filter (Amersham) as described by Sambrook et al. (1989). Using the primers Hox2-3+ and Hox3-2– a 400 bp DNA fragment was synthesized by PCR as described above (3.4). This fragment was purified from a 1.2% agarose gel (SeaPlaque® GTG, FMC) and labelled with $^{32}P$ as described by Sambrook et al. (supra). This radioactive hexose oxidase specific hybridization probe was used to probe the Northern blot. The conditions for hybridization was:

3.5.1. Prehybridization at 65° C. for two hours in a buffer containing 10×Denhardt's solution (0.1 Ficoll, 0.1% polyvinylpyrrolidone, 0.1 bovine serum albumin), 2×SSC (1×SSC is 0.15 M sodium chloride, 0.015 M sodium citrate, pH 7.0), 0.1% sodium dodecyl sulfate (SDS), and 50 µg/ml denatured salmon sperm DNA.

3.5.2. Hybridization at 65° C. for at least 14 hours in a buffer containing 1×Denhardt's solution, 2×SSC, 0.1% dextran sulfate, 50 µg/ml denatured salmon sperm DNA, and $^{32}P$ labelled probe (approximately $10^6$ dpm/ml). The filter was washed twice at 65° C. for 10 minutes in 2×SSC, 0.1% SDS followed by two washes at 65° C. for 10 min in 1×SSC, 0.1% SDS. After the final wash for 10 minutes at 65° C. in 0.2×SSC, 0.1% SDS, the filter was wrapped in Saran Wrap and exposed to an X-ray film (Kodak XAR2) for two days at –80° C. using a Siemens-Titan HS intensifying screen. The resultant autoradiogram (FIG. 8) shows that a band with the approximate size of 2 kb lighted up.

TABLE 3.2

Nucleotide sequence of 1.8 kb DNA sequence
(SEQ ID NO:30) and the open reading frame for
a hexose oxidase amino acid sequence of 546 amino
acids derived from the DNA sequence (SEQ ID NO:31)

```
TGAATTCGTG GGTCGAAGAG CCCTTTGCCT CGTCTCTCTG GTACCGTGTA TGTCAAAGGT    60

TCGCTTGCAC ACTGAACTTC ACG ATG GCT ACT CTT CCT CAG AAA GAC CCC       110
                         Met Ala Thr Leu Pro Gln Lye Asp Pro
                          1               5

GGT TAT ATT GTA ATT GAT GTC AAC GCG GGC ACC GCG GAC AAG CCG GAC    158
Gly Tyr Ile Val Ile Asp Val Asn Ala Gly Thr Ala Asp Lys Pro Asp
 10              15                  20                  25

CCA CGT CTC CCC TCC ATG AAG CAG GGC TTC AAC CGC CGC TGG ATT GGA    206
Pro Arg Leu Pro Ser Met Lys Gln Gly Phe Asn Arg Arg Trp Ile Gly
             30                  35                  40

ACT AAT ATC GAT TTC GTT TAT GTC GTG TAC ACT CCT CAA GGT GCT TGT    254
Thr Asn Ile Asp Phe Val Tyr Val Val Tyr Thr Pro Gln Gly Ala Cys
             45                  50                  55

ACT GCA CTT GAC CGT GCT ATG GAA AAG TGT TCT CCC GGT ACA GTC AGG    302
Thr Ala Leu Asp Arg Ala Met Glu Lys Cys Ser Pro Gly Thr Val Arg
         60                  65                  70

ATC GTC TCT GGC GGC CAT TGC TAC GAG GAC TTC GTA TTT GAC GAA TGC    350
Ile Val Ser Gly Gly His Cys Tyr Glu Asp Phe Val Phe Asp Glu Cys
     75                  80                  85

GTC AAG GCC ATC ATC AAC GTC ACT GGT CTC GTT GAG AGT GGT TAT GAC    398
Val Lys Ala Ile Ile Asn Val Thr Gly Leu Val Glu Ser Gly Tyr Asp
 90              95                 100                 105

GAC GAT AGG GGT TAC TTC GTC AGC AGT GGA GAT ACA AAT TGG GGC TCC    446
Asp Asp Arg Gly Tyr Phe Val Ser Ser Gly Asp Thr Asn Trp Gly Ser
             110                 115                 120

TTC AAG ACC TTG TTC AGA GAC CAC GGA AGA GTT CTT CCC GGG GGT TCC    494
Phe Lys Thr Leu Phe Arg Asp His Gly Arg Val Leu Pro Gly Gly Ser
             125                 130                 135

TGC TAC TCC GTC GGC CTC GGT GGC CAC ATT GTC GGC GGA GGT GAC GGC    542
Cys Tyr Ser Val Gly Leu Gly Gly His Ile Val Gly Gly Gly Asp Gly
             140                 145                 150

ATT TTG GCC CGC TTG CAT GGC CTC CCC GTC GAT TGG CTC AGC GGC GTG    590
Ile Leu Ala Arg Leu His Gly Leu Pro Val Asp Trp Leu Ser Gly Val
 155                 160                 165

GAG GTC GTC GTT AAG CCA GTC CTC ACC GAA GAC TCG GTA CTC AAG TAT    638
Glu Val Val Val Lys Pro Val Leu Thr Glu Asp Ser Val Leu Lys Tyr
170                 175                 180                 185

GTG CAC AAA GAT TCC GAA GGC AAC GAC GGG GAG CTC TTT TGG GCA CAC    686
Val His Lys Asp Ser Glu Gly Asn Asp Gly Glu Leu Phe Trp Ala His
                 190                 195                 200

ACA GGT GGC GGT GGC GGA AAC TTT GGA ATC ATC ACC AAA TAC TAC TTC    734
Thr Gly Gly Gly Gly Gly Asn Phe Gly Ile Ile Thr Lys Tyr Tyr Phe
             205                 210                 215

AAG GAT TTG CCC ATG TCT CCA CGG GGC GTC ATC GCA TCA AAT TTA CAC    782
Lys Asp Leu Pro Met Set Pro Arg Gly Val Ile Ala Ser Asn Leu His
             220                 225                 230

TTC AGC TGG GAC GGT TTC ACG AGA GAT GCC TTG CAG GAT TTG TTG ACA    830
Phe Ser Trp Asp Gly Phe Thr Arg Asp Ala Leu Gln Asp Leu Leu Thr
         235                 240                 245

AAG TAC TTC AAA CTT GCC AGA TGT GAT TGG AAG AAT ACG GTT GGC AAG    878
Lys Tyr Phe Lys Leu Ala Arg Cys Asp Trp Lys Asn Thr Val Gly Lys
250                 255                 260                 265

TTT CAA ATC TTC CAT CAG GCA GCG GAA GAG TTT GTC ATG TAC TTG TAT    926
Phe Gln Ile Phe His Gln Ala Ala Glu Glu Phe Val Met Tyr Leu Tyr
                 270                 275                 280
```

TABLE 3.2-continued

Nucleotide sequence of 1.8 kb DNA sequence
(SEQ ID NO:30) and the open reading frame for
a hexose oxidase amino acid sequence of 546 amino
acids derived from the DNA sequence (SEQ ID NO:31)

| | |
|---|---|
| ACA TCC TAC TCG AAC GAC GCC GAG CGC GAA GTT GCC CAA GAC CGT CAC<br>Thr Ser Tyr Ser Asn Asp Ala Glu Arg Glu Val Ala Gln Asp Arg His<br>      285                      290                    295 | 974 |
| TAT CAT TTG GAG GCT GAC ATA GAA CAG ATC TAC AAA ACA TGC GAG CCC<br>Tyr His Leu Glu Ala Asp Ile Glu Gln Ile Tyr Lys Thr Cys Glu Pro<br>      300                      305                    310 | 1022 |
| ACC AAA GCG CTT GGC GGG CAT GCT GGG TGG GCG CCG TTC CCC GTG CGG<br>Thr Lys Ala Leu Gly Gly His Ala Gly Trp Ala Pro Phe Pro Val Arg<br>      315                      320                    325 | 1070 |
| CCG CGC AAG AGG CAC ACA TCC AAG ACG TCG TAT ATG CAT GAC GAG ACG<br>Pro Arg Lys Arg His Thr Ser Lys Thr Ser Tyr Met His Asp Glu Thr<br>330                    335                    340                    345 | 1118 |
| ATG GAC TAC CCC TTC TAC GCG CTC ACT GAG ACG ATC AAC GGC TCC GGG<br>Met Asp Tyr Pro Phe Tyr Ala Leu Thr Glu Thr Ile Asn Gly Ser Gly<br>                350                    355                    360 | 1166 |
| CCG AAT CAG CGC GGC AAG TAC AAG TCT GCG TAC ATG ATC AAG GAT TTC<br>Pro Asn Gln Arg Gly Lys Tyr Lys Ser Ala Tyr Met Ile Lys Asp Phe<br>            365                    370                    375 | 1214 |
| CCG GAT TTC CAG ATC GAC GTG ATC TGG AAA TAC CTT ACG GAG GTC CCG<br>Pro Asp Phe Gln Ile Asp Val Ile Trp Lys Tyr Leu Thr Glu Val Pro<br>      380                      385                    390 | 1262 |
| GAC GGC TTG ACT AGT GCC GAA ATG AAG GAT GCC TTA CTC CAG GTG GAC<br>Asp Gly Leu Thr Ser Ala Glu Met Lys Asp Ala Leu Leu Gln Val Asp<br>      395                      400                    405 | 1310 |
| ATG TTT GGT GGT GAG ATT CAC AAG GTG GTC TGG GAT GCG ACG GCA GTC<br>Met Phe Gly Gly Glu Ile His Lys Val Val Trp Asp Ala Thr Ala Val<br>410                    415                    420                    425 | 1358 |
| GCG CAG CGC GAG TAC ATC ATC AAA CTG CAG TAC CAG ACA TAC TGG CAG<br>Ala Gln Arg Glu Tyr Ile Ile Lys Leu Gln Tyr Gln Thr Tyr Trp Gln<br>                430                    435                    440 | 1406 |
| GAA GAA GAC AAG GAT GCA GTG AAC CTC AAG TGG ATT AGA GAC TTT TAC<br>Glu Glu Asp Lys Asp Ala Val Asn Leu Lys <u>Trp</u> Ile Arg Asp Phe Tyr<br>            445                    450                    455 | 1454 |
| GAG GAG ATG TAT GAG CCG TAT GGC GGG GTT CCA GAC CCC AAC ACG CAG<br>Glu Glu Met Tyr Gln Pro Tyr Gly Gly Val Pro Asp Pro Asn Thr Gln<br>            460                    465                    470 | 1502 |
| GTG GAG AGT GGT AAA GGT GTG TTT GAG GGA TGC TAC TTC AAC TAC CCG<br>Val Glu Ser Gly Lys Gly Val Phe Glu Gly Cys Tyr Phe Asn Tyr Pro<br>      475                      480                    485 | 1550 |
| GAT GTG GAC TTG AAC AAC TGG AAG AAC GGC AAG TAT GGT GCC CTC GAA<br>Asp Val Asp Leu Asn Asn Trp Lys Asn Gly Lys Tyr Gly Ala Leu Glu<br>490                    495                    500                    505 | 1598 |
| CTT TAC TTT TTG GGT AAC CTG AAC CGC CTC ATC AAG GCC AAA TGG TTG<br>Leu Tyr Phe Leu Gly Asn Leu Asn Arg Leu Ile Lys Ala Lys Trp Leu<br>            510                    515                    520 | 1646 |
| TGG GAT CCC AAC GAG ATC TTC ACA AAC AAA CAG AGC ATC CCT ACT AAA<br>Trp Asp Pro Asn Glu Ile Phe Thr Asn Lys Gln Ser Ile Pro Thr Lys<br>      525                      530                    535 | 1694 |
| CCT CTT AAG GAG CCC AAG CAG ACG AAA TAGTAGGTCA CAATTAGTCA<br>Pro Leu Lys Glu Pro Lys Gln Thr Lys<br>      540                      545 | 1741 |
| TCGACTGAAG TGCAGCACTT GTCGGATACG GCGTGATGGT TGCTTTTTAT AAACTTGGTA | 1801 |

In the amino acid sequence shown in the above Table 3.2., the HOX-1 to HOX-8 peptides are shown with bolded or underlined codes. Bolded codes indicate amino acid residues which have been confirmed by amino acid sequencing of the peptides. The underlined codes indicate amino acid residues which are derived from the nucleotide sequence, but which have not been confirmed by sequencing of the relevant HOX peptides.

HOX-1 is amino acid residues 461-468, HOX-2 residues 92-114, HOX-3 residues 219-234, HOX-4 residues 189-202, HOX-5 residues 215-218, HOX-6 residues 8-22, HOX-7 residues 434-444 and HOX-8 residues 452-460.

EXAMPLE 4

Production of Recombinant Hexose Oxidase in *Pichia pastoris*

4.1. Construction of a Vector for the Expression of Recombinant Hexose Oxidase in *Pichia pastoris*

The open reading frame encoding *Chondrus crispus* hexose oxidase as shown in Table 3.2. was inserted into a *Pichia pastoris* expression vector, pPIC3 (Research Corporation Technologies, Inc., Tucson, Ariz. 85711-3335). The plasmid contains the alcohol oxidase promotor (aox1 promotor) and transcriptional termination signal from *Pichia pastoris* (in FIG. 9, aoxp and aoxt, respectively). A his4$^+$ gene in the vector enables selection of His$^+$ recombinant *Pichia pastoris* cells. When this expression cassette is transformed into *Pichia pastoris* it integrates into the chromosomal DNA. *Pichia pastoris* cells harbouring an expression cassette with a *Chondrus crispus* hexose oxidase gene inserted downstream of the aox1 promotor can be induced to produce hexose oxidase by the addition of the inducer of the aox1 promotor, methanol. A mutant of *Pichia pastoris*, KM71, which is defective in the major alcohol oxidase gene, aox1, can be used as recipient of the hexose oxidase gene (Cregg and Madden 1987; Tschopp et al. 1987). However, *Pichia pastoris* contains another alcohol oxidase gene, aox2, which can also be induced by methanol. Thus, recombinant *Pichia pastoris* transformed with a hexose expression cassette will produce two oxidases, hexose oxidase and alcohol oxidase, upon addition of methanol.

Before insertion of the hexose oxidase gene into the expression vector pPIC3, sequences 5' and 3' of the open reading were modified. First strand cDNA was used as template in PCR. The synthetic oligonucleotide specific for the 5'-end of the open reading frame, Hox5'-1 (Table 3.1) was used as PCR-primer together with a primer (Hox3'-1) specific for the 3'-end of the sequence encoding *Chondrus crispus* hexose oxidase. The primer Hox3'-1 had the sequence 5'-ACCAAGTTTATAAAAAGCAACCATCAC-3' (SEQ ID NO:32). PCR amplification was carried out using the GeneAmp® PCR Reagent Kit with AmpliTaq® DNA polymerase (Perkin-Elmer Cetus). The PCR program was 30 cycles at 30 sec at 94° C., 30 sec. at 55° C. and 2 min at 72° C. Gel electrophoresis of the reaction mixture showed a band with the approximate size of 1.7 kb. This 1.7 kb fragment was inserted into the vector pT7 Blue (Novagen) (plasmid pUPO150) and subjected to DNA sequencing.

The fragment encoding *Chondrus crispus* hexose oxidase was further subcloned into the *Pichia pastoris* expression vector pPIC3 (Clare et al. 1991) as shown in FIG. 9. Plasmid pT7 Blue harbouring the hexose oxidase gene was restricted with the restriction endonuclease NdeI and the ends were polished with Klenow DNA polymerase essentially as described by Sambrook et al. (1989). After heat inactivation of the DNA polymerase (Sambrook et al. 1989) the DNA was restricted further with EcoRI and the DNA fragment containing the hexose oxidase gene was purified on an agarose gel as a blunt end—EcoRI DNA fragment (QIAEX™, QIAGEN).

The *Pichia pastoris* expression vector pPIC3 was restricted with the restriction enzymes SnaBI and EcoRI and purified on an agarose gel. The purified vector and the fragment encoding hexose oxidase were ligated and the ligation mixture was transformed into *E. coli* DH5α (Life Technologies), essentially as described by Sambrook et al. (1989). The resulting expression vector containing the hexose oxidase gene from *Chondrus crispus*, plasmid pUPO153, was subjected to DNA sequencing to ensure that no mutations had occurred in the hexose oxidase gene during the subcloning procedure.

Plasmid pUPO153 was purified from *E. coli* DH5α and introduced into *Pichia pastoris* using electroporation (The Pichia Yeast Expression System, Phillips Petroleum Company) or using The Pichia Spheroplast Module (Invitrogen, San Diego, USA, cat. no. K1720-01). The methanol-utilization-defective mutant of *Pichia pastoris*, KM71 (genotype his4, aox1::ARG4), (Cregg and Madden 1987; Tschopp et al. 1987) was used as recipient. Recombinant *Pichia pastoris* colonies selected on agar plates without histidine were screened for the presence of the hexose oxidase gene using PCR. Primers specific for hexose oxidase (Table 3.1) were used in addition to primers specific for the *Pichia pastoris* alcohol oxidase promoter and transcription termination signal (Invitrogen, cat. nos. N710-02 and N720-02, respectively).

A sample of *Pichia pastoris* KM71 containing pUPO153 was deposited with the Deutsche Sammlung von Mikroorganismen und Zellkulturen GmbH (DSM), Mascheroder Weg 1b, D-38124 Braunschweig, Germany on 23 May 1996 under the accession number DSM 10693.

4.2. Expression of Recombinant Hexose Oxidase in *Pichia pastoris*

*Pichia pastoris* strain KM71 containing the expression cassette with the hexose oxidase gene inserted between the aox1 promoter and the transcription termination signal was cultivated in shake flasks in MD (1.34 grams per liter of yeast nitrogen base (Difco, cat. no. 0919-15-3), 0.4 mg/l of biotin, 0.1% arginine, and 20 g/l glucose). One-liter shake flasks containing 150 ml culture were incubated in a rotary shaker at 30° C., 300 rpm. When the cells reached a density of $OD_{600}$=15-20 the cells were harvested by centrifugation at 6,000×g for 10 min and resuspended in a similar volume (150 ml) of induction medium, MM (1.34 g/l of yeast nitrogen base, 0.4 mg/l of biotin, 0.1% arginine, and 1% methanol). After growth for two days, additional methanol (0.5%) was added to compensate for the consumption and evaporation of methanol.

Three or four days after induction the cells were harvested by centrifugation (6,000×g, 10 min) and resuspended in about ⅕ of the growth volume of 50 mM Tris-Cl, pH 7.5. Resuspended cells were kept cold until disrupture in a FRENCH® Press (SLM Instruments, Inc., Rochester, N.Y.). Cells were opened in a 20K FRENCH® Pressure Cell at an internal pressure of 20,000 psi. The cell extract was cleared by centrifugation at 10,000×g for 10 min at 5° C. The hexose oxidase containing supernatant was carefully removed and subjected to purification as described below.

4.3. Purification of Recombinant Hexose Oxidase from *Pichia pastoris*

4.3.1. First Step, Anion Exchange Chromatography.

Clarified homogenate from FRENCH press homogenization (100-150 ml) was subjected to anion exchange chromatography on an FPLC system equipped with two 5-ml HiTrap-Q columns prepacked with Q-Sepharose High Performance (Pharmacia). The columns were connected in series and the chromatography was carried out at room temperature. The column was equilibrated in buffer A: 20 mM Tris-Cl, pH 7.5. The flow rate was 1.25 ml during sample application and 2.5 ml during wash and elution. After sample application the column was washed with 30 ml of buffer A. Adsorbed proteins were then eluted with 200 ml of a gradient from buffer A to buffer B: 20 mM Tris-Cl, 750 mM NaCl, pH 7.5. Fractions of 2 ml were collected during wash and gradient elution. The fractions were assayed for hexose oxidase activity as described above in Example 1.3 (10 μl of sample, 15 min of incubation time). The fractions were also assayed for alcohol oxidase (AOX) activity in an assay which was identical to the hexose oxidase assay except that 0.5% methanol instead of 0.05 M glucose was used as substrate. As seen in FIG. 10, the activity profiles showed that AOX and HOX co-eluted at a salt concentration of about 400 mM NaCl. Fractions containing hexose oxidase were pooled and stored at 4° C.

4.3.2. Second Step, Gel Filtration.

The pool from step one in the purification (20-30 ml) was concentrated to about 3.5 ml by centrifugal ultracentrifugation at 4° C. in Centriprep concentrators (Amicon, USA, nominal molecular weight cut-off 30,000). The concentrated preparation of hexose oxidase was clarified by centrifugation and the supernatant was mixed with glycerol to a final concentration of 5%. The sample was applied onto the column using an SA-5 sample applicator (Pharmacia) connected to the inlet of the column. Gel filtration was carried out at 4° C. on an XK 26/70 column (2.6×66 cm, Pharmacia) with a bed volume of 350 ml. The column was packed with Sephacryl S-200 HR (Pharmacia) according to the instructions of the manufacturer. The buffer was 20 mM Tris-Cl, 500 mM NaCl, pH 7.5 and the peristaltic P1-pump (Pharmacia) was set at 0.5 ml/min. The UV-absorbance at 280 nm was recorded. Fractions of 2.5 ml were collected and assayed for hexose oxidase and alcohol oxidase activity as described above (10 μl of sample, 15 min of incubation time). The activity profiles clearly showed that AOX and HOX activities were separated, see FIG. 11. This result of the gel filtration was expected since alcohol oxidase from methylotrophic yeasts like *Pichia pastoris* have a native molecular weight of about 600,000 (Sahm & Wagner, 1973), whereas HOX has a native molecular weight of about 110,000-130,000, as described in section 1.8. The elution volume of recombinant HOX was identical to the elution volume observed earlier on the same column for native HOX from *Chondrus crispus* (section 1.7 and 1.8). Thus, recombinant HOX appeared to be of the same molecular weight as native HOX isolated directly from *Chondrus crispus*. Fractions containing hexose oxidase were pooled and stored at 4° C.

4.4.3. Third Step, Anion Exchange Chromatography on Mono Q Column.

The pool from the above second step was further purified by anion exchange chromatography on a FPLC system equipped with a Mono Q HR 5/5 column (bed volume 1 ml). The column was equilibrated in buffer A: 20 mM Tris-Cl, pH 7.5. The flow rate was 1 ml/min. The pool from step two was desalted by gel filtration in buffer A on pre-packed Sephadex G-25 columns (PD-10, Pharmacia). After sample application the column was washed with 30 ml of buffer A. Adsorbed proteins were eluted with 20 ml of a gradient from 0% to 100% buffer B: 20 mM Tris-Cl, 500 mM NaCl, pH 7.5. Fractions of 0.5 ml were collected and assayed for hexose oxidase activity as described above (10 μl of sample, 15 min of incubation time). Fractions containing hexose oxidase were pooled and stored at 4° C.

4.3.4. Fourth Step, Chromatofocusing.

The pool from the above third step was purified by chromatofocusing on a Mono P HR 5/5 column as described above in Example 1.13, except that the Phenyl Sepharose adsorption step was omitted. When comparing native and recombinant hexose oxidase—both forms obtained by a final purification by chromatofocusing—it was found that the specific activity of recombinant hexose oxidase from *Pichia pastoris* was similar to that of the native form isolated from *Chondrus crispus*. Fractions containing hexose oxidase were analyzed by SDS-PAGE and staining of the gel with Coomassie Brilliant Blue R-250 as described above. The purified preparation of recombinant hexose oxidase was composed of two bands migrating at 40 kD and 29 kD, respectively.

In conclusion, recombinant hexose oxidase could be isolated and purified from the host organism *Pichia pastoris*. In SDS-PAGE the recombinant, purified enzyme exhibited the same bands at 40 kD and 29 kD as the corresponding native enzyme from *Chondrus crispus*.

4.4. Properties of Recombinant Hexose Oxidase from *Pichia pastoris*

Generation and amino acid sequence analysis of peptide fragments of recombinant hexose oxidase (rHOX).

Purified rHOX was used for preparative SDS-PAGE and electroblotting to PVDF membrane, as described above in Example 2.4. The resulting 40 kD and 29 kD bands were subjected to enzymatic digestion of PVDF-bound hexose oxidase polypeptides, as described above in Example 2.5. The peptide fragments were separated by reversed-phase liquid chromatography as described above in Example 2.7. Well-resolved and abundant peptides were selected for amino acid sequence analysis by automated Edman degradation (10 steps), as described above in Example 2.3. The obtained amino acid sequences are shown in Table 4.1.

TABLE 4.1

Peptide sequences obtained by sequence analysis of endoproteinase Lys-C peptides derived from 40 kD and 29 kD polypeptides of recombinant hexose oxidase expressed in *Pichia pastoris*

| Origin of sequenced peptide | Sequence identification | Amino acid sequence | | | | | | | | | | |
|---|---|---|---|---|---|---|---|---|---|---|---|---|
| | | Step no | 1 | 2 | 3 | 4 | 5 | 6 | 7 | 8 | 9 | 10 |
| 40 kD | HOX-9 peptide | | D | P | G | Y | I | V | I | D | V | N | (SEQ ID NO:35) |
| 29 kD | Hox-10 peptide | | L | Q | Y | Q | T | Y | W | Q | E | E | (SEQ ID NO:36) |

TABLE 4.1-continued

Peptide sequences obtained by sequence analysis
of endoproteinase Lys-C peptides derived from
40 kD and 29 kD polypeptides of recombinant
hexose oxidase expressed in Pichia pastoris Origin of
sequenced Sequence
peptide  identification  Amino acid sequence

```
                        and and and and and and and and and and
                         Y   L   T   E   V   P   D   G   L   T    (SEQ ID NO:37)
```

The HOX-9 peptide sequence from the recombinant 40 kD polypeptide showed a sequence identical to $Aspx_8$ through $Asn_{17}$ in the amino acid sequence of hexose oxidase from *Chondrus crispus* as shown in Table 3.2. (SEQ ID NO:30). Sequence analysis of a peptide sample obtained from the recombinant 29 kD polypeptide showed two residues at each step. The amino acid identifications showed that two peptides present in the sample correspond to $Leu_{434}$ through $Glu_{443}$ and $Tyr_{388}$ through $Thr_{397}$, respectively, in the amino acid sequence of hexose oxidase from *Chondrus crispus*, see Table 3.2. (SEQ ID NO:30).

It could thus be concluded that the peptide sequences obtained from recombinant hexose oxidase were identical to the corresponding amino acid sequence of native hexose oxidase from *Chondrus crispus*.

Furthermore, it could be concluded that *Pichia pastoris* transformed with the hexose oxidase gene from *Chondrus crispus* was capable of producing recombinant hexose oxidase.

4.4.1. Substrate Specificity

The substrate specificity of recombinant hexose oxidase from *Pichia pastoris* and native hexose oxidase from *Chondrus crispus* was compared using a number of sugars at a final concentration of 0.1 M in the assay described above. The relative rates are shown in Table 4.2.

TABLE 4.2

Substrate specificity of recombinant hexose oxidase expressed in
*Pichia pastoris* and native hexose oxidase from *Chondrus crispus*

| Substrate | Relative rate | | |
|---|---|---|---|
| | recombinant enzyme | native enzyme, this work | native enzyme, Sullivan and Ikawa, 1973 |
| D-Glucose | 100 | 100 | 100 |
| D-Galactose | 75 | 75 | 82 |
| Maltose | 57 | 37 | 40 |
| Cellobiose | 51 | 33 | 32 |
| Lactose | 38 | 25 | 22 |

As shown in Table 4.2., the substrate specificity of recombinant hexose oxidase was almost identical to that of the native enzyme. However, although the relative rate among disaccharides decreased for both enzyme forms in the order maltose, cellobiose and lactose, the recombinant enzyme appeared to be less selective in its ability to oxidize these disaccharides. The results for the native enzyme were almost identical to the data reported earlier by Sullivan et al. (1973).

4.4.2. Inhibition by Sodium Diethyldithiocarbamate

Sullivan and Ikawa (1973) reported that hexose oxidase from *Chondrus crispus* is strongly inhibited by sodium diethyldithiocarbamate. Recombinant hexose oxidase from *Pichia pastoris* was compared to the native enzyme from *Chondrus crispus* with respect to inhibition by this copper-binding compound. The inhibitor was included in the enzyme assay in two concentrations, 0.1 mM and 0.01 mM, as described by Sullivan and Ikawa (1973). The results are summarized in Table 4.3.

TABLE 4.3

Comparison of the inhibitory effect of sodium diethyldithiocarbamate
on the enzymatic activity of recombinant hexose oxidase from
*Pichia pastoris* and native hexose oxidase from *Chondrus crispus*

| Concentration of inhibitor | Inhibition (%) | |
|---|---|---|
| | Recombinant enzyme | Native enzyme |
| 0.1 mM | 96 | 95 |
| 0.01 mM | 39 | 41 |

It appears from Table 4.3 that recombinant and native hexose oxidase were equally sensitive when subjected to inhibition by sodium diethyldithiocarbamate. Furthermore, the results were similar to the data for native hexose oxidase reported by Sullivan and Ikawa (1973).

EXAMPLE 5

Production of Recombinant Hexose Oxidase in Escherichia Coli 5.1. Construction of a Vector for the Expression of Recombinant Hexose Oxidase in *Escherichia coli*

The open reading frame encoding *Chondrus crispus* hexose oxidase shown in Table 3.2. (SEQ ID NO:30) was inserted into an *Escherichia coli* expression vector, pET17b (Novagen, cat. no. 69726-1). The plasmid contains a strong inducible bacteriophage T7 promotor and a T7 transcription termination signal. Genes inserted between these controlling elements can be expressed by the addition of isopropyl β-D-thiogalactopyranoside (IPTG) if the plasmid is propagated in special *E. coli* host cells e.g. strain BL21(DE3) (Novagen, cat. no. 69387-1).

The hexose oxidase gene was modified at the 5' and 3' ends in order to insert the gene in the expression vector pET17b. The hexose oxidase gene was isolated by PCR with primers specific for the 5' and 3' ends of the hexose oxidase gene. The 5' primer (Hox5'-2) had the DNA sequence 5'-ATGAAT-TCGTGGGTCGAAGAGCCC-3' (SEQ ID NO:33) and the primer specific for the 3'-end was Hox3'-1. First strand cDNA from *Chondrus crispus* was used as template. PCR amplification was carried out with AmpliTaq® DNA polymerase (Perkin-Elmer Cetus) as described in example 4.1. Gel electrophoresis of the reaction mixture showed a band with the approximate size of 1.7 kb. This 1.7 kb fragment was inserted into the vector pT7 Blue (Novagen) giving rise to plasmid pUPO161.

Modification of the 5'-end of the hexose oxidase gene and further subcloning of the gene into the *E. coli* expression vector is shown in FIG. 12. The 5'-end was modified by PCR in order to insert a NdeI site right at the ATG translation start. The oligonucleotide, Hox5'-4, with the sequence 5'-CAG-GAATTCATATGGCTACTCTTCCCCAGAAAG-3' (SEQ ID NO:34) was used together with the oligonucleotide Hox13-(SEQ ID NO:28) (Table 3.1). PCR amplification was as described above in Example 4.1. The reaction mixture was fractionated on a 2% agarose gel and the hexose oxidase specific 180 bp fragment was purified as described in Example 3.4. The 180 bp fragment was restricted with the restriction endonuclease ClaI and EcoRI and ligated to pUPO161 restricted with the same enzymes giving rise to plasmid pUPO167.

The hexose oxidase gene in plasmid pUPO167 was further sub-cloned in order to construct a hexose oxidase expression vector for *E. coli*. Plasmid pUPO167 was restricted with the enzymes NdeI and BamHI and with the enzymes BamHI and SalI. The first reaction gave rise to a 1.6 kb fragment encoding the 5' and the middle part of the hexose oxidase gene while the reaction with the enzymes BamHI and SalI gave a 200 bp fragment encoding the 3' end of the hexose oxidase gene. The two hexose oxidase specific fragments were purified on agarose gels as described in Example 3.4 and ligated to plasmid pET17b restricted with the restriction endonucleases NdeI and XhoI. Plasmid pET17b harbouring the hexose oxidase gene was denoted pUPO181. DNA sequencing showed that no mutation was introduced in the hexose oxidase gene during the isolation and cloning process.

5.2. Expression of Recombinant Hexose Oxidase in *Escherichia coli*

Plasmid pUPO181 was introduced into *E. coli* strain BL21 (DE3) (Novagen) by a standard transformation procedure (Sambrook et al. 1989). The cells were grown in shake flasks in LB medium (Sambrook et al. supra). At a cell density of $OD_{600}=0.5$ the cells were induced to express recombinant hexose oxidase by the addition of $10^{-3}$ M IPTG. One hour after the addition of IPTG the cells were harvested by centrifugation and resuspended in sample buffer and subjected to SDS-PAGE as described above in Example 1.10.

The result of the electrophoresis is shown in FIG. 13. The crude extract of *E. coli* expressing recombinant hexose oxidase enzyme from plasmid pUPO181 showed a prominent protein band at Mr 62 kD. This 62 kD band had the same molecular weight as the translation product predicted from the open reading frame. Non-transformed *E. coli* cells showed no such 62 kD protein.

A sample of *E. coli* BL21(DE3) containing pUPO181 was deposited with the Deutsche Sammlung von Mikroorganismen und Zellkulturen GmbH (DSM), Mascheroder Weg 1b, D-38124 Braunschweig, Germany on 23 May 1996 under the accession number DSM 10692.

EXAMPLE 6

Production of Recombinant Hexose Oxidase in Saccharomyces cerevisiae 6.1. Construction of a Vector for the Expression of Recombinant Hexose Oxidase in *Saccharomyces cerevisiae*

The open reading frame encoding *Chondrus crispus* hexose oxidase shown in Table 3.2. (SEQ ID NO:30) was inserted into a yeast expression vector, pYES2 (Invitrogen, cat. no. V825-20). Plasmid pYES2 is a high-copy number episomal vector designed for inducible expression of recombinant proteins in *Saccharomyces cerevisiae*. The vector contains upstream activating and promoter sequences from the *S. cerevisiae* Gal1 gene for high-level, tightly regulated transcription. The transcription termination signal is from the CYC1 gene.

The hexose oxidase gene from *Chondrus crispus* was modified at the 5'- and 3'-ends in order to insert the gene in the expression vector pYES2. The hexose oxidase gene was isolated from plasmid pUPO150 as described in Example 4.1 (FIG. 9). The hexose oxidase gene was isolated on a blunt end-EcoRI DNA fragment as described and inserted into plasmid pYES2 restricted with the enzymes PvuII and EcoRI (FIG. 14). The resulting plasmid, pUPO155, was subjected to DNA sequencing in order to show that no mutation had occurred during the cloning procedure.

Plasmid pUPO155 was purified from *E. coli* DH5α and trans-formed into *S. cerevisiae* by electroporation (Grey and Brendel 1992). The strain PAP1500 (genotype α, ura3-52, trp1::GAL10-GAL4, lys2-801, leu2Δ1, his3Δ200, pep4:: HIS3, prb1Δ1.6R, can1, GAL) (Pedersen et al. 1996) was used as a recipient.

6.2. Expression of Recombinant Hexose Oxidase in Saccharomyces cerevisiae

*S. cerevisiae* strain 1500 containing plasmid pUPO155 was grown and induced with 2% galactose as described by Pedersen et al. (1996). Three days after the induction the cells were harvested by centrifugation and lysed as described above in Example 4.2. The crude extract was assayed for hexose oxidase activity using the o-dianisidine assay described above in Example 1.3. Table 6.1 shows that *S. cerevisiae* cells harbouring the hexose oxidase gene are capable of expressing active hexose oxidase.

TABLE 6.1

Production of recombinant hexose oxidase in *Saccharomyces cerevisiae*

| Substrate | Saccharomyces cerevisiae | |
|---|---|---|
| | +hexose oxidase gene | non-recombinant control |
| D-Glucose | ++ | 0 |
| D-Galactose | + | 0 |
| no substrate | 0 | 0 |

0 = no detectable activity

A sample of *S. cerevisiae* strain 1500 containing plasmid pUPO155 was deposited with the Deutsche Sammlung von Mikroorganismen und Zellkulturen GmbH (DSM), Mascheroder Weg 1b, D-38124 Braunschweig, Germany on 23 May 1996 under the accession number DSM 10694.

REFERENCES

1. Barkholt, V. and A. L. Jensen 1989. Amino Acid Analysis: Determination of Cysteine plus Half-Cystine in Proteins after Hydrochloric Acid Hydrolysis with a Disulfide Compound as Additive. Analytical Biochemistry 177:318-322.
2. Bean, R. C. and W. Z. Hassid 1956. J. Biol. Chem. 218: 425-436.
3. Clare, J J., F. B. Rayment, S. P. Ballantine, K. Sreekrishna and M. A. Romanos 1991. High-level expression of tetanus toxin fragment C in *Pichia pastoris* strains containing multiple tandem integrations of the gene. Bio/Technology 9: 455-460.

4. Cregg, J. M. and K. N. Madden 1987. Development of transformation systems and construction of methanol-utilisation-defective mutants of *Pichia pastoris* by gene disruption. In: Biological Research on Industrial Yeast, Vol III. Stewart, G. G. et al. (Eds.). pp 1-18. CRC Press, Boca Raton, Fla.
5. Fernandez, J. et al. 1992. Internal Protein Sequence Analysis: Enzymatic Digestion for Less Than 10 μg of Protein Bound to Polyvinylidene Difluoride or Nitrocellulose Membranes. Analytical Biochemistry, 201:255-264.
6. Fernandez, J. et al. 1994. An Improved Procedure for Enzymatic Digestion of Polyvinylidene Difluoride-Bound Proteins for Internal Sequence Analysis. Analytical Biochemistry, 218:112-117.
7. Groppe, J. C. and D. E. Morse 1993. Isolation of full-length RNA templates for reverse transcription from tissues rich in RNase and proteoglycans, Anal. Biochem., 210:337-343.
8. Kerschensteiner, D. A. and G. L. Klippenstein 1978. Purification, Mechanism, and State of Copper in Hexose Oxidase. Federation Proceedings 37:1816 abstract.
9. Laemmli, U. K. 1970. Cleavage of Structural Proteins during the Assembly of the Head of Bacteriophage T4. Nature (London) 227:680-685.
10. Pedersen P. A., J. H. Rasmussen, and P. L. Jorgensen. 1996. Expression in high yield of pig α1β1 Na, K-ATPase and inactive mutants D369N and D807N in *Saccharomyces cerevisiae*. J. Biol. Chem. 271: 2514-2522.
11. Rand, A. G. 1972. Direct enzymatic conversion of lactose to acid: glucose oxidase and hexose oxidase. Journal of Food Science 37:698-701.
12. Sahm, H. and Wagner, F. 1973. Microbial assimilation of methanol. Eur. J. Biochem. 36: 250-256.
13. Sambrook, J., E. F. Fritsch and T. Maniatis 1989. Molecular Cloning, A Laboratory Manual 2nd Ed. Cold Spring Harbor Laboratory Press, Cold Spring Harbor, N.Y.
14. Schagger, H. and G. von Jagow 1987. Tricine-Sodium Dodecyl Sulfate-Polyacrylamide Gel Electrophoresis for the Separation of Proteins in the Range from 1 to 100 kDa. Analytical Biochemistry 166:368-379.
15. Sock, J. and R. Rohringer 1988. Activity Staining of Blotted Enzymes by Reaction Coupling with Transfer Membrane-Immobilized Auxiliary Enzymes. Analytical Biochemistry 171:310-319.
16. Sullivan, J. D. and M. Ikawa 1973. Purification and Characterization of Hexose Oxidase from the red Alga *Chondrus crispus*. Biochemica et Biophysica Acta 309:11-22.
17. Tschopp, J. F., G. Sverlow, R. Kosson, W. Craig, and L. Grinna 1987. High-level secretion of glycosylated invertase in the methylotrophic yeast, *Pichia pastoris*. Bio/Technology 5: 1305-1308.
18. Yeh, K-W, R. H. Juang and J-C. Su. A rapid and efficient method for RNA isolation from plants with high carbohydrate content. Focus 13:102-103

The invention claimed is:

1. A dough wherein said dough comprises a polypeptide having hexose oxidase activity, or a microbial cell comprising a recombinant DNA fragment coding for said polypeptide having hexose oxidase activity; wherein said polypeptide having hexose oxidase activity is encoded by a nucleic acid sequence isolated by hybridization with the nucleic acid sequence set forth in SEQ ID NO:30 under stringent conditions comprising (1) hybridization at 65° C. for at least 14 hours in a buffer containing 1×Denhardt's solution, 2×SSC, 0.1% dextran sulfate, 50 μg/ml denatured salmon sperm DNA, followed by (2) two washes at 65° C. for 10 minutes in 2×SSC, 0.1% SDS, and followed by (3) two washes at 65° C. for 10 min in 1×SSC, 0.1% SDS.

2. A dough according to claim 1 wherein said polypeptide having hexose oxidase activity comprises at least one amino acid sequence selected from the group consisting of (i) Tyr-Glu-Pro-Tyr-Gly-Gly-Val-Pro, (SEQ ID NO:1)

(ii) Ala-Ile-Ile-Asn-Val-Thr-Gly-Leu-Val-Glu-Ser-Gly-Tyr-Asp-X-X-X-Gly-Tyr-X-Val-Ser-Ser, (SEQ ID NO:2)

(iii) Asp-Leu-Pro-Met-Ser-Pro-Arg-Gly-Val-Ile-Ala-Ser-Asn-Leu-X-Phe, (SEQ ID NO:3)

(iv) Asp-Ser-Glu-Gly-Asn-Asp-Gly-Glu-Leu-Phe-X-Ala-His-Thr, (SEQ ID NO:4)

(v) Tyr-Tyr-Phe-Lys, (SEQ ID NO:5)

(vi) Asp-Pro-Gly-Tyr-Ile-Val-Ile-Asp-Val-Asn-Ala-Gly-Thr-X-Asp, (SEQ ID NO:6)

(vii) Leu-Gln-Tyr-Gln-Thr-Tyr-Trp-Gln-Glu-Glu-Asp, (SEQ ID NO:7) and (viii) X-Ile-Arg-Asp-Phe-Tyr-Glu-Glu-Met, (SEQ ID NO:8)

where X represents an amino acid selected from the group consisting of Ala, Arg, Asn, Asp, Cys, Gln, Glu, Gly, His, Ile, Leu, Lys, Met, Phe, Pro, Ser, Thr, Trp, Tyr and Val.

3. A dough according to claim 1 wherein said polypeptide having hexose oxidase activity comprises amino acid sequences:

(i) Tyr-Glu-Pro-Tyr-Gly-Gly-Val-Pro, (SEQ ID NO:1)

(ii) Ala-Ile-Ile-Asn-Val-Thr-Gly-Leu-Val-Glu-Ser-Gly-Tyr-Asp-X-X-X-Gly-Tyr-X-Val-Ser-Ser, (SEQ ID NO:2)

(iii) Asp-Leu-Pro-Met-Ser-Pro-Arg-Gly-Val-Ile-Ala-Ser-Asn-Leu-X-Phe, (SEQ ID NO:3)

(iv) Asp-Ser-Glu-Gly-Asn-Asp-Gly-Glu-Leu-Phe-X-Ala-His-Thr, (SEQ ID NO:4)

(v) Tyr-Tyr-Phe-Lys, (SEQ ID NO:5)

(vi) Asp-Pro-Gly-Tyr-Ile-Val-Ile-Asp-Val-Asn-Ala-Gly-Thr-X-Asp, (SEQ ID NO:6)

-continued

```
                                                   (SEQ ID NO:7)
(vii)   Leu-Gln-Tyr-Gln-Thr-Tyr-Trp-Gln-Glu-Glu-Asp,
and (SEQ ID NO:8)
(viii)  X-Ile-Arg-Asp-Phe-Tyr-Glu-Glu-Met,
``` where X represents an amino acid selected from the group consisting of Ala, Arg, Asn, Asp, Cys, Gln, Glu, Gly, His, lie, Leu, Lys, Met, Phe, Pro, Ser, Thr, Trp, Tyr and Val.

4. The dough according to claim 1 wherein said polypeptide having hexose oxidase activity comprises the amino acid sequence shown as SEQ ID No 31.

5. The dough according to claim 1 wherein said recombinant DNA fragment coding for a polypeptide having hexose oxidase activity is derived from a marine algal species, a plant species or a microbial species or is constructed synthetically.

6. The dough according to claim 1 wherein said microbial cell is a yeast cell.

7. The dough according to claim 1 wherein said microbial cell is a *Saccharomyces cerevisiae* cell or a *Pichia pastoris* cell.

8. The dough according to claim 1 wherein said dough further comprises at least one dough or bakery product improving enzyme.

9. The dough according to claim 1 wherein said dough further comprises at least one dough or bakery product improving enzyme and wherein said dough or bakery product improving enzyme is selected from the group consisting of a cellulase, a hemicellulase, a pentosanase, a lipase, a xylanase, an amylase, a glucose oxidase and a protease.

10. A food or feed product manufactured by the use of a polypeptide having hexose oxidase activity or a microbial cell comprising a recombinant DNA fragment coding for said polypeptide having hexose oxidase activity; wherein said polypeptide having hexose oxidase activity is encoded by a nucleic sequence isolated by hybridization with the nucleic acid sequence set forth in SEQ ID NO:30 under stringent conditions comprising
   (1) hybridization at 65° C. for at least 14 hours in a buffer containing 1×Denhardt's solution, 2×SSC, 0.1% dextran sulfate, 50 µg/ml denatured salmon sperm DNA, followed by
   (2) two washes at 65° C. for 10 minutes in 2×SSC, 0.1% SDS, and followed by
   (3) two washes at 65° C. for 10 min in 1×SSC, 0.1% SDS.

11. A food or feed product according to claim 10 wherein said polypeptide having hexose oxidase activity comprises at least one amino acid sequence selected from the group consisting of

```
                                                   (SEQ ID NO:1)
(i)     Tyr-Glu-Pro-Tyr-Gly-Gly-Val-Pro, (SEQ ID NO:2)
(ii)    Ala-Ile-Ile-Asn-Val-Thr-Gly-Leu-Val-Glu-Ser-

Gly-Tyr-Asp-X-X-X-Gly-Tyr-X-Val-Ser-Ser, (SEQ ID NO:3)
(iii)   Asp-Leu-Pro-Met-Ser-Pro-Arg-Gly-Val-Ile-Ala- Ser-Asn-Leu-X-Phe, (SEQ ID NO:4)
(iv)    Asp-Ser-Glu-Gly-Asn-Asp-Gly-Glu-Leu-Phe-X-

Ala-His-Thr, (SEQ ID NO:5)
(v)     Tyr-Tyr-Phe-Lys, (SEQ ID NO:6)
(vi)    Asp-Pro-Gly-Tyr-Ile-Val-Ile-Asp-Val-Asn-Ala-

Gly-Thr-X-Asp, (SEQ ID NO:7)
(vii)   Leu-Gln-Tyr-Gln-Thr-Tyr-Trp-Gln-Glu-Glu-Asp,
and (SEQ ID NO:8)
(viii)  X-Ile-Arg-Asp-Phe-Tyr-Glu-Glu-Met,
``` where X represents an amino acid selected from the group consisting of Ala, Arg, Asn, Asp, Cys, Gln, Glu, Gly, His, lie, Leu, Lys, Met, Phe, Pro, Ser, Thr, Trp, Tyr and Val.

12. A food or feed product according to claim 10 wherein said polypeptide having hexose oxidase activity comprises amino acid sequences

```
                                                   (SEQ ID NO:1)
(i)     Tyr-Glu-Pro-Tyr-Gly-Gly-Val-Pro, (SEQ ID NO:2)
(ii)    Ala-Ile-Ile-Asn-Val-Thr-Gly-Leu-Val-Glu-Ser-

Gly-Tyr-Asp-X-X-X-Gly-Tyr-X-Val-Ser-Ser, (SEQ ID NO:3)
(iii)   Asp-Leu-Pro-Met-Ser-Pro-Arg-Gly-Val-Ile-Ala- Ser-Asn-Leu-X-Phe, (SEQ ID NO:4)
(iv)    Asp-Ser-Glu-Gly-Asn-Asp-Gly-Glu-Leu-Phe-X-

Ala-His-Thr, (SEQ ID NO:5)
(v)     Tyr-Tyr-Phe-Lys, (SEQ ID NO:6)
(vi)    Asp-Pro-Gly-Tyr-Ile-Val-Ile-Asp-Val-Asn-Ala-

Gly-Thr-X-Asp, (SEQ ID NO:7)
(vii)   Leu-Gln-Tyr-Gln-Thr-Tyr-Trp-Gln-Glu-Glu-Asp,
and (SEQ ID NO:8)
(viii)  X-Ile-Arg-Asp-Phe-Tyr-Glu-Glu-Met,
``` where X represents an amino acid selected from the group consisting of Ala, Arg, Asn, Asp, Cys, Gln, Glu, Gly, His, lie, Leu, Lys, Met, Phe, Pro, Ser, Thr, Trp, Tyr and Val.

13. The food or feed product according to claim 10 wherein said polypeptide having hexose oxidase activity comprises the amino acid sequence shown as SEQ ID No 31.

14. The food or feed product according to claim 10 wherein said recombinant DNA fragment coding for a polypeptide having hexose oxidase activity is derived from a marine algal species, a plant species or a microbial species or is constructed synthetically.

15. The food or feed product according to claim 10 wherein said microbial cell is a yeast cell.

16. The food or feed product according to claim 10 wherein said microbial cell is a 10 *Saccharomyces cerevisiae* cell or a *Pichia pastoris* cell.

17. The food or feed product according to claim 10 wherein said dough further comprises at least one dough or bakery product improving enzyme.

18. The food or feed product according to claim 10 wherein said dough further comprises at least one dough or bakery product improving enzyme and wherein said dough or bakery product improving enzyme is selected from the group consisting of a cellulase, a hemicellulase, a pentosanase, a lipase, a xylanase, an amylase, a glucose oxidase and a protease.

19. The food product according to claim 10 wherein said food product is a dairy product.

20. The feed product according to claim 10 wherein said food product is silage.

* * * * *